(12) United States Patent
Bibb et al.

(10) Patent No.: US 7,166,468 B2
(45) Date of Patent: Jan. 23, 2007

(54) **PRODUCTION OF THE LANTIBIOTIC CINNAMYCIN WITH GENES ISOLATED FROM *STREPTOMYCES CINNAMONEUS***

(75) Inventors: Mervyn James Bibb, Norwich (GB); David Andrew Widdick, Norwich (GB)

(73) Assignee: Plant Bioscience Limited, Norfolk (GB)

( * ) Notice: Subject to any disclaimer, the term of this patent is extended or adjusted under 35 U.S.C. 154(b) by 0 days.

(21) Appl. No.: 10/475,970

(22) PCT Filed: Apr. 29, 2002

(86) PCT No.: PCT/GB02/01983

§ 371 (c)(1),
(2), (4) Date: Oct. 27, 2003

(87) PCT Pub. No.: WO02/088367

PCT Pub. Date: Nov. 7, 2002

(65) Prior Publication Data

US 2004/0101963 A1    May 27, 2004

(30) Foreign Application Priority Data

Apr. 27, 2001   (GB)  ................ 0110432.2

(51) Int. Cl.
   *C12Q 1/68*    (2006.01)
   *C12P 1/04*    (2006.01)
   *C12N 15/00*   (2006.01)
(52) U.S. Cl. .................. 436/6; 435/170; 435/320.1
(58) Field of Classification Search .................. 435/6, 435/320.1, 455
   See application file for complete search history.

(56) References Cited

OTHER PUBLICATIONS

Sahl and Bierbaum (Annu. Rev. Microbiol. 52: 41-79 (1998)).*
Maniatis, T. et al. Molecular Cloning pp. 458-459 (1982).*
Cortina Kaletta, et al. "Prepeptide Sequence of Cinnamycin RO-09-0198 The First Structural Gene of a Duramycin-Type Lantibiotic." *European Journal of Biochemistry.* vol. 199, No. 2, 1991, pp. 411-416. (XP-001093994).
Hans-Georg Sahl, et al. "Biosynthesis and Biological Activities of Lantibiotics With Unique Post-Translation Modiciations." *European Journal of Biochemistry.* vol. 230, No. 3, 1995, pp. 827-853. (XP-001097785).
Hans-Georg Sahl, et al. "Lantibiotics: Biosynthesis and Biological Activities of Uniquely Modified Peptides From Gram-Positive Bacteria." *Annual Review of Microbiology.* vol. 52, 1998, pp. 41-79. (XP-001098220).
Kazuo Hosoda, et al. "Structure Determination of an Immunopotentiator Peptide, Cinnamycin, Compexed With Lysophosphatidylethanolamine by 1H-NMR." *Journal of Biochemistry.* vol. 119, No. 2, 1996, pp. 226-230. (XP-001098548).
Robert G. Benedict, et al. "Cinnamycin, An Antibiotic From *Streptomyces cinnamoneus.*" *Antibiotics & Chemotherapy.* 1952, pp. 591-594. (XP-001095118).
William Dvonch, et al. "Further Studies on Cinnamycin, A Polypeptide Antibiotic." *Antibiotics & Chemotherapy.* 1954, pp. 1135-1142. (XP-001095117).
Roland J. Siezen, et al. "Comparison of Lantibiotic Gene Clusters and Encoded Proteins." *Antonie Van Leeuwenhoek.* vol. 69, No. 2, 1996, pp. 171-184. (XP-001095134).
Karsten Altena, et al. "Biosynthesis of the Lantibiotic Mersacidin: Organization of a Type B Lantibiotic Gene Cluster." *Applied and Environmental Microbiology.* vol. 66, No. 6, Jun. 2000, pp. 2565-2571. (XP-002209341).
Olivia McAuliffe, et al. "Lantibiotics: Structure, Biosynthesis and Mode of Action." *Fems Microbiology Reviews.* vol. 25, No. 3, May 2001, pp. 285-308. (XP-002209342).
International Search Report for International Patent Application No. PCT/GB02/01983, 5 pages, European Patent Office, (mailed Oct. 4, 2002).
Kaletta, C., et al., *Database EMBL*: Accession No. X58545, 1 page, EMBL (1991).
Brotz et al. (1998) "The lantibiotic mersacidin inhibits peptidoglycan synthesis by targeting lipid II" Antimicrob Agents Chemother 42(1):154-160.
Gasson MJ (1995) "Lantibiotics" Biotechnology 28:283-306.
Jack RW and Sahl HG (1995) "Unique peptide modifications involved in the biosynthesis of lantibiotics" Trends Biotechnol 13(7):269-278.
NCBI Sequence Viewer (2001) "Lantibiotic ancovenin sequence" Swissprot P38655.
NCBI Sequence Viewer (2001) "Lantibiotic duramycin C sequence" Swissprot P36503.

* cited by examiner

*Primary Examiner*—Jon Weber
*Assistant Examiner*—Anand U Desai
(74) *Attorney, Agent, or Firm*—Morgan Lewis & Bockius LLP

(57) ABSTRACT

A 17 kb nucleic acid fragment, which confers production of the lantibiotic cinnamycin on non-producer Streptomycete strains, has been isolated from *Streptomyces cinnamoneus cinnamoneus* DSM 40005 and characterized. Also provided are variants of the 17 kb fragment including variants in which non-essential genes are deleted and variants in which the propeptide sequence of the cinnamycin structural gene is altered, for example replaced with the propeptide sequence of similar B-type lantibiotics. Also provided are vectors, host cells and methods of lantibiotic production using the nucleic acid of the invention, and libraries of variants.

48 Claims, 24 Drawing Sheets

Figure 1

```
   1 CATATGGGTA TGGGTAATGC GTATCCNCTG ACATCGCAG CACGGGCGGC
  51 CAATCTGACC GAACGGTTAC GGGTCGTGGC CGCCGCGGGC GGCGAGGNGG
 101 CCGTGCGGGA CACCACGGTC GAACTCGACG CCTTCGACCG CTGGAAGACC
 151 GACACGCTGG CCGGAAAANT GGCCGACAAA TTCCACCAGG AATCGCTGCA
 201 CCGCGGCCGG CCGCCCCAGC ACACCAAGGA CGAACTCGCN GGCGTGCTCT
 251 CCGCCTACCG CCGTCTGGAA CTCGCCCTGG ACACCGCGGA CGACGACGTC
 301 CGGGCACTTC NCGGCGAGCT GCAGAGCGCC TGGCTGCCCA CCTACCGCGC
 351 GGCCCTCGAC GCCCACGACG CCGCCCGCGA CNGCGAACGC ACCGACGCGC
 401 AGGCGGGCGA GGAGCCCGGC TGGCGCGCGT TCGACGTGTA CTACGGCCGG
 451 CTNGCCAAGG CGTGCGAGCC GTTCCTGCGC GAACTGGGCC GCGGCCTGGA
 501 GGCCGCACGC GGCGCCGCAC AGGNCGAGAA CACCGCGCTC TCCCCGCAAC
 551 TGGCCGAGGA CATCCAGCGC CACCTGCTCG ACCGCTTCGA GCTGNGCGTG
 601 GCCTGGGCCG TGGAGGCCGA CGCCAACGTG CACTGCACCC AGGCCGGGAT
 651 CGACAAGGCC GAGGCNACGC GCGAGGACTA CCTCGCCTAC CTCGACACCA
 701 CGTTCTCCGA CAGCGCCGCC TACCACCGCT TCTACCNGAA GTTCCCGGTG
 751 CTCGGCCGCT GGCTCGCCCA CACCACCGCC CTGCTCACCG CGTTCGGCCG
 801 CGACCTCNTC GACAGCCTGG CCGCCGACGC GCAGGCCATC GGCACCGAGT
 851 TCTTCGGGCA GCCGATCACC GCGTTCACNT CCCTGCGGCT GGGCGACTCC
 901 GACCCCCACG CGGGCGCGCG CACCGTCGCC CGCGTCTCCG TCGTGCTCGN
 951 CGACGGGCGC ACCGGCGAGT TCTTCTACAA GCCGCGCAGC GTCCGGTCCG
1001 AGGCGGCGCT CCAGGACGTC NTCGCCAGGC TGCGGACGA CGGGGTCGTC
1051 GACTTCGCGA CCCGGCCCGT CCTGCCCCGG GACGGCTACG GNTACGAGGC
1101 GCTGATCCCC GCCGGACGCA ACCGCGTCGA GACCCCGGAG GAGGTCACCC
1151 GGATCTACCG CGNACTGGGC GGCTACCTGG CGCTGTTCTA CGTCCTGGGC
1201 GGCAGCGACC TCCACTTCGA GAACGTCATC GTCNCCGACG GACACGCCTT
1251 CGTCTGCGAC GCCGAGACCG TCCTCGGCGT CCACCCCCAG GGACGGGCAC
1301 AGTCNGAGGG CACCCTCCTC GACTCCGTCT TCAAGACCGG ACTCCTCGAA
1351 TGGCCGCGCG CCGCGAGCCC GGGCGNGGAG GCCGCCGCCG AGATGCGCAT
1401 CAGCGGCTAC GCGGGCGGCG AGGGATACGA CGTCCCCGTC CCGGAGNCCC
```

```
1451  GCCGCACNGG CGAGGGGNTC AGCTTCGCGG CCTCCGTCGT GCACAAGACC
1501  GGCGTCCACG TCGAGACNAG CGCCTCCAAC CGCGTCTACC TCGGCGAGGA
1551  GCTCGTGCGT CCCGAGGACC ACGTCGAGTC GATCATGGNG GGCTTCAACC
1601  GCGTCTACGA CTGGTTCGCC GAGGACCCCG ACGCGTCCGT CGACTACCTG
1651  ATGGAGACGN TCAGCTGGGT CACCGCCCGC TTCATCAACT GGGGCACCCA
1701  GATCTACGCC CAGCTGCTGA GCGCCGCCCG NCACCCGCGC TGCCTCACCG
1751  AACCCCTCGA AGTGGACCTG CTCGCCAACA CCGTCCGCAC CTTCCCCCGC
1801  ANCTGGGACG CCGAAGGCGT CCTGGCCGGA CGGGAAGTGG CCGCCATGTG
1851  GCAGATGGAC GTGCCGCTGT TCNCCGCGGC CGCCCACGCC GGCAGCTCG
1901  TCCACGGGCA CAGCGACCCG CTGCCCGCCC GGCTGGACAG CTCNCCGATC
1951  GACCACGCGG CCGCACGCAT CCGGCGGCTG TCGGAGCGCA ACCGCGAACA
2001  GCAGAGCCAG TACANCGCCG CCAGCCTCTC GACCGGCGAG ATCAGCAGCC
2051  CCGCCTTCGT CGCCACCTCC CTGGACTACG CGGCCNGGAT CGGCAACCGT
2101  CTGTGCGACG AGCTGCGGGC CCCCGCCGCC TCCGCCCCCT GGACCTCCTA
2151  CCAGCTNTCC GGCGAATCCC TCGCCGAGGT GGACATCGAG GCCGACCTCT
2201  ACCAGGGCTC CGCCGGCGTC GTCCTCTNCC TCGCCTACCT CGACCAGCTC
2251  GTGCCCCGCC CCGAGTACCG CAAGACCGCC CGGCAGGCCC TCGACCATNT
2301  CCTCGTGCAC TGGGACCGCG ACCGGCTCGG CGCCTTCGCC GGACTCGGCG
2351  GCGTCGTCTA CCTCCTCACN CACCTGCACC GCCTCTGGGG CGACGAGGAG
2401  CTCCTCGACC TGGCGGTGCG GCTCAGCGAC GAGCTGCCCG NACGCATCGA
2451  CGAGGACCGG CACTTCGACA TCCTGCACGG CGCGGCCGGC CTCATCCCCG
2501  TCCTCCTCGG CNTCGCCCGG GAGACCGGCG CCACGGCAT CGAGCACGCC
2551  CACCGCTGCG CCGAACACCT GCTGCGCCAC GCNGAGGACG ACGGCACCAC
2601  CCTCAGCTGG CCCCCCTCCG CGGCCGACGA GACGTACGGC AACCTCACCG
2651  GCTNCTCGCA CGGCTCCGGC GGCATCGGCT GGGCGCTCAT CCAGCTCGGC
2701  CGGCACACCG GCAGGACGGA CTACNTCGAG GCCGGGCGCA AGGCGTTCGC
2751  CTACGAGGAC CGGCACGTCG ACGAGCAGGA GAAGGACTGG TACGANCTGC
2801  GGATCAACAA CGGATCCTCT AGAGTCGACC TGCAGGCATG CAAGCTTGGC
2851  GTAATCATGG TCATAGNTGT TTCCTGTGTG AAATTGTTAT CCGCTCACAA
2901  TTCCACACAA CATACGAGCC GGAAGCATAA AGTGTNANGC CTG
```

Figure 2

```
   1 AGATCTACGC CCAGCTGCTG AGCGCCGCCC GCCACCCGAG GTGCCTGACC
  51 GAGCCCCTCG AGGTGGACCT GCTCGCCAAC ACCGTGCGCA CCTTCCCCCG
 101 CACCTGGGAC GCCGAGGGCA TCCTCGCCGC ACGCGAAGTG AACGCCATGT
 151 GGCAGCTGGA CGTGCCGCTG TTCACCGCGG GCGCCCATGC CAGGCAGCTG
 201 GTGCACGCGC ACGGCGAGCC GCTGTCCTCG CGCCTGGACC TCTCGCCCAT
 251 CGACCACGCC GCCGCCCGCA TCAGGCGGCT GTCGGAGGAG AACCGCGAGC
 301 AGCAGAGCCA GTACATCGCC GCCAGTCTCT CCACGGACGA GATCAGCAGC
 351 CCCTCCTTCG TCGCCACTTC CCTGGACTAT GCGGTCAAGA TCGGCAACCG
 401 GCTGTGCGGC GAGCTCAGGG TGCCCGAGGA CCCCGCACCC TGGACCTCGT
 451 ACCAGCTGGC GGGCGGCCGG CTCGAGCAGG TGGACATCGA GGCCGACCTC
 501 TACCAGGGCT CCGCGGGCGT CGTGCTCTTC CTCGCCTACC TCGATCAGCT
 551 CGTGCCCCGG CCGGAGTACC GGCAGGCCGC CCGGCAGGGC CTCGACCACG
 601 TCCTCGCCCA ATGGGACCGC GACCGGCTGG GCGCGTTCGC GGGGCTCGGC
 651 GGCGTCATCT ACCTCCTCAC CCACCTGCAC CGGCTGTGGG GCGACAAGGA
 701 GCTGCTCGAG AAGGCCGTCC GGCTGAGCGA CGAGATCCCC GGACGCATCG
 751 AGGAGGACCG GCACTTCGAC ATCCTGCACG GAGCGGCGGG CCTCATCCCC
 801 GTCCTGATCG GCCTCGCCGA GGAGAGCGGC GGGCACGGCC TCGACCACGC
 851 CCACCGGTGC GCCGGCCACC TGCTGCGGCA CGCCGAGGAC GACGGCGAGA
 901 CCCTCAGCTG GCCGCCGTCC GCGCCCGACG AGACCTACGG CAACCTCACC
 951 GGCTTCTCCC ACGGCTCCGG CGGCATCGGC TGGGCCCTGA TCCAGCTCGG
1001 CCACCACACC GGCCGGAGCG ACTACATCGA GGCCGGGCGC AAGGCCTTCG
         BB3
1051 CCTACGAGGA CCGGTACGTC GACGAGGCGG AGAAGGACTG GTACGACCTG
1101 CGGATCAACA ACGGCTCCGC GGTCAAGGGC GCCCGGCACT TCTCCAACGC
1151 CTGGTGCAAC GGGGCGGCCG GCATCGGGCT CGCCCGGATC ACCAGCTGGG
1201 ACGCGCTCGG CCGCACCGAC GAACAACTGC TGCGCGAGGC CCAGCAGGCG
1251 CTGTCGGCGA CCATGCGCAA CTTCCCCCGG CTGAAGAACC ACACCCTGTG
```

```
1301  CCACGGCACG TCCGGCAACG CCGAGCTCTT CCTGCGCTTC GCCCGGCTCA

1351  ACGACGAACC GGCCTTCCAG CTGGAGGCCA ACGTCCAGGT CCAGGCGCTG

1401  TGGCGGAGCT TCGACGAGGC GGGCGACAGC ACGGCGGACA ACAGTGCCGA

1451  CTTCTTCCCG GGACTGATGA TCGGCATCTC CGGATTCGGC ATGCACTTCC

1501  TGCGGCTGGC GGCCCCGGAC CGCGTCCCGT CCGTGCTGCT CCTCGACCCG

1551  CCGTCGCACC ACGAACAGTA AGGAGTCGCT CCACCATGGC CCTGAAGACC

1601  TGCGAGGAAT TCCTGCGCGA CGCCCTCGAC CCCGACCGCT TCGGCCGGGA

1651  GATGAAGGCG GTCACGGAGA TACCGGAGAT CGTCAAGCTC GGCCACCGCC

1701  ACGGATACGG CTTCACCGCC GAGGAGTTCC TGACGAAGGC CATGTCCTTC

1751  GGCGCCCCGC CGGCCGGTGC CGCGGCGCCA GGGGAGAGCG CGAGCGTGCC

1801  GGGGCAGAAC GGCTCCTCGC CCGGCCACGC CGCCCGGGCC GCCATGGCCG

1851  GCCCGGAGGC CGGCGCCACC AGCTTCGCCC ACTACGAGTA CCGCCTGGAC

1901  GAGCTCCCCG AGTTCGCACC CGTCGTCGCG GAGCTCCCCA AGCTGAAGGT

1951  CATGCCGCCC TCCGTCGGAC CGGACCGCTT CGCCGCCCGC TACCGCGACG

2001  AGGACATGCG GACGATCTCG ATGTCCCCCG CCGACCCCGC CTACCAGGCC

2051  TGGCACCAGG AGCTCGCCGG GCGGGCTGG CGGGACGCCG AGGACACAGC

2101  TGCCGCACCG GACGCACCCC GGCGGGACTT CCACCTCCTC AACCTCGACG

2151  AACACGTCGA CTACCCCGGC TACGAGGAGT ACTTCGCGGC GAAGACCAGG

2201  GTCGTGGCGG CCCTGGAAAA CCTCTTCGGC GGCGACGTGC GCTGCTCGGG

2251  CTCCATGTGG TACCCGCCGT CCAGCTACCG GCTGTGGCAC ACCAACGCCG

2301  ACCAGCCGGG ATGGCGCATG TACCTCGTGG ACGTCGACCG GCCCTTCGCC

2351  GACCCCGACC GGACCTCGTT CTTCCGCTAC CTCCACCCGC GCACCCGGGA

2401  GATCGTCACG CTGCGCGAGA GCCCGCGCAT CGTGCGGTTC TTCAAGGTCG

2451  AGCAGGACCC GGAGAAGCTG TTCTGGCACT GCATCGCCAA CCCCACGGAC

2501  CGGCACCGCT GGAGCTTCGG CTATGTCGTG CCGGAGAACT GGATGGACGC

2551  CCTCCGCCAC CACGGCTGAC CCCGCACCCG TCGCCGCGCG CACCGCGGGG

2601  CACCAAGGAG GAGCGATGTT CGGAGCAGGA CCGCGGACCG CGCGCAAGCC

2651  GGCGGCGGAC GACGGGCCCG CGCGCGAGCC CGACGGGCCG GCGCCGGCCG

2701  ACGGGACCGC GGCCGGGCCC CGGTCCGCGC GGCCCGGCCC GCCGGCCATC
```

```
2751  CTGGCCAGAG GGCTGGGCAA GACGTACGCG GGCGTGGAAG CGGTGCGCGG
2801  CATCGACCTG ACCGTCGCCC AGGGTGAGAC CTTCGGCTTC CTCGGCCCCA
2851  ACGGGGCGGG CAAGACCACG ACGATCTCCA TGCTGACCAC CCTGGCCACG
2901  CCCACCTCGG GCCGGATCGA GATCGCCGGC CACGACACCC GCACCGCCCC
2951  CCAGCAGGTG CGCCGCAACC TCGGGCTGGT CTTCCAGGAG ACCACGTTCG
3001  ACCCGGAGCT GACGGCCGTG GAGAACCTGC GCTTCCACGC CGACCTCTAC
3051  GCCCTGCCGC GCGCCGGGCT GAGCGAGCGC ATCACCGCCA TGCTCGAACT
3101  CGTCGGGCTC GCGGCCCGCG GCGGCAGCCT CGTGCGCACC TTCTCCGGCG
3151  GCATGCAGCG CCGGCTGGAG ATCGCACGCG GCTGCTGCA CCGGCCGCGG
3201  CTGCTCTTCC TCGACGAGCC GACCATCGGC CTCGACCCGC AGACCCGGGC
3251  CCAGGTGTGG ACGCACCTGG CCGAGATCCG CGAACGCGAG GCCACGACCA
3301  TCTTCCTGAC CACGCACTAC CTCGACGAGG CCGAGCAGTG CGACCGCATC
3351  GCCATCATCG ACGACGGCCG GATCGTCGCC CAGGGCAGCC CGGCCGAGCT
3401  GAAGTCGGTC ATCGGGGCCG ACCGCGTGGA CCTGCGCACG GGTGACGACG
3451  TCGCGGCGGC CGCGCTGCTG CGGACACGCT TCGGCCTCGA CCCGGTCCAG
3501  GGCCCGGCCG GCCTCAGCGT CAAGGTCGCG GAGGGCGCCA GGCTCGTCCC
3551  GGCGCTGTGC GCCGCCCTCG ACGTGGCCGT CTACGAGGTG ACCGTCACCC
3601  GCCCCAGCCT CGACGACGTC TTCCTCCACC ACACGGGGCG CGGAATCCGC
3651  GACGACTCAG GAGCCGGCGC ATGACGCACG CCACGGCCGC ACTGCCGGCC
3701  GCCGCCCCCC GCGAAACCGG CCGCATCGCC GCCGAATGGC GCGCCGGCAC
3751  CATGGTGTGG CGACGCGAAA TGATCCACTT CCTGCGCTCG CGCGCCGGGA
3801  TCGCCGTGTC CCTGCTGCAG CCGCTGCTGT TCCTGTACGT GTTGGGCATC
3851  GGCCTGTCCC GGATGTTCAG CGGCGCCGGC TCCTCCGACG ACTACATGGT
3901  GTTCCTTTTC CCAGGCGTGC TGGTGATGGC GGCTCAGGCC CCGGCCATCT
3951  CGGTGGGCGC GTCCATCGTC TGGGACCGGC AGAGCGGGTT CCTGCGCGAG
4001  ATGCTGGTGG CGCCCGTCCA CCGCAGCACC CTGCTGATCG GCAAGTGCCT
4051  CGGCGGCGCC ACCGTCGCGG CGTGCCAGGG CGCGGTCGTC CTGGCCAGCG
4101  CCGGGCTCGT GGGTGTGCCG TACCGGATCG ACCTCTTCGC CGCCCTGCTG
4151  GCCGAACTGC TCCTCGCCTC CCTCGCGATG ACGGTCATGG GCGCGGTGAT
```

```
4201  CGCGGTCAGG ATCCAGCGGA TCCAGACGTT CCATACCGCG CTGACGGTCC
4251  TGACGGCCCC CATGGTCTTC CTGTCGGGGC TGATGTTCCC CGTCAGCGCC
4301  ATGCCGGCCT GGATGGCCTC GCTCACCCTC GTCAACCCCC TGACGTACGC
4351  GGTCGATGCC ATGCGGCAGA CGATCACCGC GTTCCACCCC GCCCCGGCGG
4401  CCGGGGCGTC GGGGGCACCG TTCTTCGACC CGGTCTCCTG GGGAGGCTGG
4451  GACGTCCCGC CGGGGCTGTC GGTGGCCCTG GTGGCCGCGT TCTCCGCGGT
4501  GGCTCTGGCG GTGGCCGCCC GCCGCTTCGC ACGGACCGAC TGAAGTCCCA
4551  CGAAGCGACT GAAAACGCCG TCGTCCCGGG CGACCCAACC GTGGATCATC
4601  GCTCACGACC GTAGCGCCGA ACCGATCAGA GGAGACCGCA CCATGCGCAC
4651  CACCAGACGC CTTTCGCTGC GCCGCCGTAC CGCTCTGCTC ATGGGCACCG
4701  CTTCGCTCGC GGCCCCGATG CTGCTCACGG TCCAGGCCGG CGAGGCGCAG
4751  GCGTTCGGCA CGATCAACTC GCTCGGGCAG CGTGCCGAGC ACGAGCGCAT
4801  CACCCGGGCG GCGCTCGCCT GCGAGCCTGG CCAGGCATCC GACGGGACGT
4851  GTTTCGAGCC GCGCTCGATC GACCAAGTGG CGGGCCACAC CGGCACGTTC
4901  GGGGCCGTGG GCTCGCCCGA CTCGGACGAG ATCT
```

Figure 3

```
  1  GCCTACGAGG ACCGGTACGT CGACGAGGCG GAGAAGGACT GGTACGACCT
 51  GCGGATCAAC AACGGCTCCG CGGTCAAGGG CGCCCGGCAC TTCTCCAACG
101  CCTGGTGCAA CGGGGCGGCC GGCATCGGGC TCGCCCGGAT CACCAGCTGG
151  GACGCGCTCG GCCGCACCGA CGAACAACTG CTGCGCGAGG CCCAGCAGGC
201  GCTGTCGGCG ACCATGCGCA ACTTCCCCCG GCTGAAGAAC CACACCCTGT
251  GCCACGGCAC GTCCGGCAAC GCCGAGCTCT TCCTGCGCTT CGCC
```

Figure 4

```
   1 ggatcccggg ccgttcgccc agcacgagcc ccacacccag cgggaccgcg acgccgccga
  61 gcgcgccgag gggggaaacc acgcccatgg ggcccagggc cagggccttg tagaaggcga
 121 gcatcgccgc cgggccgacg acgccggccg ccaccgcgta ccagagctgg ggcccggcct
 181 cggaccagcc gccggtgccg atcacgatcg cgcccagggc gaggacggcc agcagctggg
 241 agaccaggac cacggtcagg gcgggcatgc gccgggtgag cagcccgccg ccgaagtcgg
 301 ccagccccca catgaggctg gtggccaggg cgaagaccgg tgtcatgggg gagacctcgc
 361 agtacagtgt gatgaacggt ggcgtccacg acaccgtagt acacgatact cgacttacga
 421 gaataatatt ttggacggga tggatcgacc gacgtgacgg acctcgacca gctcacgcaa
 481 tcgctcgccc gcaacctcaa gcgctggcgc ggtgagcgcc acttcaccct cgacgccctg
 541 gcggcccgct ccggcgtcag ccgcggcatg atcatccaga tcgagcaggc ccggacgaac
 601 cccagcgtcg gcaccacggt gaagctcgcc gacgccctgg gcgtcagcat caccacgctg
 661 ctcgactacg agcagggcgc ccgcgtgcgg ctcgtgcccg aggagcaggt ggtgcgcatg
 721 tggtccaccg aggcgggcag ccacacctca ctgctcgtcg gcgccgatgt gcgcggccca
 781 ctggagctgt gggactggcg cctcgtgtcc ggcgacagca gcgtctcgga cccccacccg
 841 cccggcacgg tcgagatgct gaccgtacgg tcgggccgcc tcacgctcgt cgtcgacggc
 901 gaggagcacg aggtcgccgc cggcacctcg gccaccttcg aggccgacgc cccgcacacc
 961 taccgcaacg acggcaccga gcccgtcgag atgacgatgg tggtggccgt ccgcccgcg
1021 ggctgacccc cgagcgcacg gggccgccg ggagacgtcg agcgacgctc tcccggcggg
1081 cccctgtgcg tggtggctcc gtgcgccggt gaagacggtg ctcccgaagg cggtgctccc
1141 gaaggcggtg ttccggaagg cggtgctccc gaagacggtg ctcctgaaag cggagtgaaa
1201 ccgtagtgaa agcggacgct cctagtgtcg ttctcaccgg gaaccgactg gatgggaaa
1261 cgggccatga aaagtgccaa ggaaccgacg atctaccagg acgtggatat catccgccgc
1321 atccaggagc tcatggttct gtgctccttg ctgccgcccg acggcaagct gcgtgaagcg
1381 ctggagttcg ctctctcgct ccacgaggag ccggtactgg cccggatcac tcccctcacc
1441 aatctccatc ccttcgcgac gaaagcctgg ctggagtccc tgtggctcgg cgacggcgtt
1501 tccagcgagg agaaggagct ggtcgcctgg cagaacaaca gcgacaacat gggaccggcc
1561 attcgtgaac tcaagaatcc cgaacagcaa tccggcatca ggctggtcgc acagctgacg
1621 tcctgacacc cgccgggtgc cgggattcac ctcaacatcg gaggtaagcc atgaccgctt
1681 cgattcttca gcagtccgtc gtggacgccg acttccgcgc ggcgctgctc gagaaccccg
1741 ccgccttcgg cgcttccgcc gcggccctgc ccacgcccgt cgaggcccag gaccaggcgt
1801 cccttgactt ctggaccaag gacatcgccg ccacggaagc cttcgcctgc cgccagagct
1861 gcagcttcgg cccgttcacc ttcgtgtgcg acggcaacac caagtaagtg gctgctgcct
1921 ctaggcggta atgctcgccc ggtgcgatga cgcggtgggc cggtgacctg ccggcccacc
1981 gcgttgcgcc gcgcggcggc gccctgcca cgagggtcac gaggctcctt cgacttcgac
2041 cgcaggagaa attcgcatat gggtatgggt aacgcgtatc cgctggacat cgcagcacgg
2101 gcggccaatc tgaccgaacg gttacgggtc gtggccgcgg cggcggcga ggcggccgtg
2161 cgggacaaca cggtcgagct cgacgcctt gaccgctgga aggccgacac gctggccgga
2221 aaactggccg acaagttcca ccaggaatcg ctccaccgcg gccggccgcc ccagcacacc
2281 aaggacgaac tcgccggcgt gctgtccgcc taccgtcgtc tggaactcgg cctggacacc
2341 gcggacgacg acgtccggac gcttctcggc gagctgcaga gcgcctggct gccgcctac
2401 cgtgcggccc tcgacgccca cgacgccgcc cgcgacgacg aacgggccga cgcacagccg
2461 ggcgaggagc ccggctggcg cgggttcgac gtgtactacg gccggctggc gaaggcgtgc
2521 gagccgttcc tgcgcgaact gggtcgcggc ctgggcgccg cgcgcgacgc cgcacagggc
2581 gaaggcgccg cgctctcccc gcagttggcc gaggacatcc agcgccacct gctcgaccgc
2641 ttcgagctga gcctggcctg ggccgtggag gccgacgcca acgtgcactg cacgcaggcc
2701 gggatcgaca aggccgaggc cacccgcgag gactacctcg cctacctcga caccacgttc
2761 tccgacagcg ccgcctacca ccgcttctac ctgaagttcc ccgtgctcgg ccgctggctc
2821 gcccacacca ccgccctgct caccgcgttc ggccgcgacc tcttcgacag cctggccgcc
2881 gacgcggagg ccatcggcac cgaattcttc gggcagcccg tcaccgcgtt cacctcgctg
2941 cgcctcggcg actccgaccc ccacgcgggc gcgcgcaccg tcgcccgcgt cgccgtcgtg
3001 ctcgccgacg gacgcaccgg cgaattcttc tacaagccgc gcagcgtccg gtccgaggcg
3061 gcgctccagg acgtcctcgc caggctggcg gacgacgggg tcgtcgactt cgcgacccgg
3121 cccgtcctgc cccgggacgg ctacggctac gaggcgctga tccccgccgg ccgcaaccgc
3181 gtcgagaccc ccgaagaagt caccccggat taccggaaac tgggcggcta cctggcgctg
3241 ttctacgtcc tgggcggcag cgacctccac ttcgagaacg tcatcgtcgc cgacggcgac
3301 gccttcgtct gcgacgccga gaccgtcctc ggcgtccacc ccaggggcg cgcacagtcg
3361 gagggcaccc tcctcgactc cgtcttcaag accggactcc tcgaatggcc gcgcgccgcg
```

```
3421 agcccgggcg aggaggccgc cgccgagatg cgcatcagcg gctacgcggg cggcgagggc
3481 tacgacgtcc ccgtccggt ggcccgccgc accggcgagg ggctcacctt cgcggcctcc
3541 gtcgtgcaca agaccggcgt ccacgtcgag accagcgcct ccaaccgcgt ctacctcggc
3601 gaggagctcg tgcgtcccga ggaccacgtc gagtcgatca tggagggctt caaccgcgtc
3661 tacgactggt tcgccgagga ccccgacgcg tccgtcgact acctgatgga gacgttcagc
3721 tgggtcaccg cccgcttcat caactgggc acccagatct acgcccagct gctgagcgcc
3781 gcccgccacc cgcgctgcct caccgaaccc ctcgaagtgg acctgctcgc caacaccgtc
3841 cgcaccttcc cccgcacctg ggacgccgag ggcgtcctgg ccggacggga agtggccgcc
3901 atgtggcaga tggacgtgcc gctgttcacc gcggccgccc acgccaggca actcgtccac
3961 gggcacggcg acccgctgtc cgcgcgcctg acagctcccc cgatcgacca cgcggccgcc
4021 cgcatccggc ggctgtcgca gcggaaccgt gaacagcaga gccagtacat cgccgccagc
4081 ctctcgaccg gcgagatcag cagccccgcc ttcgtcgcca cctccctgga ctacgcggcc
4141 aggatcggcg accgcctgtg cgacgagctg cgggcccccg ccgccccgc cccctggacc
4201 tcctaccagc tgtccggcga gtccctcgcc gaagtggaca tcgaggccga cctctaccag
4261 ggctccgccg gcgtcgtcct cttcctcgcc tacctcgacc agctcgtgcc ccgccccgcg
4321 taccgcaagg ccgcccggca ggccctcgac cacgtcctcg tccactggga ccgcgaccgg
4381 ctcggcgcct tcgccggact cggcggcgtc gtctacctcc tcacccacct gcaccgcctg
4441 tggggcgacg aggagctcct cgacctggcc gtgcggctca gcgacgagct gcccgcgcgc
4501 atcgacgagg accggcactt cgacatcctg cacggcgcgg ccggcctcat ccccgtcctg
4561 ctcggcctgg cccaggagac cggcggccac ggcatcgagc acgcccaccg ctgcgccgaa
4621 cacctgctgc gccacgccga ggacgacggc accaccctca gctggccccc ctccgcggcc
4681 gacgagacgt acggcaacct caccggcttc tcgcacggct ccggcggcat cggctgggcg
4741 ctcatccagc tcggccggca caccggccgg tccgactaca tcgaggccgg gcgcaaggcg
4801 ttcgcctacg aggaccggca cgtcgacgag caggagaagg actggtacga cctgcggatc
4861 aacaacggat ccgcggtcaa gggcgcccgt cacttctcca acgcctggtg caacggcgcg
4921 gcgggcatcg gcctcgcccg catcagcagc tgggccgcgc tcgaccgcag cgacgaacaa
4981 ctgctgcgcg acgcacagca ggccctgtcg gcgaccctcc ggaacttccc ccgcctgaag
5041 aaccacaccc tgtgccacgg cacctccggc aacgccgaac tcctcctgcg cttcgcccgg
5101 ctgagcgacg aacccgcctt ccagctggag gccaacgtcc aggtccaggc gctgtggcgg
5161 agcctcgacg aggccggcgg cggcgccggc ggggggcagcg ccgacttctt cccgggactg
5221 atgatcggca tctccgggtt cggcatgcac ttcctgcgac tggcggcccc ggaccgcgtc
5281 ccgtccgtgc tgctcctcga cccgccgtcg caccacgaac agtaaggagt ggctccacca
5341 tggccctgaa gacctgcgag gaattcctgc gcgacgccct cgacccggcc cggttcgggc
5401 gcgagatgaa ggcggtcacg gaggtaccgg agatcgtcga gctcggccgc cgccacggct
5461 acggcttcac cgcggaggag ttcctgacga aggccatgac cttcgacggc acggcggcgg
5521 gcggcacggc cgcgggcggc ccggaggcgg gcgggcaaca ggcccccgg cagacccgc
5581 cccccgggac ccctgcgaac ggcgcgccgg caccggccac cgccaccagc ttcgcccact
5641 acgagtaccg tctggacgac ctcccggagt tcgcgcccgt cgtggccgag ctgccccggc
5701 tcaaggtcat gccacccctcc gcccgcctgg accggttcgc cggcacttc cgcgaggagg
5761 acgcccggac cgtctccacc tcgcccgccg accccgccta ccaggcatgg caccgcgacc
5821 tcgccgcgcg gggctggcag gacgagggcg ccgcgcccgg cgcccgcgc cgcgacttcc
5881 acctcgtcaa cctggacgaa cacgtcgact acccgggcta cgaggactac ttcgccgcga
5941 agacgcgggt cgtggccgcc ctggagaacc tcttcggcgg cgaggtgcgg gcctcgggct
6001 ccatgtggta tccgccgtcg agctaccggc tctggcacac caacgcggac cagccgggat
6061 ggcgcatgta cctggtggac gtggaccggc ccttcgccga ccccggccag acctcctcct
6121 tccgctacct ccacccgcgc acccgcgaga tcgtcaccct caccgagagc ccgcgcatcg
6181 tgcgcttctt caaggtggag caggacccgg agaagctctt ctggcactgc atcgccaacc
6241 ccacggaccg gcaccgctgg agcttcggct acgtcgtgcc ggagacctgg atggacgccc
6301 tccgccacca cggctgaccc ggcacccgtc gtccgcgcac cgcgcggcac caaggaggag
6361 cgatgttcgg agcaggaccg cggacggcgc gggggcccgc ggcggggacg gacggcgacg
6421 ccgcccaccg aagcggccgg ccggcaccgg ccgccggggc cgctggcggc ccgacggccg
6481 ggtccggtcc gccggccgtc ctggcgcggg ggctgggcaa gtcgtacgcg ggagtggaag
6541 ccgtgcgcgg catcgacctg accgtcgccc agggcgagac cttcggcttc ctcggcccca
6601 acggggcggg caagaccacg acgatctcga tgctgaccac cctcgccacg cccaccacgg
6661 gccggatcga gatcgcgggc cacgacaccc gcaccgcacc ccagcaggtg cgccgcaacc
6721 tcgggctggt cttccaggag accacgctcg acccggagct gacggccgtg gagaacctgc
6781 gcttccacgc cgacctctac gcactgccgc gggccggcct ggccgggcgc atcgccgaga
6841 tgctggagct cgtcgggctc tccgcccgcg cgacagcct cgggcgcacc ttctccggcg
6901 gcatgcagcg ccgcctggag atcgcccgcg gcctgctgca ccggccgcgc ctgctcttcc
```

```
6961 tcgacgagcc gaccatcggg ctcgacccgc agacccgcgc ccaggtgtgg gcgcacctgg
7021 ccgaggtccg cgagcgcgag gcgacgacca tcttcctcac cacgcactac ctcgacgagg
7081 ccgagcagtg cgaccgcatc gccatcatcg acgacggccg gatcgtcgcc cagggcagcc
7141 cggccgagct gaagtccgtc atcggcgcgg accgggtgga cctgcgcacc ggtgacgaca
7201 tggccgcggc cgccctgctg cacgagcgct tcggcctggc ggcggtccgg ggcccgaacg
7261 gcctgagcgt caaggtcgcg gaaggcgccc ggctcgtccc ggcgctgtgc gccgccctcg
7321 acgtggccgt ctacgaggtg acggtcaccc gccccagcct cgacgacgtc ttcctccacc
7381 acacggggcg cggcatccgt gacgacgccc tgcccggcgc ggcgggcacg gcaggcacag
7441 ccgaaccgtc ggactcagga gacagcacat gacgcacgcc acggtcgccc tgcccgcggc
7501 cgaccgccac gccccggcc ggctcgccgc cgaatggcgc gcgggcagca tggtgtggcg
7561 gcgcgaaatg atccacttcc tgcgctcgcg cgccgggatc gccgtctccc tgctgcagcc
7621 gctgctgttc ctctacgtgc tgggcatcgg cctgtcccgg atgttcagcg gcgccggctc
7681 gtcggacgac tacatgatct tcctcttccc cggtgtgctg gtgatggcgg cacaggcccc
7741 ggcgatctcg gtgggagcct cgatcgtctg ggaccggcag agcggcttcc tgcgcgagat
7801 gctggtggcc cccgtccgcc gcagcaccct·gctgatcggc aagtgcctgg gcggcgccac
7861 cgtcgccgcc tgccagggcg cggtcgtcct ggccagcgcg ggcctggtgg gcgtgcccta
7921 ccgcgtcgac ctcttcgccg ccctgctggc cgaactcctg ctcgcctccc tggcgatgac
7981 ggtcctcggc gcggtgatcg ccgtgcggat ccagcggatc cagacgttcc acacagcgct
8041 gaccgtcctg acggcaccga tggtcttcct gtcggggctg atgttcccg tcagcgccat
8101 gccggcctgg atggcggcgc tcacctggt caaccccctg acctacgccg tggacgccat
8161 gcgtcagacg atcacggcct ccacccgc gcccgcggcc ggggcatcgg gtgcgcccat
8221 cttcgacccc gtctcctggg gcggctggga cgtaccgccg ggcctgtcgg tggtgctggt
8281 ggccgtgttc tcggccctgg ccctggcggc ggcctcccgg cgcttctccc gcaccgactg
8341 acggcgttcg cggaccgact gaaaacaccg tcgttcccac gcgtccaacc gtggatcatc
8401 actcacgtcc agcgcccgga ttcacatctg aggagacatc accatgcgta gcaccagacg
8461 cctttcgtta cgtcgccgtt ccgccctgct gatgggcgcc gcctccctcg cggcgccggc
8521 gctgctgacg gtccaggccg gcgaggcgca ggcgttcggc acgatcaact cgctgggcca
8581 gcgcgccgag cacgagcgca tcacccgggc ggcgctggcc tgcgccgccg gcacgtcgtc
8641 cgacggatcg tgcttcgagg cccggtcgat cgatcaagtg gccggtcaca cggggacgtt
8701 cggggccgtc gggtcgccgg actcggacga gatcttcacc cccgaggcgc actgcgacga
8761 cgccgactac ctcacggcct ccggctaccc gcgcacccgt cagcaggcca gcgaccagct
8821 cgtcgcctgc atatccaagc tgcagggacg tttcagccag ggcgtcgccg ccggctcggg
8881 caccctgaac ggggacggca cggtctcccc gggcaacagc gacctgtccc aggactgcac
8941 cttcaccggc ggcgtccccg gcgcggcaa gtgcaacgcc atcgagggct tcggccgggc
9001 cctgcacggt gtgcaggact ctactcgca cagcaactgg gcggacaagg cggaccccaa
9061 ccaggccgtg ggcgtcaaca cccgcccgg cctcaacatg tcgggcccg ccccactgct
9121 ctcgctcaag agcggccgcc ctccggcggc ctcctcggtg ccggcgcagc tgtccacggg
9181 ctgtttctcg ctcaacccct ggggctgctc gggccgggtg acccacagca ccctcaacaa
9241 ggacaccggc ctgatcgacc cggccagcgg cgccaccagt gacccgacga cgaaccgcgg
9301 caggatcacc ggcaacttcg accgcgccgt caagggtgcc attgccgaca cccgccgtca
9361 gtgggccgac ttccggaccg cgctgaccga gcgctacggc caggagcgcg gccagcgcat
9421 cgcctgcgtc ctgacgcacg acaacccgt gcgcgactgc cgctgatccc tgcggcccc
9481 gcgtcccgcc ggcccggtgc tccgcgccgg gccggccggc acgcaccgga ccggtcctcg
9541 cgggtcaggc gtcgccgtac gcctcgccgc cgagctccag cacggccgtc ccggcggtgg
9601 tgtccgccag ccaggcccgg aacccctcga cgtcggcctc gggcagcccg atcccgatgc
9661 gcacgccctc gccgtaggcc acctcgcgca cctcgcgccc ggtggcccgc aggtcgttct
9721 gcagcttccc ggccgctgg tggtcgaccg tgaccgtggc cagccggaag cgcttgtggg
9781 tcaccgtgcc gagctcgtcg agggcctcgc cgaccactcc gccgtacgcc cggatcagac
9841 cgcccgcgcc gagcttgacg ccgccgaagt agcgggtgac gaccgccacg acgtagcgca
9901 tgtcgcgccg gaggagcatc tgcagcatgg gcacgccgc ggtgccccg ggctcgccgt
9961 cgtcgctggc cttctggacc gagccgtcgg cgccgaggac gtacgccag cagtggtgcc
10021 gcgcggtcgg gtgctccttg cggatgcgcg cgaggaacgc ctgcgcctcc tcctcggtgg
10081 cggcgggcgc gagcgcgcag atgaagcgcg acctgctgat ctcgatctcg tgcacgcctt
10141 cgagcgcgac cgtgcggtac tcgtcctgca ttccgccagc ctagacgtct ccgcggcgcc
10201 gcccggaccc gggaatggtc cggcgaccta gatcgttgag ccggcatgtt cgcagaaccg
10261 gggatcatcc agaagatcat cgaggggacc ggcgacacct gggcgctggt cggcctctcc
10321 gccaacgagc agcgcgccgc gtacggcgtc gccgaggtgc tccagcgcca cggcaagcgc
10381 atcgttcccg tccacccaa ggccgagacg gtccacggcg agctgggcta cgcctccctc
10441 gccgacatcc ccttcgacgt cgacgtcgtg gacgtcttcg tccggtccga gctcgcgggt
```

```
10501  gccgtcgcgg  acgaggcggt  agagatcggc  gccaaggccg  tctggttcca  gctcggggtg
10561  atcgacgagg  aggcgtacga  ccgcacgcgc  ggggcgggcc  tgctgatggt  catggaccgc
10621  tgcccggcga  tcgaactcgg  ccggccgcgg  ggacgggcgg  tctgacatct  tcctgcgaag
10681  gtctccgcga  acggttgtgc  gaccatgccg  gattcccttg  gaatgtgctc  ctcagtcctt
10741  ttggtcaagg  agtacagatg  cgcaagtccc  ttgctgttgc  ggccgcttcg  gcggttgccg
10801  gcctcacgct  gatggccggc  accccggcga  acgcggcgcc  ggccgccgcc  accaccgtac
10861  cgagctgtgt  gacgtctacc  ttctcgacgc  cgttcttcgc  gatggtccgc  gtcgacatgg
10921  agaacaagtg  caccaccgag  cagcgggtga  agccgtcgtt  caactacgag  ctgaaggacg
10981  ttccgtgcta  cgccctgcag  cccggtcaga  aggcggtgtt  cagccgggac  gtgatcttcg
11041  cctccgggta  cacgttcgcc  ggcctcgtca  gctgctgaca  cccggcccgt  agcggtcacg
11101  gctcacaccg  tcacaccgtc  agtcccgcgt  cgcgggcgca  cagcgccgcc  tgcaccctgt
11161  tgccgacctc  cagggcggcc  aggatgcggc  tgacgtgagc  cttgaccgtg  ctctcccgca
11221  tgcccaggcc  gtcggcgatc  tccgcattgg  aggcgccggc  ggccaggagc  cccaggacgt
11281  ccgactcgcg  ggggggtcagc  cgcgccaggc  gctgctgggc  ggcttggaca  tcgcgggacg
11341  ccgtgcggtg  gtagcggtcg  accagacggc  gggccgcggc  ggggtggagc  atggcctggc
11401  ccgccgcgac  gacctgtatc  gcccggatga  tctcggccgg  atcggtgtcc  ttgaggagga
11461  agcccgaggc  gccggccgcc  agcgcgtcgt  acacgtactg  gtcgaggtcg  aacgtggtca
11521  gcatgacgac  ttccggcggg  ctgggcagcg  cgcgcagccg  ctcggtggcc  gctatcccgt
11581  ccatgcgcgg  catccggacg  tcatcaggg  ccacgtccac  gcgcagggca  ccggcccgct
11641  ggacggcttc  gaggccgtcg  cccgcctgtg  ccacgacctc  aatgccgggg  acgtcgtcga
11701  ggatgtcggc  gagggccagc  cggaccaggc  tgtcgtcgtc  gacgatcaat  gtacggatca
11761  tgccgctccc  ggcgcgaggt  gttcttcgac  agtgctgacg  gggatgtcgg  cggcgatgtt
11821  ccagccaccg  ccccccgaag  gtccgtagtc  cagccggccg  cccagcgccg  tgacgcgctc
11881  ggccagtccg  accagcccgt  agccgctgct  gaccggcggc  tccccggcgg  cggacgccgg
11941  gtcgccggcg  cggttgtgca  cctcgacgct  ggaggccggg  ggaccgtagc  gcacgacgac
12001  ccgcacgggg  gccccgggag  cgtgcttgcg  ggcgttggtc  agcgcctcct  gcaccagccg
12061  gtggacggcg  aggcggtgac  tggccgggag  cggcccggcc  gcgccctcga  cgaccgcgtc
12121  gatctcctgg  ccggccgcgc  gcgcctcgtc  gaagagggcg  ggcagctcgc  gcagccccgg
12181  gacgcgctgc  ccctgcagct  ccgggtggtc  gggatcgcgc  aggacgccca  ggacgtcccg
12241  caggtcgccc  agggcctcgg  tggaagtggt  gcgcagcagt  gcgagccggt  ccgccacggg
12301  ctcgggaagg  gtggcggccc  gccgctgcag  ggctccggcg  tgcaggccca  gcaggctcag
12361  ccggtgggcg  agcacgtcgt  gcatctcggc  ggcgatgcgg  gcccgttcgc  tcagccgcgc
12421  ctgcttggcg  cgcagctcgc  gctcgacgcg  caggtgctcg  acctgcgccg  tcaggctcgc
12481  ctccagccgc  ctacggctgt  ccgcccacag  ccccagcacc  atgacgaggg  cgaacggcag
12541  cacggggccg  tacgcacggg  tgctccacag  caactgctcc  ggctgcgcga  accagttgcc
12601  ggccagcgcc  accgcggcac  acgcacagcc  cagcgcgcgc  cacccgcgcg  aggcgaggta
12661  gaagagcatg  accagcaggg  gcagcagggc  gcccaccacg  accgcggcgc  agacggtcac
12721  caccaccgtg  accaacggga  cgcggtagcg  caccgccaag  gagaggctgc  cgacggcggc
12781  gacggccgtg  tccgggcccc  acagcgtggc  gccggccccc  acgtaggcgt  tctgtacggc
12841  cagcacaccc  acggcggcga  ccagcagcgc  ctccgcccat  cccggccacc  ttcggtcgtc
12901  cgcactcagc  acgggtaaat  cgtagtcacc  caccgttttt  gatccctccg  ccagtcggcc
12961  tacgctaccc  cctactttcg  taccgatcga  gcgtcgcaca  acggccgatg  gtgcgccccg
13021  cggcggcccc  tagtttcatg  gtcatggatc  tgacgcaagc  caactccacg  cccgtacagc
13081  cgcgttcggc  caccgggctg  gccttcctcc  gcgaggcgac  ccgcaccttc  gcaccaccg
13141  gcgcgatcgc  gccgagcagc  cggcagctcg  ccgagcggct  ggccgcgccc  ctcgcccctg
13201  cgagcagact  cgccggccc  accgcggtgc  tggaggtcgg  cgccggcacg  gggccggtga
13261  cccgggttct  ggccggtgcc  gtgggcccg  ccgaccggct  cgacgtcgtc  gagatcaacc
13321  cccgcttcgt  cgagatcctc  aacgcgccc  tgcgcacgga  cccgccatg  tcggcggcct
13381  cggaccgcat  ccggatcatc  cccgagtcga  tcaccgagat  gccatcgac  cacagctacg
13441  acgtcgtcgt  ctcctgcctg  ccgttcacca  acttcgcgcc  ggagacggtc  aggtccatcc
13501  tggaccgcta  cctgtcggtg  ctcgtgccgg  gcggacacct  gacgttcttc  ggctacctcg
13561  gcacccacgc  cacccgctcg  ctgctcagca  gccggaagga  ggccgcccgc  caccgcgaag
13621  tgaccgacct  gctgcacgac  ttcacccgcc  gctacgccag  ccggcagagt  gtcgtgtggc
13681  gcaacatccc  gcccgccgg  gtgtggcacg  tgcgcgcccc  cgagcacgcc  acccgggcgg
13741  cggacgccgc  ctgatgccca  ccgcggacga  gctgttgcac  ggagtgccgc  cgcggccgc
13801  gtacggtctc  gtgctcggcc  tggtgctcct  cgaatcggtg  ctgctgctcg  gttcgttcgt
13861  gcccacgctc  agcctgatgc  tgtgcgccgg  ggtcctggca  caggagggaa  cgctgcggct
13921  gcccctggtg  gtgctgtgcg  ccacgacggg  ggtggtggcc  ggtgacctgc  tcgcgcagcg
13981  caccgggcgc  cgcctcggcc  ccggcctgcg  gcgctcccgg  ctggggaggc  ggctgcccga
```

```
14041 ggcggcctgg gagcgcgcct ggtcggtgct ccagcgccgc ggcggccccg cgctgctggt
14101 ctgccgcttc gtgccggtcg tgcggacctt cgccgcac ctggcgggcg ccgccggcat
14161 gccgtaccgg cggctggccc cgtacagcct ggtggcgggc ctggtctggg cgggcgggga
14221 agccggtgcg ggatacgtgc tgggcgcctc ctacgaccgg ctgaccgcgc cgggcggcgg
14281 gctgcccacg gtctgcgccg ccgccggcgt cctgctggcg gcagcggcgg ggctgctcgt
14341 gcaccgccgg cgcgcgcgcc gggcggtggg cggctcaggc cgagcgggcc agcgacaggc
14401 tgacgtcggt gcgcaggatc gcgacgtgca gatgacgcag ctcgcgcccg gggtccaccc
14461 cgagctcgtc gcggaagacg ccgctgacct ccgcgtacgc ggccagggcc tcgcccctgc
14521 ggccgcagcg gtagagggcg agcatcagcc gctgccacag gctctcgcgc agcgggtact
14581 tcgcggtcag cgtccgcagg tcgccgacga tctcgtcgtg gcggccgagg gcgaggcagg
14641 cgtcgtggta gcgctcgatg gcccggatcc actcctccat cagccccggc accacgtccc
14701 ggtggagcgc gtccgagcgc acgccgccga gcggctggcc gtgccagagg gccagtgcct
14761 cggtgagggc ggagtgctcc agtgcgcggt cgccgagctc ggcggcgagc cgggcgcggg
14821 cggcggattc acggaaaaga gtgagatcca gacagccggt ggggacctcg atcaggtaac
14881 cgctgggcga ggtgtgcagc agtccggaga gccccgcgcc ggctgcgtcc aggctctgtc
14941 gtaagcgggt gaggagggtg tgcagggcgg ggcgcgggct gtgcggcagc tcgtcgcccc
15001 acaccaggtc cacgagtttc tcgaccggga cgatctcgcc cgggtgcacg agcagggccg
15061 ccaggaggga ccgttgccgg ccgctgggta gcgaaacgtt tttcctgccc accgtgacgc
15121 tcagtggtcc gagaactcgg aaggatattg cccggttcat gaactctccc cttcgctcat
15181 cgagccgcac cctgaagacg gctgggact gccgtgtccg ctgtccactc aagcggacgt
15241 cgcggtcagc aagcgtacgg tgcgtacaga gttggttgtc aactatggcg tatgaatgtc
15301 agggttgtct ggcgttatcc atacgctcaa gcggacagaa acagtcgacc gggcaacaac
15361 tcccggggga gggacggggc atgagcgaca gtcgaccggc accggaccgc aacgaccggc
15421 cacttctgcg ccagttcgac cagcggctca gtgaactgat cgccaccacc gccggggccg
15481 agggaacaa gcgcccgga tacgcgcgcc tggccaagga gatccgcgac accaccggcc
15541 ggaccatctc cggcacctac ctgtgggagc tggccaccgg gaagaagcgc aacgtcacgc
15601 tcgaacagct cgacgtcctc gcggagttct tcggtgtgcc cccggagtac ttcctcgacg
15661 acgagaccgg ccgccgcatc gacgaccgcc gaagactggc catcgccctg cgcgacgcca
15721 aggtgcgcaa cctcgccctg cgcgcggacg ggctctcgcc cgactgcctg gacgcgctga
15781 tcgccatggt gaacgaggcg cgcaagaccc agaacctgtc gtccatcgac gatgacgacg
15841 acaccgccac caccttact tcttcagggt agtcaacgac ccgacgccgg tcccgtgggc
15901 ctggaggacc gatgccacgc cgtacgtacg tcgcctaccg ccgctgcctg agaaagggtc
15961 aacgggaacc cgagatgccg tacacgagcg acgccgccct cgtcgacgc tgccgggccc
16021 tgctggcccg cgtcagcctg cccgagccgt tctccgtcga ggtcctgtgc cggcacctcg
16081 gcaacagcgc cggccggccc atccacctgc accgctgcc ggaacaggcc gccctggccg
16141 gggcctgcgg cctgtggctc gccaccgcca ccgacgacca catcttccac gagcgccaca
16201 ccgtccgccc gcaccaggag cacatcgtcc tccacgagat cggccacatg ctcttcgacc
16261 accactcgct ggccccggcc ggcggccgg cgggcgcccc cctggccgac ctcgaccccc
16321 ggctcatccg ccgtctcctc gcgcgcacca actactccac gcgccaggaa cgcgaggcgg
16381 agatgctcgc cagcctgatc cgcaccagcg tccgcgccgg caccggggaa cggccgccgg
16441 gcgcgctggg ccggctgcag gcggcgctgg gcgtggtcgg gtccatggc cgctgacgtc
16501 ctcgattccg tcctggggac caccgggctg gtgtgcctgt ggaccgcgt ggtcctgcga
16561 tgtccctacg ccgtgcgcca ccccgcacag cgcggactgt ggctggcgt ggccacggcg
16621 gccctggcga tgaccctcac cacctccatc ggctccgtcg tccccgaagc ggcgctcggg
16681 ctcgccggca acctcaccgg catggtctcc gcgggcgccg tcctcggctt cgtcatcacg
16741 atcatgggcg ggcggcgcct gcacacctgg gcctgcggca cggtcgccgc cacggccctc
16801 gccctgaccg tcctcggcgt cacctccggg gcccacctct cctacggcac catcgccgag
16861 atcccgccca ccgccaccgc ctaccggctg ctgctgatcg gcacccacct ggccgtgaac
16921 gcggcctgca tcgcggtgtg ctggcggtac gggagggggc ccagccgctc cccgctcgcc
16981 ctcggcctgc ggctcttcgg catcggcacc gtcctggcgg agctgtactg gctgcgcctg
17041 ttcgccggcc tcttcaccac ctccgacgcc ctcctgcggt acc
```

Figure 6

```
   1  CTGCAGCCGC TGCTGTTCCT CTACGTGCTG GGCATCGGCC TGTCCCGGAT
  51  GTTCAGCGGC GCCGGCTCGT CGGACGACTA CATGATCTTC CTCTTCCCCG
 101  GTGTGCTGGT GATGGCGGCA CAGGCCCCGG CGATCTCGGT GGGAGCCTCG
 151  ATCGTCTGGG ACCGGCAGAG CGGCTTCCTG CGCGAGATGC TGGTGGCCCC
 201  CGTCCGCCGC AGCACCCTGC TGATCGGCAA GTGCCTGGGC GGCGCCACCG
 251  TCGCCGCCTG CCAGGGCGCG GTCGTCCTGG CCAGCGCGGG CCTGGTGGGC
 301  GTGCCCTACC GCGTCGACCT CTTCGCCGCC CTGCTGGCCG AACTCCTGCT
 351  CGCCTCCCTG GCGATGACGG TCCTCGGCGC GGTGATCGCC GTGCGGATCC
 401  AGCGGATCCA GACGTTCCAC ACAGCGCTGA CCGTCCTGAC GGCACCGATG
 451  GTCTTCCTGT CGGGGCTGAT GTTCCCCGTC AGCGCCATGC CGGCCTGGAT
 501  GGCGGCGCTC ACCCTGGTCA ACCCCCTGAC CTACGCCGTG GACGCCATGC
 551  GTCAGACGAT CACGGCCTTC CACCCCGCGC CGCGGCCGG GGCATCGGGT
 601  GCGCCCATCT TCGACCCCGT CTCCTGGGGC GGCTGGGACG TACCGCCGGG
 651  CCTGTCGGTG GTGCTGGTGG CCGTGTTCTC GGCCCTGGCC CTGGCGGCGG
 701  CCTCCCGGCG CTTCTCCCGC ACCGACTGAC GGCGTTCGCG GACCGACTGA
 751  AAACACCGTC GTTCCCACGC GTCCAACCGT GGATCATCAC TCACGTCCAG
 801  CGCCCGGATT CACATCTGAG GAGACATCAC CATGCGTAGC ACCAGACGCC
 851  TTTCGTTACG TCGCCGTTCC GCCCTGCTGA TGGGCGCCGC CTCCCTCGCG
 901  GCGCCGGCGC TGCTGACGGT CCAGGCCGGC GAGGCGCAGG CGTTCGGCAC
 951  GATCAACTCG CTGGGCCAGC GCGCCGAGCA CGAGCGCATC ACCCGGGCGG
1001  CGCTGGCCTG CGCCGCCGGC ACGTCGTCCG ACGGATCGTG CTTCGAGGCC
1051  CGGTCGATCG ATCAAGTGGC CGGTCACACG GGACGTTCG GGGCCGTCGG
1101  GTCGCCGGAC TCGGACGAGA TCCCCCGGGCTGCAG
```

MTPVFALATSLMWGLADFGGGLLTRRMPALTVVLVSQLLAVLALGAIVIGTGGWSEAGPQ
LWYAVAAGVVGPAAMLAFYKALALGPMGVVSPLGALGGVAVPLGVGLVLGERPG

MTDLDQLTQSLARNLKRWRGERHFTLDALAARSGVSRGMIIQIEQARTNPSVGTTVKLAD
ALGVSITTLLDYEQGARVRLVPEEQVVRMWSTEAGSHTSLLVGADVRGPLELWDWRLVSG
DSSVSDPHPPGTVEMLTVRSGRLTLVVDGEEHEVAAGTSATFEADAPHTYRNDGTEPVEM
TMVVAVPPAG

MKTVLPKAVLPKAVFRKAVLPKTVLLKAE

MKSAKEPTIYQDVDIIRRIQELMVLCSLLPPDGKLREALEFALSLHEEPVLARITPLTNL
HPFATKAWLESLWLGDGVSSEEKELVAWQNNSDNMGPAIRELKNAEQQSGIRLVAQLTS

MTASILQQSVVDADFRAALLENPAAFGASAAALPTPVEAQDQASLDFWTKDIAATEAFAC
RQSCSFGPFTFVCDGNTK

MGMGNAYPLDIAARAANLTERLRVVAAAGGEAAVRDNTVELDAFDRWKADTLAGKLADKF
HQESLHRGRPPQHTKDELAGVLSAYRRLELGLDTADDDVRTLLGELQSAWLPAYRAALDA
HDAARDDERADAQPGEEPGWRGFDVYYGRLAKACEPFLRELGRGLGAARDAAQGEGAALS
PQLAEDIQRHLLDRFELSLAWAVEADANVHCTQAGIDKAEATREDYLAYLDTTFSDSAAY
HRFYLKFPVLGRWLAHTTALLTAFGRDLFDSLAADAEAIGTEFFGQPVTAFTSLRLGDSD
PHAGARTVARVAVVLADGRTGEFFYKPRSVRSEAALQDVLARLADDGVVDFATRPVLPRD
GYGYEALIPAGRNRVETPEEVTRIYRELGGYLALFYVLGGSDLHFENVIVADGHAFVCDA
ETVLGVHPQGRAQSEGTLLDSVFKTGLLEWPRAASPGEEAAAEMRISGYAGGEGYDVPVP
VARRTGEGLTFAASVVHKTGVHVETSASNRVYLGEELVRPEDHVESIMEGFNRVYDWFAE
DPDASVDYLMETFSWVTARFINWGTQIYAQLLSAARHPRCLTEPLEVDLLANTVRTFPRT
WDAEGVLAGREVAAMWQMDVPLFTAAAHARQLVHGHGDPLSARLDSSPIDHAAARIRRLS
QRNREQQSQYIAASLSTGEISSPAFVATSLDYAARIGDRLCDELRAPAAPAPWTSYQLSG
ESLAEVDIEADLYQGSAGVVLFLAYLDQLVPRPAYRKAARQALDHVLVHWDRDRLGAFAG
LGGVVYLLTHLHRLWGDEELLDLAVRLSDELPARIDEDRHFDILHGAAGLIPVLLGLAQE
TGGHGIEHAHRCAEHLLRHAEDDGTTLSWPPSAADETYGNLTGFSHGSGGIGWALIQLGR
HTGRSDYIEAGRKAFAYEDRHVDEQEKDWYDLRINNGSAVKGARHFSNAWCNGAAGIGLA
RISSWAALDRSDEQLLRDAQQALSATLRNFPRLKNHTLCHGTSGNAELLLRFARLSDEPA
FQLEANVQVQALWRSLDEAGGGAGGGSADFFPGLMIGISGFGMHFLRLAAPDRVPSVLLL
DPPSHHEQ

MALKTCEEFLRDALDPARFGREMKAVTEVPEIVELGRRHGYGFTAEEFLTKAMTFDGTAA
GGTAAGGPEAGGQQAPRQTPPPGTPANGAPAPATATSFAHYEYRLDDLPEFAPVVAELPR
LKVMPPSARLDRFAGHFREEDARTVSTSPADPAYQAWHRDLAARGWQDEGAAPGAPRRDF
HLVNLDEHVDYPGYEDYFAAKTRVVAALENLFGGEVRASGSMWYPPSSYRLWHTNADQPG
WRMYLVDVDRPFADPGQTSFFRYLHPRTREIVTLTESPRIVRFFKVEQDPEKLFWHCIAN
PTDRHRWSFGYVVPETWMDALRHHG

MRGIDLTVAQGETFGFLGPNGAGKTTTISMLTTLATPTTGRIEIAGHDTRTAPQQVRRNL
GLVFQETTLDPELTAVENLRFHADLYALPRAGLAGRIAEMLELVGLSARGDSLGRTFSGG
MQRRLEIARGLLHRPRLLFLDEPTIGLDPQTRAQVWAHLAEVREREATTIFLTTHYLDEA
EQCDRIAIIDDGRIVAQGSPAELKSVIGADRVDLRTGDDMAAAALLHERFGLAAVRGPNG
LSVKVAEGARLVPALCAALDVAVYEVTVRPSLDDVFLHHTGRGIRDDALPGAAGTAGTA
EPSDSGDST

MTHATVALPAADRHAPGRLAAEWRAGSMVWRREMIHFLRSRAGIAVSLLQPLLFLYVLGI
GLSRMFSGAGSSDDYMIFLFPGVLVMAAQAPAISVGASIVWDRQSGFLREMLVAPVRRST
LLIGKCLGGATVAACQGAVVLASAGLVGVPYRVDLFAALLAELLLASLAMTVLGAVIAVR
IQRIQTFHTALTVLTAPMVFLSGLMFPVSAMPAWMAALTLVNPLTYAVDAMRQTITAFHP
APAAGASGAPIFDPVSWGGWDVPPGLSVVLVAVFSALALAAASRRFSRTD

MRSTRRLSLRRRSALLMGAASLAAPALLTVQAGEAQAFGTINSLGQRAEHERITRAALAC
AAGTSSDGSCFEARSIDQVAGHTGTFGAVGSPDSDEIFTPEAHCDDADYLTASGYPRTRQ
QASDQLVACISKLQGRFSQGVAAGSGTLNGDGTVSPGNSDLSQDCTFTGGVPGRGKCNAI
EGFGRALHGVQDFYSHSNWADKADPNQAVGVNNPPGLNMSGPAPLLSLKSGRPPAASSVP
AQLSTGCFSLNPWGCSGRVTHSTLNKDTGLIDPASGATSDPTTNRGRITGNFDRAVKGAI
ADTRRQWADFRTALTERYGQERGQRIACVLTHDNPVRDCR

MQDEYRTVALEGVHEIEISRSRFICALAPAATEEEAQAFLARIRKEHPTARHHCWAYVLG
ADGSVQKASDDGEPGGTAGVPMLQMLLRRDMRYVVAVVTRYFGGVKLGAGGLIRAYGGVV
GEALDELGTVTHKRFRLATVTVDHQRAGKLQNDLRATGREVREVAYGEGVRIGIGLPEAD
VEGFRAWLADTTAGTAVLELGGEAYGDA

MFAEPGIIQKIIEGTGDTWALVGLSANEQRAAYGVAEVLQRHGKRIVPVHPKAETVHGEL
GYASLADIPFDVDVVDVFVRSELAGAVADEAVEIGAKAVWFQLGVIDEEAYDRTRGAGLL
MVMDRCPAIELGRPRGRAV

MRKSLAVAAASAVAGLTLMAGTPANAAPAAATTVPSCVTSTFSTPFFAMVRVDMENKCTT
EQRVKPSFNYELKDVPCYALQPGQKAVFSRDVIFASGYTFAGLVSC

MIRTLIVDDDSLVRLALADILDDVPGIEVVAQAGDGLEAVQRAGALRVDVALMDVRMPRM
DGIAATERLRALPSPPEVVMLTTFDLDQYVYDALAAGASGFLLKDTDPAEIIRAIQVVAA
GQAMLHPAAARRLVDRYHRTASRDVQAAQQRLARLTPRESDVLGLLAAGASNAEIADGLG
MRESTVKAHVSRILAALEVGNRVQAALCARDAGLTV

MGAGATLWGPDTAVAAVGSLSLAVRYRVPLVTVVVTVCAAVVVGALLPLLVMLFYLASRG
WRALGCACAAVALAGNWFAQPEQLLWSTRAYGPVLPFALVMVLGLWADSRRRLEASLTAQ
VEHLRVERELRAKQARLSERARIAAEMHDVLAHRLSLLALHAGALQRRAATLPEPVADRL
ALLRTTSTEALGDLRDVLGVLRDPDHPELQGQRVPGLRELPALFDEARAAGQEIDAVVEG
AAGPLPASHRLAVHRLVQEALTNARKHAPGAPVRVVVRYGPPASSVEVHNRAGDPASAAG
EPPVSSGYGLVGLAERVTALGGRLDYGPSGGGGWNIAADIPVSTVEEHLAPGAA

MTRVLAGAVGPADRLDVVEINPRFVEILNGALRTDPAMSAASDRIRIIPESITEMPIDHS
YDVVVSCLPFTNFAPETVRSILDRYLSVLVPGGHLTFFGYLGTHATRSLLSSRKEAARHR
EVTDLLHDFTRRYASRQSVVWRNIPPARVWHVRAPEHATRAADAA

MPTADELLHGVPPAAAYGLVLGLVLLESVLLLGSFVPTLSLMLCAGVLAQEGTLRLPLVV
LCATTGVVAGDLLAQRTGRRLGPGLRRSRLGRRLPEAAWERAWSVLQRRGGPALLVCRFV
PVVRTFAPHLAGAAGMPYRRLAPYSLVAGLVWAGGEAGAGYVLGASYDRLTAPGGGLPTV
CAAAGVLLAAAAGLLVHRRRARRAVGGSGRAGQRQADVGAQDRDVQMTQLAPGVHPELVA
EDAADLRVRGQGLAPAAAAVEGEHQPLPQALAQRVLRGQRPQVADDLVVAAEGEAGVVVA
LDGPDPLLHQPRHHVPVERVRAHAAERLAVPEGQCLGEGGVLQCAVAELGGEPGAGGGFT
EKSEIQTAGGDLDQVTAGRGVQQSGEPRAGCVQALS

MNRAISFRVLGPLSVTVGRKNVSLPSGRQRSLLAALLVHPGEIVPVEKLVDLVWGDELPH
SPRPALHTLLTRLRQSLDAAGAGLSGLLHTSPSGYLIEVPTGCLDLTLFRESAARARLAA
ELGDRALEHSALTEALALWHGQPLGGVRSDALHRDVVPGLMEEWIRAIERYHDACLALGR
HDEIVGDLRTLTAKYPLRESLWQRLMLALYRCGRRGEALAAYAEVSGVFRDELGVDPGRE
LRHLHVAILRTDVSLSLARSA

MSDSRPAPDRNDRPLLRQFDQRLSELIATTAGAEGNKRPGYARLAKEIRDTTGRTISGTY
LWELATGKKRNVTLEQLDVLAEFFGVPPEYFLDDETGRRIDDRRRLAIALRDAKVRNLAL
RADGLSPDCLDALIAMVNEARKTQNLSSIDDDDDTATTLTSSG

MPRRTYVAYRRCLRKGQREPEMPYTSDAALRRRCRALLARVSLPEPFSVEVLCRHLGEQR
GRPIHLHPLPEQAALAGACGLWLATATDDHIFHERHTVRPHQEHIVLHEIGHMLFDHHSL
APAGGPAGALLADLDPRLIRRLLARTNYSTRQEREAEMLASLIRTSVRAGTGERPPGALG
RLQAALGVVGSHGR

MVLRCPYAVRHPAQRGLWLAVATAALAMTLTTSIGSVVPEAALGLAGNLTGMVSAGAVLG
FVITIMGGRRLHTWACGTVAATALALTVLGVTSRAHLSYGTIAEIPPTATAYRLLLIGTH
LAVNAACIAVCWRYGRGPSRSPLALGLRLFGIGTVLAELYWLRLFAGLFTTSDALLR

Figure 28

```
   1 CCCGGGCCGT TCGCCCACCA CGAGCCCCAC GCCCAGCGGC ACCGCCACGC
  51 CCCCGAGGGC ACCCAGCGGC NAGACGACGC CATGGGGCC CAGGGCCAGG
 101 GCCTTGTAGA AGGCGAGCAT CGCCGCGGGG CCCACGACGC CNGCGGCCAC
 151 CGCGTACCAG AGCCCGGGGC CGGCCTCGGA CCAGCCGCCG GTGCCGATCA
 201 CGATCGTGCC CANGGCGAGG ACGGCCAGCA GCTGGGACAC CAGGACCACG
 251 GTCAGGGCGG GCATGCGCCG GGTGAGCAGC CCGNCGCCGA AGTCGGCCAG
 301 CCCCCACATG AGGCTGGTGG CCAGGGCGAA GACCGGTGTC ATGGGGGAGA
 351 CCTCNCAGTA CAGTGTGATG AACGGTGGCG TCCACGACAC CGTAGTACAT
 401 GATGCTCGAC TTGCAAGAAT AATATNTTGG ACGGGACGGA TCGGACCGAC
 451 GTGACGGACC TCGACCAGCT CACGCAATCG CTCGCCCGCA ACCTCANGCG
 501 CTGGCGCGGT GAGCGCCACT TCACCCTCGA CGCCCTCGCG GCCCGCTCCG
 551 GCGTCAGCCG CGGCATGNTC ATCCAGATCG AGCAGGCCCG GACGAACCCC
 601 AGCGTCGGCA CCACGGTGAA GCTCGCCGAC GCCCTCGGNG TCAGCATCAC
 651 CACCCTGCTC GACTACGAGC AGGGCGCCCG CGTGCGGCTC GTACCCGAGG
 701 AGCAGGTGGN CCGCATGTGG TCCACCGAGG CGGGCAGCCA CACCTCGCTG
 751 CTCGTCGGCG CCGATGTCCG CGGCCCGCTG NAACTGTGGG ACTGGCGCCT
 801 CGTGCCCGGC GACAGCAGCG TCTCGGACCC CCACCCGCCC GGCACCGTCG
 851 ANATGCTGAC CGTACGGTCG GGCCGCCTCA CGCTCGTCGT CGACGGCGAG
 901 GAGTACGAGG TCGCCGCCGG CANCTCGGCC ACCTTCGAGG CCGACGCCGC
 951 ACACACCTAC CGCAACGACG GCACCGAGCC CGTCGAGATG ACGNTGGTGG
1001 TGGCCGTCCC GCCCGCGGGC TGACAGCCGC CGGCCCCTGA ACGCACCGGG
1051 CCCGCCGGGA GACGNCGAGC GACGCTCTCC CGGCGGGCCT CCGTGCGTGG
1101 TTGCCCCGTG CGCCGGTGAA GACGGTGCTT CCGAANCCGG GCTTCCCAAG
1151 TCGGTGCTCC TGAAAGCGGA GTGAAACCGT AGTGAAAGCG GACGCTCCTA
1201 ATGTCTNTCT CACCGGGAAC CGACTGGATG GGGAAACGGG CCATGAAAAG
1251 TGCCAAGGAA CCGACGATCT ACCAGGANGT GGAGATCATC CGCCGCATCC
1301 AGGAGCTCAT GGTTCTCTGC TCCTTGCTGC CGCCCGACGG CAAGCTGCNT
1351 GAAGCGCTGG AGTTCGCTCT CTCGCTCCAC GAGGAGCCGG TACTGGCCCG
1401 GATCACTCCC CTCACCAATN TCCATCCCTT CGCGACGAAA GCCTGGCTGG
```

```
1451  AGTCCCTGTG GCTCGGCGAA GGCGTTTCCA GCGAGGAGAA NGAGCTGGTC
1501  GCCTGGCAGA ACAACAGCGA CAACATGGGA CCGGCCATTC GTGAACTCAA
1551  GAATGCCGAA CNGCAGTCCG GCATCAGGCT GGTCGCTCAG CTGACGTCCT
1601  GACACCCGCC TGGGTGCCGG GATTCACCTC AANATCGGAG GTAAGCCATG
1651  ACCGCTTCCA TTCTTCAGCA GTCCGTCGTG GACGCCGACT TCCGCGCGGC
1701  GCTNCTTGAG AACCCCGCCG CCTTCGGCGC TTCCGCCGCG GCCCTGCCCA
1751  CGCCCGTCGA GGCCCAGGAC CAGGNGTCCC TTGACTTCTG GACCAAGGAC
1801  ATCGCCGCCA CGGAAGCCTT CGCCTGCCGC CAGAGCTGCA GCTTCNGCCC
1851  GTTCACCTTC GTGTGCGACG CAACACCAA GTAAGTGGCT GCTGCCTCTA
1901  GGCGGTAATG CTCGCCNGGT GCGATGACGC GGTGGGCCGG TGACCTGCCG
1951  GCCCACCGCG TTGCGCCGCG CGGCGGCGCC CCTGCCANGA GGGTCACGAG
2001  GCTCCTTCGA CTTCGACCGC AGGAGAAATT CGCATATGGG TATGGGTAAT
2051  GCGTATCCNC TGGACATCGC AGCACGGGCG GCCAATCTGA CCGAACGGTT
2101  ACGGGTCGTG GCCGCCGCGG GCGGCGAGGN GGCCGTGCGG GACACCACGG
2151  TCGAACTCGA CGCCTTCGAC CGCTGGAAGA CCGACACGCT GGCCGGAAAA
2201  NTGGCCGACA AATTCCACCA GGAATCGCTG CACCGCGGCC GGCCGCCCCA
2251  GCACACCAAG GACGAACTCG CNGGCGTGCT CTCCGCCTAC CGCCGTCTGG
2301  AACTCGCCCT GGACACCGCG GACGACGACG TCCGGGCACT TCNCGGCGAG
2351  CTGCAGAGCG CCTGGCTGCC CACCTACCGC GCGGCCCTCG ACGCCCACGA
2401  CGCCGCCCGC GACNGCGAAC GCACCGACGC GCAGGCGGGC GAGGAGCCCG
2451  GCTGGCGCGC GTTCGACGTG TACTACGGCC GGCTNGCCAA GGCGTGCGAG
2501  CCGTTCCTGC GCGAACTGGG CCGCGGCCTG GAGGCCGCAC GCGGCGCCGC
2551  ACAGGNCGAG AACACCGCGC TCTCCCCGCA ACTGGCCGAG GACATCCAGC
2601  GCCACCTGCT CGACCGCTTC GAGCTGNGCG TGGCCTGGGC CGTGGAGGCC
2651  GACGCCAACG TGCACTGCAC CCAGGCCGGG ATCGACAAGG CCGAGGCNAC
2701  GCGCGAGGAC TACCTCGCCT ACCTCGACAC CACGTTCTCC GACAGCGCCG
2751  CCTACCACCG CTTCTACCNG AAGTTCCCGG TGCTCGGCCG CTGGCTCGCC
2801  CACACCACCG CCCTGCTCAC CGCGTTCGGC CGCGACCTCN TCGACAGCCT
2851  GGCCGCCGAC GCGCAGGCCA TCGGCACCGA GTTCTTCGGG CAGCCGATCA
```

```
2901  CCGCGTTCAC NTCCCTGCGG CTGGGCGACT CCGACCCCCA CGCGGGCGCG
2951  CGCACCGTCG CCCGCGTCTC CGTCGTGCTC GNCGACGGGC GCACCGGCGA
3001  GTTCTTCTAC AAGCCGCGCA GCGTCCGGTC CGAGGCGGCG CTCCAGGACG
3051  TCNTCGCCAG GCTGGCGGAC GACGGGGTCG TCGACTTCGC GACCCGGCCC
3101  GTCCTGCCCC GGGACGGCTA CGGNTACGAG GCGCTGATCC CCGCCGGACG
3151  CAACCGCGTC GAGACCCCGG AGGAGGTCAC CCGGATCTAC CGCGNACTGG
3201  GCGGCTACCT GGCGCTGTTC TACGTCCTGG GCGGCAGCGA CCTCCACTTC
3251  GAGAACGTCA TCGTCNCCGA CGGACACGCC TTCGTCTGCG ACGCCGAGAC
3301  CGTCCTCGGC GTCCACCCCC AGGGACGGGC ACAGTCNGAG GGCACCCTCC
3351  TCGACTCCGT CTTCAAGACC GGACTCCTCG AATGGCCGCG CGCCGCGAGC
3401  CCGGGCGNGG AGGCCGCCGC CGAGATGCGC ATCAGCGGCT ACGCGGGCGG
3451  CGAGGGATAC GACGTCCCCG TCCCGGAGNC CCGCCGCACN GGCGAGGGGN
3501  TCAGCTTCGC GGCCTCCGTC GTGCACAAGA CCGGCGTCCA CGTCGAGACN
3551  AGCGCCTCCA ACCGCGTCTA CCTCGGCGAG GAGCTCGTGC GTCCCGAGGA
3601  CCACGTCGAG TCGATCATGG NGGGCTTCAA CCGCGTCTAC GACTGGTTCG
3651  CCGAGGACCC CGACGCGTCC GTCGACTACC TGATGGAGAC GNTCAGCTGG
3701  GTCACCGCCC GCTTCATCAA CTGGGGCACC CAGATCTACG CCCAGCTGCT
3751  GAGCGCCGCC CGNCACCCGC GCTGCCTCAC CGAACCCCTC GAAGTGGACC
3801  TGCTCGCCAA CACCGTCCGC ACCTTCCCCC GCANCTGGGA CGCCGAAGGC
3851  GTCCTGGCCG GACGGGAAGT GGCCGCCATG TGGCAGATGG ACGTGCCGCT
3901  GTTCNCCGCG GCCGCCCACG CCCGGCAGCT CGTCCACGGG CACAGCGACC
3951  CGCTGCCCGC CCGGCTGGAC AGCTCNCCGA TCGACCACGC GGCCGCACGC
4001  ATCCGGCGGC TGTCGGAGCG CAACCGCGAA CAGCAGAGCC AGTACANCGC
4051  CGCCAGCCTC TCGACCGGCG AGATCAGCAG CCCCGCCTTC GTCGCCACCT
4101  CCCTGGACTA CGCGGCCNGG ATCGGCAACC GTCTGTGCGA CGAGCTGCGG
4151  GCCCCGCCG CCTCCGCCCC CTGGACCTCC TACCAGCTNT CCGGCGAATC
4201  CCTCGCCGAG GTGGACATCG AGGCCGACCT CTACCAGGGC TCCGCCGGCG
4251  TCGTCCTCTN CCTCGCCTAC CTCGACCAGC TCGTGCCCCG CCCCGAGTAC
4301  CGCAAGACCG CCCGGCAGGC CCTCGACCAT NTCCTCGTGC ACTGGGACCG
4351  CGACCGGCTC GGCGCCTTCG CCGGACTCGG CGGCGTCGTC TACCTCCTCA
```

```
4401  CNCACCTGCA  CCGCCTCTGG  GGCGACGAGG  AGCTCCTCGA  CCTGGCGGTG

4451  CGGCTCAGCG  ACGAGCTGCC  CGNACGCATC  GACGAGGACC  GGCACTTCGA

4501  CATCCTGCAC  GGCGCGGCCG  GCCTCATCCC  CGTCCTCCTC  GGCNTCGCCC

4551  GGGAGACCGG  CGGCCACGGC  ATCGAGCACG  CCCACCGCTG  CGCCGAACAC

4601  CTGCTGCGCC  ACGCNGAGGA  CGACGGCACC  ACCCTCAGCT  GGCCCCCCTC

4651  CGCGGCCGAC  GAGACGTACG  GCAACCTCAC  CGGCTNCTCG  CACGGCTCCG

4701  GCGGCATCGG  CTGGGCGCTC  ATCCAGCTCG  GCCGGCACAC  CGGCAGGACG

4751  GACTACNTCG  AGGCCGGGCG  CAAGGCGTTC  GCCTACGAGG  ACCGGCACGT

4801  CGACGAGCAG  GAGAAGGACT  GGTACGANCT  GCGGATCAAC  AACGGATCCT

4851  CTAGAGTCGA  CCTGCAGGCA  TGCAAGCTTG  GCGTAATCAT  GGTCATAGNT

4901  GTTTCCTGTG  TGAAATTGTT  ATCCGCTCAC  AATTCCACAC  AACATACGAG

4951  CCGGAAGCAT  AAAGTGTNAN  GCCTG
```

Figure 29

```
   1 AGGCCTCGCC GGCTTCCATT CAGGTCGAGG TGGCCCGGCT CCATGCACCG
  51 CGACGCAACG CGGGGAGGCA GACAAGGTAT AGGGCGGCGC CTACAATCCA
 101 TGCCAACCCG TTCCATGTGC TCGCCGAGGC GGCATAAATC GCCGTGACGA
 151 TCAGCGGTCC AGTGATCGAA GTTAGGCTGG TAAGAGCCGC GAGCGATCCT
 201 TGAAGCTGTC CCTGATGGTC GTCATCTACC TGCCTGGACA GCATGGCCTG
 251 CAACGCGGGC ATCCCGATGC CGCCGGAAGC GAGAAGAATC ATAATGGGGA
 301 AGGCCATCCA GCCTCGCGTC GCGAACGCCA GCAAGACGTA GCCCAGCGCG
 351 TCGGCCGCCA TGCCGGCGAT AATGGCCTGC TTCTCGCCGA AACGTTTGGT
 401 GGCGGGACCA GTGACGAAGG CTTGAGCGAG GGCGTGCAAG ATTCCGAATA
 451 CCGCAAGCGA CAGGCCGATC ATCGTCGCGC TCCAGCGAAA GCGGTCCTCG
 501 CCGAAAATGA CCCAGAGCGC TGCCGGCACC TGTCCTACGA GTTGCATGAT
 551 AAAGAAGACA GTCATAAGTG CGGCGACGAT AGTCATGCCC CGCGCCCACC
 601 GGAAGGAGCT GACTGGGTTG AAGGCTCTCA GGGCATCGG TCGACGCTCT
 651 CCCTTATGCG ACTCCTGCAT TAGGAAGCAG CCCAGTAGTA GGTTGAGGCC
 701 GTTGAGCACC GCCGCCGCAA GGAATGGTGC ATGCAAGGAG ATGGCGCCCA
 751 ACAGTCCCCC GGCCACGGGG CCTGCCACCA TACCCACGCC GAAACAAGCG
 801 CTCATGAGCC CGAAGTGGCG AGCCCGATCT TCCCCATCGG TGATGTCGGC
 851 GATATAGGCG CCAGCAACCG CACCTGTGGC GCCGGTGATG CCGGCCACGA
 901 TGCGTCCGGC GTAGAGGATC CACAGGACGG GTGTGGTCGC CATGATCGCG
 951 TAGTCGATAG TGGCTCCAAG TAGCGAAGCG AGCAGGACTG GGCGGCGGCC
1001 AAAGCGGTCG GACAGTGCTC CGAGAACGGG TGCGCATAGA AATTGCATCA
1051 ACGCATATAG CGCTAGCAGC ACGCCATAGT GACTGGCGAT GCTGTCGGAA
1101 TGGACGATAT CCCGCAAGAG GCCCGGCAGT ACCGGCATAA CCAAGCCTAT
1151 GCCTACAGCA TCCAGGGTGA CGGTGCCGAG GATGACGATG AGCGCATTGT
1201 TAGATTTCAT ACACGGTGCC TGACTGCGTT AGCAATTTAA CTGTGATAAA
1251 CTACCGCATT AAAGCTTATC GATGATAAGC TGTCAAACAT GAGAATTCTT
1301 GAAGACGAAA GGGCCTCGTG ATACGCCTAT TACTAGT
```

PRODUCTION OF THE LANTIBIOTIC CINNAMYCIN WITH GENES ISOLATED FROM *STREPTOMYCES CINNAMONEUS*

The present invention relates to materials and methods for the production of the lantibiotic cinnamycin and modified versions thereof.

Lantibiotics are peptides having antibiotic activity, produced by Gram-positive bacteria. They contain, among other modified residues, the thioether amino acids lanthionine and methyllanthionine, which cross-link the peptide chain into a polycyclic structure. They have been classified into two classes, type-A and type-B, though such classification is not unproblematic. Type-A lantibiotics are generally elongate amphiphiles that are capable of forming pores in bacterial and other plasma membranes. Examples are nisin and subtilin. Type-B lantibiotics, by contrast, are globular, conformationally defined peptides that inhibit enzyme functions. Examples are cinnamycin and duramycin.

Activities ascribed to type-B lantibiotics such as cinnamycin include antimicrobial activity (providing potential application as antibiotics), inhibition of angiotensin-converting enzyme (providing a potential application in blood pressure regulation), immunomodulation via inhibition of phospholipase A2 (providing a potential application as anti-inflammatories), and interference with prostaglandin and leucotriene biosynthesis.

Type-B lantibiotics appear to exert their activity by interfering with enzyme activities by blocking the respective substrates. For example, they have been found to inhibit biosynthesis of peptidoglycan; transglycosylation was identified as the target reaction. The substrate for this reaction is the lipid-bound cell wall precursor lipid II. While this is a target for the antibiotic vancomycin, the site of action is different and is a new target binding site not used by any current antibacterial drug.

Antibacterial activity has been observed, in particular with *Bacillus* strains, with effects described on membrane functions, ATP-dependent proton translocation and $Ca^{2+}$-uptake, and on ATPases. Also, the formation of defined pores in phosphatidylethanolamine-containing planar membranes has been reported. These effects can be attributed to the specific binding of type-B lantibiotics to phosphatidylethanolamine.

Lantibiotics have been shown to have efficacy and utility as food additives and antibacterial agents against *Propionibacterium acnes* and problematic pathogens, e.g. methicillin-resistant *Staphylococcus aureus* (MRSA), which has or is developing resistance to many commonly used antibiotics, and *Streptococcus pneumoniae*.

For reviews, see Sahl and Bierbaum (1998) Annu. Rev. Microbiol. 52:41–79; Jack and Sahl (1995) TIBTECH 13:269–278; Gasson (1995) Chapter 10, Lantibiotics, in Vining and Stuttard (eds) Biotechnology Series: Genetics and Biochemistry of Antibiotic Production, Biotechnological Series 28, pages 283–306.

Accordingly, methods of producing lantibiotics, and the production of variant forms of lantibiotics (which may show improvements over native forms), are highly desirable.

The present inventors have, it is believed for the first time, cloned, sequenced and elucidated structural and regulatory information about the biosynthetic gene cluster for the type-B lantibiotic, cinnamycin, from *Streptomyces cinnamoneus* DSM 40005. A plasmid (pDWFT9) comprising a 17 kb DNA segment from this cluster was introduced into a Streptomycete non-producer of cinnamycin (*Streptomyces lividans*) and conferred the ability to produce cinnamycin. The inventors also propose a minimal set of genes which would be capable of conferring cinnamycin production, and methods for producing variant strains from cinnamycin-producing strains, which variants may produce other novel lantibiotics.

Although the biosynthetic gene cluster for another B-type lantibiotic (mersacidin) has been reported, homology between the mersacidin biosynthetic gene cluster and that reported herein occurs only in one gene (denoted herein as cinM) and is at very low levels.

The 17 kb segment is therefore sufficient to confer upon *S. lividans* the ability to produce cinnamycin. However, the inventors propose that the segment also comprises genes that are non-essential for this function. Apart from cinA, the cinnamycin structural gene (which has already been described in the literature), none of the other gene sequences necessary for the production of cinnamycin have previously been elucidated. Such genes are proposed herein. Moreover, the predicted gene cinR1 is the key to identifying those genes on pDWFT9 that the inventors propose to be responsible for the normal regulation of cinnamycin production.

The predicted gene cinR1 is a member of a family of transcriptional regulators call the Streptomyces antibiotic regulatory proteins (SARPs). This is the first time the production of a lantibiotic has been reported to be under the control of a SARP (notably the mersacidin gene cluster does not appear to be regulated by a SARP). This family of regulators bind to DNA at specific nucleotide sites. These sites are characterised by repeated conserved motifs of 5 or 6 or 7 bases, repeated at multiples of 11 bases (counting from the first base of each motif). The consensus sequence for the SARP binding sites in the cinnamycin and duramycin biosynthetc clusters is TGAAA (which forms part of an 11 base TGAAANNNNNN repeat unit, where N is any base). The final motif is typically followed by a −10 RNA-polymerase promoter site (the consensus sequence being TAGTGT) at some multiple of 11+5 or 6 bases (e.g. 5, 6, 16, 17, 27, 28, 38 or 39 bases). This has the effect of positioning the conserved motifs on one face of the helix and the −10 promoter site on the opposite side. Inspecting the sequence of FIG. 4 (which shows the 17 kb segment), a single site conforming to this model can be found upstream of an open reading frame designated cinorf7. The site consists of 3 pentamers of TGAAA, separated by 6 bases, followed by the potential −10 promoter sequence TAGTGT.

There are seven co-directional genes downstream of this site, designated cinorf7, cinA, cinM, cinX, CinT, cinH and cinY, that appear to form a single operon. From this, the inventors propose that they are all involved in cinnamycin production or regulation.

The cinA gene has previously been reported as the cinnamycin structural gene (Kaletta et al. (1991) Eur. J. Biochem. 199(2):411–415).

The cinM gene, by homology to known proteins, is thought to encode the protein responsible for post-translationally modifying the translation product of the cinA gene to introduce the lanthionine residues of mature cinnamycin. However, the level of homology with the equivalent gene (mrsM) in the mersacidin biosynthetic gene cluster, which is the only other B-type biosynthetic gene cluster currently known to have been determined, is very weak. The experiments reported herein show cinM to be essential for cinnamycin production.

The cinT and cinH genes are proposed to encode an ABC-cassette transporter, responsible for the export of pre-cinnamycin from the bacterial cell.

The cinX and cinY genes are proposed to be involved in the maturation of pre-cinnamycin (i.e. cleavage of the leader sequence) and/or the introduction of the non-lanthionine modifications of cinnamycin (i.e. a lysino-alanine ring and an hydroxy-aspartate residue). Specifically, cinX is proposed to be responsible for the post-translational modification of the cinnamycin propeptide by the addition of an oxygen atom to the aspartate residue to form beta-hydroxy aspartate. The experiments reported herein indicate that functional deletion of the cinX gene leads to a product having a $M_w$ of 2023, compared with 2039 for cinnamycin. Interestingly, this product also shows antibacterial activity, indicating that while cinX may be necessary for cinnamycin production, it may not be essential for the production of variants having one or more activities of lantibiotics.

The cinorf8 predicted gene product is thought to comprise a CoA binding motif, and is thought to be involved in the modification of a cinnamycin intermediate by the attachment/removal of CoA to/from the aspartate residue in the procinnamycin sequence.

The cinorf7 predicted gene product may represent a separate quorum-sensing peptide responsible, in part, for the regulation of cinnamycin production. The experiments reported herein indicate that this gene is not essential for cinnamycin production. In the context of the cinnamycin biosynthetic fragment used herein, however, cinorf7 appears to be essential for high level expression of cinnamycin. This supports its putative regulatory role.

The regulation of the predicted SARP gene (cinR1) is thought to be mediated by the two-component system represented by the predicted genes cinK and cinR which may react to the product of cinorf7.

From this, it is proposed that a cassette comprising fewer genes than the 17 kb segment may also confer cinnamycin production on non-producer strains such as S. lividans.

In particular, it is proposed that a cassette comprising the cinA, cinM, cinX, cinT, cinH, cinY genes may also confer cinnamycin production on non-producer strains.

However, as indicated above, functional deletion of the cinX gene confers production of a lantibiotic slightly different from cinnamycin. This component of the cassette may therefore be considered optional.

Such a cassette would not, it is proposed, be able to regulate cinnamycin production as in producer strains. A preferred cassette therefore also comprises the SARP binding site and the cinorf7, cinR, cinK and cinR1 genes.

Accordingly, the present invention provides in a first aspect an expression cassette comprising a cinA open reading frame (orf), a cinM orf, optionally a cinX orf, a cinT orf, a cinH orf and a cinY orf.

Such a construct represents the minimal expression cassette which may be predicted by the above model to lead to lantibiotic expression.

Preferably the orfs are provided on a single expression cassette, but it is contemplated that they may be provided separately, for example on two vectors which may be co-introduced into a desired host.

Accordingly in this first aspect, the present invention also provides a set of nucleic acids together comprising a cinA orf, a cinM orf, optionally a cinX orf, a cinT orf, a cinH orf and a cinY orf.

Preferably the set is an isolated set of nucleic acids.

Preferably the cassette or set further comprises a SARP binding site, a cinorf7 orf, a cinR orf, a cinK orf and a cinR1 orf. These are thought to regulate cinnamycin production in producer strains, to provide expression at high cell density. The SARP binding site is preferably upstream of the cinorf7 orf, which preferably forms an operon with the cinA, cinM, cinX, cinT, cinH and cinY orfs.

Preferably the expression cassette or set further comprises one or more of the following orfs, which may also be important for cinnamycin production in producer strains: cinorf3, cinorf4, smallorf, cinZ, cinorf8, cinorf9, cinorf10, cinorf11, cinorf12, cinorf13 and cinorf14.

Of these, cinorf3, cinorf13 and cinorf14 in particular are thought not to be essential for cinnamycin (or other lantibiotic) production. cinorf4 and cinorf12 are also thought to be inessential.

Therefore, of the orfs listed above (namely cinorf3, cinorf4, smallorf, cinZ, cinorf8, cinorf9, cinorf10, cinorf11, cinorf12, cinorf13 and cinorf14) one or more (more preferably all) of smallorf, cinZ, cinorf8, cinorf9, cinorf10 and cinorf11 may be included in preferred embodiments of the invention. Of these, preferably cinorf8 and/or cinorfZ are particularly preferred. One or more (preferably all) of cinorf3, cinorf13 and cinorf14 may be absent from, or functionally deleted in, preferred embodiments. Similarly cinorf4 and/or (preferably and) cinorf12 may be absent from, or functionally deleted in, preferred embodiments.

Preferably the cinA orf, for example, has a nucleic acid sequence which encodes a polypeptide having the amino acid sequence which is identical to, or a variant (as further defined below) of, the amino acid sequence of naturally occurring CinA, as set out in FIG. 11.

Preferably the cinA orf has a nucleic acid sequence which is identical to, or a variant (as further defined below) of, the nucleic acid sequence of the cinA orf of the 17 kb segment, as set out in FIG. 4. As indicated in the legend for FIG. 4, the cinA orf runs from base 1671 to base 1907.

The preceding two paragraphs apply mutatis mutandis (and independently) to the other orfs referred to herein. Amino acid sequences for all orfs are given in FIGS. 7 to 27 and the nucleic acid sequence of the 17 kb segment is given in FIG. 4, the legend for which lists the bases at which each orf starts and ends.

In relation to cinA, preferred variants encode CinA variants in which one or more amino acids in the propeptide sequence of CinA is replaced with the amino acid found in the corresponding position in the propeptide sequence of another B-type lantibiotic, especially a similar B-type lantibiotic such as duramycin A, B or C or ancovenin. Combinations of replacements are also contemplated, i.e. one or more amino acids being replaced with the amino acid(s) found in the corresponding positions in the propeptide sequence of one other B-type lantibiotic, and one or more amino acids being replaced with the amino acid(s) found in the corresponding positions in the propeptide sequence of a second or further other B-type lantibiotic.

The propeptide sequence of CinA is shown below, as are the residues in duramycin A, B and C and ancovenin which differ from the propeptide sequence of cinnamycin.

|  | 5 | 10 | 15 | 19 |
|---|---|---|---|---|
|  | ↓ | ↓ | ↓ | ↓ |
| Cinnamycin: | CRQSC | SFGPF | TFVCD | GNTK |
| Duramycin A: | K |  |  |  |
| Duramycin B: |  | L |  |  |
| Duramycin C: | AN | Y L | WS |  |
| Ancovenin: | V |  L | WS |  |

However, the variants of cinA may (additionally or alternatively) comprise other differences to those corresponding to other known B-type lantibiotics. Again, preferred differences are in the propeptide sequence, preferably in one or more of positions 2, 3, 7, 10, 12 and 13 of the propeptide sequence (i.e. the sites which differ between cinnamycin, duramycin A, B and C and ancovenin).

The expression cassette or set will usually further comprise regulatory sequences suitable for directing transcription and translation in a host cell of the orfs present in the cassette. However, a set of nucleic acids may for example be provided without such regulatory sequences, but may be associated with regulatory sequences for expression in a host cell.

Particularly for embodiments lacking the cinR, cinK, cinR1 and/or cinorf7 orfs and/or the SARP binding site, the regulatory sequences may be heterologous to the 17 kb segment, e.g. constitutive promoters for expression in a host cell. However, in preferred embodiments which include those orfs and the SARP binding site, the regulatory sequences may be identical to or variants of those present in th 17 kb segment. In particular, the cassette or set preferably includes: a regulatory sequence upstream of the cinorf7 orf, which sequence includes the SARP binding site, or a variant thereof; a. regulatory sequence upstream of the cinK orf (when present); and a regulatory sequence upstream of the cinR1 orf (when present). The other orfs may be transcribed by readthrough from these orfs, but may require further regulatory sequences, e.g. comprising ribosome binding sites. These regulatory sequences may correspond to the intergenic sequences of the 17 kb segment (or variants).

A preferred regulatory sequence for the cinorf7 orf may comprise some or all of bases 1199 to 1266 of FIG. 4, or a variant thereof, and especially may comprise bases 1185 to 1228 of FIG. 4, or a variant thereof. The latter sequence comprises the SARP binding site and ribosome binding site present in the 17 kb segment. In an alternative or further definition, the regulatory sequences preferably comprises the consensus sequences identified herein, more preferably in substantially the same relationship to each other and the start of the cinorf7 orf as indicated herein.

A preferred regulatory sequence for the cinK orf may comprise some or all of the complement of bases 13256 to 12823 of FIG. 4, or a variant thereof.

A preferred regulatory sequence for the cinR1 orf may comprise some or all of the complement of bases 15380 to 15161 of FIG. 4, or a variant thereof.

As indicated above, it is also contemplated that other regulatory sequences may be used in conjunction with the nucleic acid sequences identified herein. For example, an expression cassette or set of nucleic acids which lacks the proposed SARP-related regulatory structures identified above (namely the SARP binding site, cinorf7, cinR, cinK and cinR1 genes) might contain genes under the control of a constitutive or inducible promoter. See e.g. Kieser et al (2000) Practical *Streptomyces* Genetics, The John Innes Foundation for details of such promoters.

Certain of the orfs identified herein appear to be translationally coupled, that is the stop codon of one orf overlaps with the start codon of a co-transcribed orf. It is thought that a ribosome can translate both such orfs stoichiometrically, without requiring a separate ribosome binding site for the second orf.

Preliminary results (not included herein) indicate that a cassette comprising only the cinA, cinM and cinX genes is capable of conferring low levels of cinnamycin production. It is therefore considered that a minimal cassette or set comprising only a cinA orf, a cinM orf and optionally a cinX orf will confer lantibiotic production. Such a cassette or set is also considered to be within this aspect of the invention. Preferred features are as defined above.

In a second aspect, the present invention provides a vector comprising an expression cassette according to the first aspect of the invention. Further it provides a set of vectors comprising a set of nucleic acids according to the first aspect of the invention.

Suitable vectors comprising nucleic acid for introduction into bacteria can be chosen or constructed, containing appropriate additional regulatory elements if necessary, including additional promoters, terminator fragments, enhancer elements, marker genes and other elements as appropriate. Vectors may be plasmids, viral, such as for example a phage or phagemid, as appropriate. For further details see, for example, Sambrook et al (1989) Molecular Cloning, A Laboratory Manual, 2nd ed., Cold Spring Harbor Laboratory Press, Cold Spring Harbor. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. (1995) Current Protocols in Molecular Biology, Wiley Interscience Publishers, (1995). Many aspects of the employment of these techniques in the context of *Streptomyces* spp. are described in detail in Hopwood et al (1985) Genetic manipulation of *Streptomyces* a laboratory manual (Norwich: John Innes Foundation) and Kieser et al (2000). The disclosures of Sambrook et al, Ausubel et al, Hopwood et al and Kieser et al are all incorporated herein by reference for these and all other purposes In a third aspect, the present invention provides an expression system comprising an expression cassette or set of nucleic acids according to the first aspect of the invention and an expression system comprising a vector or set of vectors according to the second aspect of the invention.

Preferably the expression system is a host cell or cell culture, although cell-free expression systems are also contemplated. Preferably the host cell or culture is bacterial, more preferably actinomycete, further preferably streptomycete, e.g. *S. lividans* or *S. coelicolor* A3(2), especially *S. lividans*.

The introduction of the expression cassette, set of nucleic acids or vector(s) into a host cell, which may (particularly for in vitro introduction) be generally referred to without limitation as transformation, may employ any available technique. For bacterial cells, suitable techniques may include calcium chloride transformation, polyethyleneglycol assisted transformation, electroporation, conjugation and transfection or transduction using bacteriophages.

In a fourth aspect, the present invention provides a method of expressing nucleic acid of interest, the method comprising providing a host cell (or other expression system) according to the third aspect and culturing the host cell, so as to express the nucleic acid of interest.

For the avoidance of doubt, the nucleic acid of interest will be the expression cassette or set of nucleic acids of the first aspect, such that culturing the host cell will lead to the production of cinnamycin, or a variant thereof (for example deoxycinnamycin, in which the aspartate residue has not been post-translationally converted by the CinX gene product into beta-hydroxy aspartate, or the products of the expression of variant forms of cinA, with or without cinX).

Preferably the nucleic acid of interest is expressed substantially only when the host cell culture reaches high cell density, more preferably at or close to the stationary phase of host cell culture. Cell cultures at or close to stationary phase may have $OD_{650}$ values in the range of 1–20.

Known methods of culturing cells are well known in the art, for example from Sambrook et al (1989), Ausubel et al (1992), and (in particular for *Streptomyces* spp.) Hopwood et al (1985) and Kieser et al (2000).

The expression products of the expression systems may be collected and purified. This may be achieved by conventional methods. See for example McDaniel et al. (1993).

In a fifth aspect, therefore, the present invention provides an expression product produced according to the method of the fourth aspect of the invention.

In a sixth aspect, the present invention provides a nucleic acid molecule consisting essentially of one or more of the following orfs: cinorf3, cinorf4, smallorf, cinorf7, cinA, cinM, cinX, cinT, cinH, cinY, cinZ, cinorf8, cinorf9, cinR, cinK, cinorf10, cinorf11, cinR1, cinorf12, cinorf13 and cinorf14, optionally with a regulatory region or regulatory regions. Where present, the regulatory region(s) may comprise promoter sequence(s) for the orf(s). Where two or more orfs are present, a regulatory region for one or more of those orfs may be provided between orfs.

The orfs may be as previously defined.

In relation to cinorf3 and cinorf14, which are disclosed herein in incomplete form, the skilled person will be readily able to obtain the full length orf using known techniques.

In a seventh aspect, the present invention provides the use of one or more nucleic acid molecules as defined in the sixth aspect, in or for the production of a lantibiotic in an expression system.

In an eighth aspect, the present invention provides a polypeptide encodable by one of the following orfs: cinorf3, cinorf4, smallorf, cinorf7, cinA, cinM, cinX, cinT, cinH, cinY, cinZ, cinorf8, cinorf9, cinR, cinK, cinorf10, cinorf11, cinR1, cinorf12, cinorf13 and cinorf14. Preferably the polypeptide is substantially isolated from other proteins with which it is naturally associated.

The polypeptide preferably has an amino acid sequence as shown in one of FIGS. 7 to 27. However, this aspect also provides polypeptides which are variants of those amino acid sequences.

In a ninth aspect, the present invention provides a vector including a nucleic acid according to the sixth aspect. In embodiments in which the nucleic acid lacks a promoter or promoters for the orf(s) it contains, the vector preferably includes a promoter in operative association with the orf(s).

In a tenth aspect, the present invention provides an expression system containing one or more nucleic acids according to the sixth aspect and an expression system containing a vector according to the ninth aspect.

Preferably the expression system is a cell. Any appropriate cell may be used (e.g. a standard *E. coli* overexpression system). See for example Sambrook et al (1989) and Ausubel et al (1992). However, bacterial, actinomycete and streptomycete cells are preferred as previously indicated.

In an eleventh aspect, the present invention provides a method of producing a polypeptide according to the eighth aspect, the method comprising producing the polypeptide in an expression system according to the tenth aspect.

The polypeptide may be purified from the expression system by conventional methods.

As has been demonstrated previously (Sahl and Bierbaum 1998), the proteins which are involved in post-translational processing and modification of lantibiotics (e.g. to introduce lanthionine and/or methyllanthionine residues) may be used in vitro to modify other proteins (especially other lantibiotics). See for example the reviews cited in the introduction and references cited therein. It is proposed that such use may be made of one or more of the polypeptides above, especially CinM, CinX and/or CinY. Indeed, in the experiments described herein, the cinA gene on the pDWFT9 plasmid was modified to encode a polypeptide having the propeptide sequence of duramycin A or B instead of cinnamycin structural gene. This still led to an antibacterially active product, indicating that post-translational modification was occurring despite the change in propeptide sequence.

The inventors also propose that the materials and methods of the present invention be modified, e.g. to produce variant forms of cinnamycin and/or to affect the production of cinnamycin or variants. In particular, it is contemplated that the mutation of one or more orfs or regulatory sequences of the 17 kb segment may lead to changes of this sort. For example, non-silent mutations in the cinA orf will produce changes in the amino acid sequence encoded by the orf, which changes may lead to a variant form of cinnamycin having one or more different properties compared to naturally occurring cinnamycin. Such modification has been demonstrated herein and is particularly preferred. Similarly, mutations of the orfs encoding proteins thought to be responsible for the post-translational modification of the primary transcript of cinA may lead to different post-translational modifications. Mutation of the regulatory sequences may lead to differences in the control of cinnamycin (or variant) production. Such modified materials and methods are also included within the scope of the preceding aspects.

Mutagenesis may be performed using available methods e.g. chemical mutagenesis, alanine-scanning mutagenesis, site-directed mutagenesis using oligonucleotides, error-prone PCR or by propagating target nucleic acid in an appropriate plasmid in a mutator strain, e.g. the XL1-Red strain of *E. coli* (Stratagene). The protocol for this procedure is described in Greener and Callahan (1993) Strategies 6, 32–34. Mutagenesis may be carried out on a particular orf or group of orfs (or regulatory seqence(s)), which is then cloned back into a nucleic acid containing unmutated sequence, or the entire nucleic acid of interest (e.g. the 17 kb segment) may be subjected to mutagenesis.

In particular, the methods and materials of the present invention, relating to the cinnamycin biosynthetic cluster, may be used in conjunction with material derived from other lantibiotic-producing strains, e.g. to expose primary translation products of other lantibiotics (such as other B-type lantibiotics, e.g. duramycin) to the post-translational modification enzymes of the present invention or vice versa. This could be done in vitro, using the translation products, or in vivo, e.g. by introducing the structural gene for another lantibiotic into a host cell having other genes of the cinnamycin biosynthetic pathway.

In a further aspect, the present invention provides a method for producing a library of lantibiotic-producing host cells, the method comprising:

providing a plurality of host cells respectively transformed with different nucleic acids, sets of nucleic acids, vectors or sets of vectors as defined in the first or second aspects.

Preferably at least some of the nucleic acids, sets of nucleic acids, vectors or sets of vectors differ in the propeptide-encoding region of cinA. However, other mutations are contemplated.

In this aspect, there is also provided such a library of lantibiotic-producing host cells, preferably produced or producible according to the method of this aspect.

Such a library may be screened for desirable properties. Preferably it is initially screened for lantibiotic production (e.g. by determining the effect on *B. subtilis* growth), and then screened for interesting and/or advantageous mutations.

The library may be limited, e.g. following such an initial screening step, to host cells which display lantibiotic production.

In a further aspect, the invention provides a method of producing a library of lantibiotics, the method comprising:
providing a library of lantibiotic-producing host cells according to the previous aspect; and
culturing said host cells under conditions suitable for lantibiotic production.

The method may include one or more steps of purifying the lantibiotics thus produced.

This aspect also provides such a library of lantibiotics, preferably produced or producible according to the method of this aspect.

Another aspect of the invention pertains to a composition comprising a lantibiotic produced or producible as provided above and a pharmaceutically acceptable carrier or diluent.

Another aspect of the invention pertains to a lantibiotic produced or producible as provided above for use in a method of treatment of the human or animal body.

Another aspect of the invention pertains to a method of treatment, in vitro or in vivo, comprising contacting a cell with an effective amount of a lantibiotic produced or producible as provided above.

References herein to orfs, genes, coding regions and nucleic acids are not to be interpreted as being restricted to oafs, genes, coding regions and nucleic acids having the specific nucleic acid sequences disclosed herein. Rather, genes, coding regions and nucleic acids having variants of those sequences are also included. Genes, coding regions and nucleic acids having such specific sequences are preferred embodiments. Thus, for example, a reference to a cinA orf is not to be interpreted as being restricted to an orf having the sequence from residue 1671 to 1907 of FIG. 4 but also includes variants.

Similarly, references herein to polypeptides are not to be interpreted as being restricted to polypeptides having the specific amino acid sequences disclosed herein. Rather, polypeptides having variants of those sequences are also included. Polypeptides having such specific sequences are preferred embodiments. Thus, for example, a reference to a CinA polypeptide is not to be interpreted as being restricted to a polypeptide having the amino acid sequence shown in FIG. 11, but also includes variants.

References herein to promoters are not to be interpreted as being restricted to nucleic acids having the sequence of all or part of a specific intergenic region disclosed herein. Again, promoters having variants of those intergenic sequences are also included and the specific intergenic sequences (or parts thereof) are preferred embodiments.

In all cases, where a preferred embodiment of an orf, gene, nucleic acid, polypeptide or promoter is defined by reference to a specific sequence, the invention in its broader sense is intended to include embodiments having variants of that specific sequence. Nevertheless, the specific sequences disclosed herein represent preferred embodiments.

The term variant as used herein in relation to a particular nucleic acid (the reference nucleic acid) denotes: any nucleid acid having a sequence which is different from that of the reference nucleic acid, but which is its complement or which shows significant nucleic acid sequence identity with, or hybridisation under stringent conditions to, the reference nucleic acid or its complement or a fragment of the reference nucleic acid or its complement; or any nucleic acid which encodes an amino acid sequence having significant amino acid sequence identity with the amino acid sequence encoded by the reference nucleic acid, or a fragment of that nucleic acid. The term variant also refers to nucleic acids which differ from each other due only to the degeneracy of the genetic code, and which therefore encode identical deduced amino acid sequences.

The term variant as used herein in relation to a particular polypeptide (the reference polypeptide) denotes: any polypeptide having an amino acid sequence which is different from, but which shows significant amino acid sequence identity with, the amino acid sequence of the reference polypeptide, or a fragment of that polypeptide.

Variant nucleic acids of the invention are further defined as follows. If a variant nucleic acid of the invention is introduced into the 17 kb nucleic acid fragment identified herein in place of the sequence of which it is a variant, and the recombinant fragment is introduced into a suitable host cell under suitable conditions for lantibiotic production (e.g. as shown in the Examples), then production of a molecule having one or more activities of a lantibiotic (especially antibiotic activity) will result. Preferably production will be regulated to occur at high cell density.

Unless otherwise specified, significant amino acid sequence identity is preferably at least 80%, more preferably 85%, 90% or 95%, still more preferably 98% or 99% and/or significant nucleic acid sequence identity is preferably at least 50%, more preferably 60%, 70%, 80% or 90%, still more preferably 95%, 98% or 99%.

Significant amino acid sequence identity is preferably shown between the variant polypeptide (or a portion thereof) and a fragment of at least 10 amino acids of the reference polypeptide, more preferably a fragment of a least 20, 30 or 40 amino acids, still more preferably a fragment of 60, 80 or 100 amino acids, more preferably the entire reference polypeptide.

Significant nucleic acid sequence identity is preferably shown between the variant nucleic acid (or a portion thereof) and a fragment of at least 30 residues of the reference nucleic acid, more preferably a fragment of a least 60, 90 or 120 residues, still more preferably a fragment of 180, 240 or 300 residues, more preferably the entire reference nucleic acid.

A percent (%) amino acid sequence identity" is defined as the percentage of amino acid residues in a candidate sequence that are identical with the amino acid residues in the sequence with which it is being compared, after aligning the sequences and introducing gaps, if necessary, to achieve the maximum percent sequence identity, and not considering any conservative substitutions as part of the sequence identity. The % identity values used herein are generated by WU-BLAST-2 which was obtained from Altschul et al. (1995); blast.wustl/edu/blast/README.html. WU-BLAST-2 uses several search parameters, most of which are set to the default values. The adjustable parameters are set with the following values: overlap span=1, overlap fraction=0.125, word threshold (T)=11. The HSPS and HSPS2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the 'longer' sequence in the aligned region, multiplied by 100. The "longer" sequence is the one having the most actual residues in the aligned region (gaps introduced by WU-BLAST-2 to maximize the alignment score are ignored.

"Percent (%) nucleic acid sequence identity" is defined as the percentage of nucleotide residues in a candidate sequence that are identical with the nucleotide residues in the sequence under comparison. The identity values used herein were generated by the BLASTN module of WU BLAST-2 set to the default parameters, with overlap span and overlap fraction set to 1 and 0.125, respectively.

In relation to variants of the promoters used in the present invention, nucleic acid sequence identity is preferably assessed over a sequence of at least 30 residues, more preferably 40 or 50 residues, still more preferably 60 residues.

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 sodium chloride, 75 mM sodium citrate at 42° C.; or (3) employ 50% formamide, 5×SSC (0.75 m NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1 SDS, and 10% dextran sulfate at 42° C. in 0.2×SSC (sodium chloride/sodium citrate) and 50% formamide at 55° C., followed by a high-stringency wash consisting of 0.1×SSC containing EDTA at 55° C.

When a nucleic acid of interest is an operative association with a promoter or regulatory sequence, the promoter/regulatory sequence is able to direct transcription of the nucleic acid of interest in an appropriate expression system, with, the nucleic acid of interest in the correct reading frame for translation. Preferably when a nucleic acid of interest is in operative association with a promoter/regulatory sequence, the transcript of the nucleic acid of interest contains an appropriately located ribosome binding site for expression in an appropriate expression system of the polypeptide encoded by the nucleic acid of interest. See for example Sambrook et al. (1989) and Ausubel et al. (1995).

When a nucleic acid is referred to as "isolated", this may mean substantially or completely isolated from some or all other nucleic acid normally present in *Streptomyces cinnamoneus cinnamoneus* DSM40005, especially nucleic acid from outside the 17 kb segment identified herein. However, the use of for example a *Streptomyces cinnamoneus cinnamoneus* DSM40005 regulatory sequence with an otherwise isolated nucleic acid is not to be regarded as prevented such nucleic acid from being deemed "isolated". When a polypeptide is referred to as "isolated", this may mean substantially or completely isolated from some or all polypeptides normally expressed by *Streptomyces cinnamoneus cinnamoneus* DSM40005, especially polypeptides encoded by nucleic acid from outside the 17 kb segment identified herein.

Formulations

The lantibiotics of the present invention may be formulated together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g.; wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein. pertains to compounds, ingredients, materials, compositions, dosage forms, etc., which are, within the scope of sound medical judgement, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 2nd edition, 1994.

The experimental basis of the present invention will now be described in detail, by way of example only, with reference to the accompanying drawings, in which:

FIG. 1 shows the DNA sequence of probe CK. In this figure and elsewhere, the base N may represent A, C, G or T (or U for RNA).

FIG. 2 shows the DNA sequence of pDWCC1. The primers BB3 and BB4 are marked in bold and labelled.

FIG. 3 shows the DNA sequence of probe BB.

Figure 5:
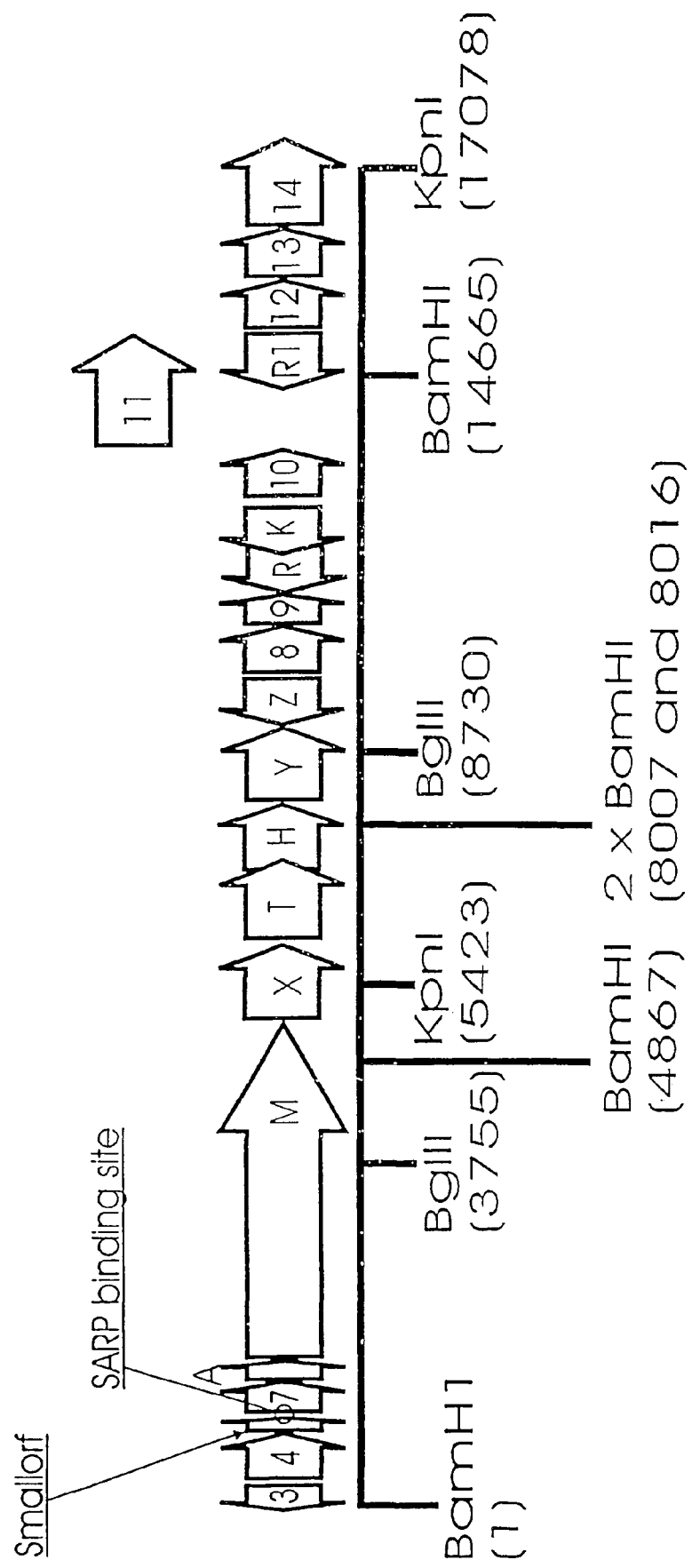

FIG. 4 shows the sequence of the cinnamycin cluster from *Streptomyces cinnamoneus cinnamoneus* 40005 as present on the plasmid pDWFT9. The probable SARP binding site is indicated in bold and the probable −10 promoter site is indicated in bold italics. Open reading frames in the sequence are as follows (the numbers represent the first and last base pairs): cinorf3=complement (346 . . . 1) (NB as this is an incomplete orf, the end of the sequence is not a stop codon); cinorf4=454. . . 1026; smallorf=1109 . . . 1198; cinorf7=1267 . . . 1626; cinA=1671 . . . 1907; cinM=2059 . . . 5325; cinX=5340 . . . 6317; cinT=6543 . . . 7472; cinH=7469 . . . 8341; cinY=8444 . . . 9466; cinZ=complement (10171 . . . 9545); cinorf8=10246 . . . 10665; cinorf9=10758 . . . 11078; cinR=complement (11761 . . . 11111); cinK=complement (12822 . . . 11758); cinorf10=13257 . . . 13754; cinorf11=13754 . . . 14944; cinR1=complement (15160 . . . 14375); cinorf12=15381 . . . 15872; cinorf13=15912 . . . 16496; cinorf14=16549 . . . 17083 (NB as this is an incomplete orf, the end of the sequence is not a stop codon).

FIG. 5 shows the order and orientation of the putative genes of the cinnamycin cluster of *Streptomyces cinnamoneus cinnamoneus* 40005 and also represents all of the *Streptomyces cinnamoneus cinnamoneus* 40005 DNA inserted into pOJ436 to give pDWFT9. The putative genes represented in this diagram as capital letters are prefixed in the text as cin whilst those with numbers are prefixed as cinorf. Restriction sites cut by enzymes used in the cloning process are marked along with the first base-pair position of the relevent recognition site in the sequence given in FIG. 4. This is a schematic diagram and not to scale.

FIG. 6 shows the DNA sequence of probe 1.1.

FIG. 7 shows the deduced amino acid sequence encoded by cinorf3. This is an incomplete orf. The MW is shown.

FIGS. 8 to 26 respectively show the deduced amino acid sequences encoded by each of the orfs from cinorf4 on the left hand side of FIG. 5 to cinorf13 on the right hand side of FIG. 5. The MWs are listed.

FIG. 27 shows the deduced amino acid sequence encoded by cinorf14. This is an incomplete orf. The MW is listed.

FIG. 28 shows the DNA sequence of pCK51.

FIG. 29 shows the DNA sequence of the tetracycline resistance cassette of pDWFT33.

EXAMPLE 1

The Cloning of the Cinnamycin Cluster of *Streptomyces Cinnamoneus Cinnamoneus* DSM 40005

Materials

Plasmid pCK51 (Kaletta C et al (1991) Eur. J. Biochem 199(2): 411–415) carrying the structural gene for cinnamycin (cinA) along with sequence data for this plasmid was obtained from Dr Torsten Helge Stein of the Institut für Mikrobiologie, der Johann Wolgang Goethe-Universität Frankfurt, Biozentrum Niederursel, Marie-Curie-Straβe 9, D-60439 Frankfurt/Main, Germany.

*Streptomyces cinnamoneus cinnamoneus* strains DSM 40646 and DSM 40005 (duramycin and cinnamycin producers respectively) were obtained from the German Collection of Microorgansims, DSM.

*Streptomyces lividans* 1326 and *Escherichia coli* DH5α are common laboratory strains.

Methods

Cloning of the genes for Cinnamycin Production

An approximately 2.8 kb NdeI (see FIG. 28 cut site 2033CA↓TATG)/BamHI (see FIG. 28 cut site 4844G↓GATCC) restriction fragment was isolated from pCK51 by agarose gel electrophoresis using the Qiagen gel extraction kit. This restriction fragment lies downstream of cinA and carries the 5' part of a putative lanM type gene that encodes a protein thought to be involved in the production of lanthionine residues. The restriction fragment was then used to produce a radio-labelled probe (Pharmacia Oligolabelling Kit), probe-CK (see FIG. 1), for use in Southern analysis and colony hybridisations.

Genomic DNA was isolated from *Streptomyces cinnamoneus cinnamoneus* 40646 and cut with a series of restriction endonucleases (Asp718, BamHI, BglII, SacI, SalI, XhoI, and PstI) before being subject to Southern analysis using probe-CK. An approximately 5 kb BglII restriction fragment was obtained that was selected for cloning. Genomic DNA digested with BglII and fragments of about 5 kb in size were isolated by agarose gel electrophoresis and ligated into BamHI cut pBluescriptII KS (Stratagene). The resulting ligation mixture was transformed into *E. coli* DH5α to form a mini-library of BglII fragments of about 5 kb. A clone, pDWCC1 (see FIG. 2), carrying the BglII fragment detected by Southern analysis was isolated from this library by colony hybridisation using probe-CK. Sequencing of pDWCC1 revealed the isolated BglII fragment to be 4943 bp long with one end encoding the 3' end of a lanM type gene corresponding to probe-CK.

Sequence information from pDWCC1 was used to design a probe to the lanM type gene and used in the screening of *Streptomyces cinnamoneus cinnamoneus* DSM 40005 genomic DNA. A DNA fragment was prepared by polymerase chain reaction (PCR) using Taq polymerase. The primers used were BB3 (=5'-GCC TAC GAG GAC CGG TAC GTC G-3', in bold in FIG. 2 start 1050 stop 1071) and BB4 (=5'-GGC GAA GCG CAG GAA GAG CTC G-3', complement in bold in FIG. 2 start 1343 stop 1322) and a fragment of 294 bp in length was produced. This PCR fragment was used to produce a radiolabelled probe, probe-BB (see FIG. 3) and used in Southern analysis and colony hybridisation.

Genomic DNA was isolated from *Streptomyces cinnamoneus cinnamoneus* DSM 40005 and cut with a series of restriction endonucleases (BamHI, BglII, SacI, SalI, XhoI, and PstI) before being subject to Southern analysis using probe-BB. An approximately 5 kb BglII restriction fragment was obtained that was selected for cloning. Genomic DNA was digested with BglII and fragments of about 5 kb were isolated by agarose gel electrophoresis and ligated into BamHI cut pBluescriptII KS (Stratagene). The ligation mixture was transformed into *E. coli* DH5α to form a mini-library of BglII fragments of about 5 kb. Two clones, pDWFT1 and pDWFT2 (the sequences of which correspond to that starting at position 3756 and stopping at position 8734 of FIG. 4) carrying the BglII fragment detected by Southern analysis were isolated from this library by colony hybridisation using probe-BB. These two plasmids were subsequently shown to contain identical inserts in opposite orientations by sequencing with pBluescriptII KS reverse primer (Stratagene). Sequencing of pDWFT1 revealed the isolated BglII fragment to be 4979 bp long (see FIG. 4 and 5) with one end encoding the 3' part of a lanM type gene corresponding to probe-BB. Computer analysis of the sequence data for pDWCC1 and pDWFT1 revealed the two BglII fragments to be 88.8% identical along the entire lengths of both fragments. Subsequently an approximately 5 kb BamHI fragment, which was also detected by Southern analysis using probe-BB, was cloned in a similar procedure to give pDWFT4 (the sequence of which corresponds to that starting at position 1 and stopping at position 4872 of FIG. 4).

Sequencing of pDWFT4 revealed the BamHI fragment to be 4872 bp in length (see FIGS. 4 and 5) and carries the 5' end of the lanM type gene and cinA. Comparison of the sequence data for the BamHI fragments of pDWFT4 and the sequence data provided for pCK51 showed the two fragments to be 97.3% identical along the entire lengths of both fragments.

A PstI fragment of approximately 1.1 Kb from the end of the BglII fragment of pDWFT2 distal to the end carrying the lanM type gene was isolated by agarose gel electrophoresis (This corresponds to the region starting at position 7612 and stopping at position 8734 of the sequence shown in FIG. 4 plus a short length of the pBluescriptII KS poly-linker (see FIG. 6)). This fragment was then used to prepare a radio-labelled probe, probe-1.1 (see FIG. 6) for use in Southern analysis and colony hybridisations. Using probe-1.1 an approximately 11 kb Asp718 fragment from *Streptomyces cinnamoneus cinnamoneus* DSM 40005 genomic DNA was obtained by Southern analysis. This fragment was then isolated and cloned using probe-1.1 in a procedure similar to that described for pDWCC1 to give pDWFT5 (The sequence of which corresponds to the region starting at position 5423 and stopping at position 17083). Sequencing of this plasmid revealed it to be 11661 bp in length with a 3312 bp overlap with pDWFT1 (see FIGS. 4 and 5).

The cloned fragments from pDWFT1, pDWFT4 and pDWFT5 were then cloned together to give a single piece of DNA, pDWFT9 (see FIGS. 4 and 5), with the various parts in the same order and orientations as in the *Streptomyces* cinnamoneus cinnamoneus DSM 40005 chromosome. Analysis of the sequence data (using the Wisconsin GCG package Version 10.1-Unix: gap creation penalty 50; gap extension penalty 3) for these three plasmids shows that they cover a single 17083 bp region of the *Streptomyces cinnamoneus cinnamoneus* DSM 40005 genome. The sequence data revealed that there were only two Asp718 sites (GGTACC) within this region. One of these sites is within the region covered by pDWFT1 and corresponds to one end of the Asp718 fragment of pDWFT5 whilst the other is at the other end of the region covered by pDWFT5. The region of pDWFT1 not overlapped by either pDWFT4 or pDWFT5 corresponds to a single 562 bp long BamHI/Asp718 fragment. The BamHI fragment of pDWFT4 was ligated together with the 562 bp BamHI/Asp718 fragment of pDWFT1 to restore one end of the cluster to the wild type conformation. Subsequently the Asp718 fragment of pDWFT5 was ligated to this to restore the whole cluster to the wild type conformation.

The first step in this process was to clone the 562 bp BamHI (see FIG. 4 cut site 4867G↓GATCC)/Asp718 (see FIG. 4 cut site 5423G↓GTACC) fragment from pDWFT1 into pBluescriptII KS cut with BamHI/Asp718 to give pDWFT6. The cloned 5 kb BamHI fragment from pDWFT4 (see FIG. 4 cut sites 1G↓GATCC and 4867G↓GATCC) was then cloned into BamHI cut pDWFT6 to give pDWFT7. The orientation of the fragments in pDWFT7 was checked by restriction analysis using standard procedures (Sambrooke J et al (1989) Molecular Cloning; A Laboratory Manual, Cold Spring Harbor Laboratory Press Chapter 1 and Chapter 6) to ensure that it conformed to the native conformation. This BamHI/BamHI/Asp718 fragment was then cut from pDWFT7 on a single Asp718/XbaI fragment (the sequence of which corresponds to the region starting at position 1 and stopping at position 5428 plus a short region of pBluescriptII KS poly-linker) and cloned into pQJ436 (Bierman M et al (1992) Gene 116, pp 43–49) to give pDWFT8. The Asp718 fragment from pDWFT5 (see FIG. 4 cut sites 5423G↓GTACC and 17078G↓GTACC) was cloned into pDWFT8 cut with Asp718 to give pDWFT9. The orientation of the fragments was checked by restriction analysis with BglII to ensure that the fragment corresponding to the BglII fragment of pDWFT1 had been restored. This plasmid pDWFT9 is composed of 17083 bp of DNA corresponding exactly to the sequence of the *Streptomyces cinnamoneus cinnamoneus* DSM 40005 chromosome, plus a small region of pBluescriptII KS poly-linker, cloned into pOJ436.

*Streptomyces lividans* 1326 was then transformed with pDWFT9 and also the basic vector pOJ436 to produce test and control strains, respectively. Those strains possessing pDWFT9 were labelled *S. lividans* DW9a-1-8 and those possessing pOJ436 were labelled *S. lividans* DW436-1-4.

Bioassays for Cinnamycin Production

The strains tested, DW9a1-8 and DW436-1-4, were grown for 5–7 days on R2YE medium (Practical *Streptomyces* Genetics (2000) Kieser T. et al The John Innes Foundation p. 408). An over-night culture of *B. subtilis* was used to inoculate a 10 ml LB media culture which was grown until its OD=0.3–0.4 (600 nm) (between 5–8 hours). A 0.5 ml aliquot of this culture was then used to inoculate 5 ml of soft Oxoid nutrient agar at 55° C. which was mixed by inversion and then poured immediately over the plate to be assayed. The plate tilted until an even covering of the *B. subtilis* overlay was achieved. The assay plate was then grown at 37° C. over-night after which it was checked for inhibition of the growth of *B. subtilis*.

Detection of Cinnamycin by Mass Spectrometry

*Streptomyces lividans* strains were grown for 5–7 days in either YEME or TSB medium (Practical Streptomyces supra) after which the cells were removed by centrifugation. The supernatant was then extracted twice with an equal volume of ethyl acetate with the aqueous fraction being retained both times. The aqueous fraction was extracted twice with butanol equilibrated with water, with the butanol fraction being retained and both fractions being pooled. The butanol was then extracted with either 10× or 2× volumes of 10% formic acid which was subsequently used for analysis on a MALDI-TOF mass spectrometer.

Results

Bioassays for Cinnamycin Production

The results in Table 1 show that *S. cinnamoneus cinnamoneus* DSM 40005 inhibits the growth of *B. subtilis* and that strains of *S. lividans* which carry the vector pOJ436 upon which pDWFT9 is based, but which do not carry the putative cinnamycin cluster, do not show any inhibition of the growth of *B. subtilis*. Strains of *S. lividans* carrying the plasmid pDWFT9, which encodes the putative cinnamycin cluster from *S. cinnamoneus cinnamoneus* DSM 40005 inhibit the growth of *B. subtilis*. Since *S. cinnamoneus cinnamoneus* DSM 40005 inhibits the growth of *B. subtilis* and a known activity of cinnamycin is the inhibition of the growth of the *B. subtilis* strains this result provides evidence that the *S. lividans* strains carrying the putative cinnamycin cluster, carried on pDWFT9, are producing cinnamycin.

Detection of Cinnamycin by Mass Spectrometry

The results in Table 2 show that molecules with molecular weights similar to cinnamycin (2039.4 as calculated from propeptide sequence data and structural data) were present in the supernatants of liquid cultures of *Streptomyces cinnamoneus cinnamoneus* DSM 40005 and *S. lividans* DW9a-1, the strain carrying the carrying the putative cinnamycin cluster on plasmid pDWFT9. No molecules with this molecular weight were detected in supernatants of liquid cultures of *S. lividans* DW436-4 which carries pOJ436, the vector upon which pDWFT9 is based but without the cinnamycin cluster. This is taken as evidence that *S. lividans* DW9a-1 which carries the putative cinnamycin cluster is producing cinnamycin.

Analysis of the Sequence of the Cinnamycin Cluster of *Streptomyces cinnamoneus cinnamoneus* DSM 40005

The plasmid pDWFT9 possesses the *Streptomyces cinnamoneus cinnamoneus* DSM 40005 cinnamycin cluster genes that are vital for the expression of cinnamycin in *S. lividans*. The sequence data for this plasmid is represented in FIG. 4 which, together with its legend, also lists the putative genes, and the positions of these genes, along with other vital features encoded within this sequence. The positions of these genes were determined by using the frameplot program (accepting the default values) and, when there was more than one available start codon, looking for a potential ribosome binding site (Shine Dalgarno sequence) taking the sequence GGAGG as the ideal (*Practical Streptomyces Genetics* (2000) Kieser T. et al The John Innes Foundation p. 386). The order and relative orientation of the putative genes is shown in the diagram FIG. 5. The frameplot program is publicly available on the web at http://watson-.nih.go.jp/~jun/cgi-bin/frameplot.pl (Ishikawa, J. and Hotta, K. FEMS Microbiol. Lett. 174:251–253 (1999)). There are 21 potential genes in this sequence which potentially represent real genes and are discussed individually below starting at the beginning of the sequence and going through in the order that they occur. The database search program Blast P, based at the NCBI, was used to look for similarities between the protein translations of the potential genes given here and those in the publicly available database using the version of Blast available at the provided web page.

cinorf3 (FIG. 7). Incomplete predicted gene with the 3' end being truncated.

cinorf4 (FIG. 8) The protein translation product of this predicted gene has no homology with any gene product of known function.

smallorf (FIG. 9) This motif starts at residue 1109 and ends at residue 1198 of FIG. 1.

cinorf7 (FIG. 10) The protein translation product of this predicted gene has no homology to any gene product of known function.

cinA (FIG. 11) This is the cinnamycin structural gene. The protein translation product has 100% identity with the gene product of the published cinA gene (Kaletta C et al (1991) Eur. J. Biochem 199(2): 411–415).

cinM (FIG. 12) The protein translation product of this predicted gene is thought to be a modifying enzyme.

cinX (FIG. 13) The protein translation product of this predicted gene has no homology to any gene product of known function.

cinT (FIG. 14) The protein translation product of this predicted gene appears to be translationally coupled to the translation product of the predicted cinH gene.

cinH (FIG. 15) The protein translation product of this predicted gene appears to be translationally coupled to the translation product of the predicted cinT gene.

cinY (FIG. 16) The protein translation product of this predicted gene has no homology to any gene product of known function.

cinZ (FIG. 17) The protein translation product of this predicted gene has 40% homology over its entire length with the C-terminal third of the PepQ protein from *E. coli* (embl locus ECPEPQ, accession X54687.1).

cinorf8 (FIG. 18) The protein translation product of this predicted gene has greater than 47% identity over its full length with a protein from *E. coli* (pir: locus D64837).

cinorf9 (FIG. 19) The protein translation product of this predicted gene has no homology to any gene product of known function.

cinR (FIG. 20) The protein translation product of this predicted gene has homology over its full length with many putative response regulators from *Streptomyces coelicolor* A3(2). For example, a hit using Blast P (available from the NCBI website at www.ncbi.nlm.nih.gov; word size: 3; matrix: blosum 62; gap costs: existence: 11, extension: 1) recorded 48% identity over the entire length of the putative CinR protein. This correlates with the AbsA2-protein which is thought to be involved in global negative regulation of *Streptomyces coelicolor* antibiotic synthesis (Brian, P., Riggle, P. J., Santos, R. A. and Champness, W. C. J. Bacteriol. 178 (11), 3221–3231 (1996)). This predicted gene appears to be translationally coupled to the predicted cinK gene.

cinK (FIG. 21) The protein translation product of this predicted gene has homology over its entire length with many putative histidine kinases from *Streptomyces coelicolor* A3 (2). For example, a hit using Blast P (default parameters) recorded 34% identity over the entire length of the putative CinK protein. This correlates with the AbsA1 protein which is thought to be involved in global negative regulation of *Streptomyces coelicolor* antibiotic synthesis (Brian, P., Riggle, P. J., Santos, R. A. and Champness, W. C. J. Bacteriol. 178 (11), 3221–3231 (1996)). This predicted gene appears to be translationally coupled to the predicted cinR gene.

cinorf10 (FIG. 22) The protein translation product of this predicted gene has no homology to any gene product of known function. This predicted gene may be translationally coupled to the predicted cinorf11 gene.

cinorf11 (FIG. 23) The protein translation product of this predicted gene has no homology to any gene product of known function. This predicted gene may be translationally coupled to the predicted cinorf10 gene.

cinR1 (FIG. 24) The protein translation product of this predicted gene has 38% identity along its entire length to the N-terminal region of the AfsR-g protein from *Streptomyces griseus* (Umeyama, T., Lee, P. C., Ueda, K. and Horinouchi, S. Microbiology 145 (Pt 9), 2281–2292(1999)) and 38% identity along its entire length to the N-terminal region of the AfsR-g protein from *Streptomyces coelicolor* A3(2) (Horinouchi, S., Kito, M., Nishiyama, M., Furuya, K., Hong, S. K., Miyake, K. and Beppu, T. Gene 95 (1), 49–56 (1990)).

cinorf12 (FIG. 25) The protein translation product of this predicted gene has no homology to any gene product of known function.

cinorf13 (FIG. 26) The protein translation product of this predicted gene has no homology to any gene product of known function.

cinorf14 (FIG. 27) This is not a complete potential gene with the 3' end being truncated. The protein translation product of this predicted gene has no homology to any gene product of known function.

EXAMPLE 2

Construction of a Plasmid Tool for the Production of Artificial Variants of Cinnamycin By the introduction of new restriction sites within and downstream of the cinnamycin structural gene, cinA, it was possible to generate a replaceable cassette which enabled the cinnamycin production process to be harnessed for the production of variants.

The cinA structural gene was encoded on the plasmid pDWFT4 which possesses a 4872 bp BamHI fragment derived from the *Streptomyces cinnamoneus cinnamoneus* DSM 40005 chromosome. Within the BamHI fragment are two unique restriction sites XhoI (see FIG. 4 cut site 1728C↓TCGAG) and NdeI (see FIG. 4 cut site 2056CA↓TATG). The XhoI site lies within the leader peptide encoding region of cinA and the NdeI site lies downstream of the cinA gene. These two sites form a convenient cassette which is replaced by a similar region that is generated by PCR with oligonucleotides incorporating changes to the native sequence so that new restriction sites are made. These new sites are placed either side of the propeptide region of cinA enabling the native propeptide encoding region to be removed and replaced with double stranded oligonucleotides encoding propeptides of choice.

The new restriction sites that have been incorporated are StuI and SpeI. These sites were chosen because there are no StuI or SpeI sites present in the plasmid pDWFT9, described above. This presents an opportunity to construct libraries of variant propeptide regions in this plasmid by replacing the propeptide region with double stranded oligonucleotides that are redundant at specified positions. The restriction site StuI was selected because it can be incorporated without altering the encoded CinA peptide. An A1838G substitution of the pDWFT4 BamHI fragment introduces a StuI site, exchanging the GAA codon for a GAG codon (both of which code for glutamate residues). This site is four codons upstream of the first propeptide codon and enable the whole propeptide region to be exchanged. The SpeI site was to be incorporated by making three changes immediately downstream of the cinA stop codon. These changes were G1908C, G1910A and C1912T of the pDWFT4 BamHI fragment. However, the introduction of these changes also incorporated a spontaneous change in the sequence (see below).

The above plan was executed in the following manner. The 4872 bp BamHI fragment of pDWFT4 was subcloned into a vector that does not possess any XhoI, StuI, SpeI or NdeI sites: The plasmid pBlueScriptIIks does not possess either a StuI or a NdeI site but does have XhoI and SpeI sites. The XhoI and SpeI sites of pBluescriptII KS are unique and positioned in the poly-linker region of the plasmid and can be destroyed by cutting with XhoI and end-filling with Klenow fragment polymerase, followed by ligation and isolation of the modified plasmid to give plasmid pNOX. The process is then repeated on pNOX with SpeI to give pNOXS. The plasmid pNOXS was then cut with BamHI and the 4872 bp BamHI fragment of pDWFT4 cloned into it to yielding pDWFT17.

Oligonucleotide primer pairs were made which introduced sequence changes producing either the StuI or the SpeI sites described above. These primers were:

FTP25=5'-CTT CGT GTG CGA CGG CAA CAC C-3' homology with the pDWFT4 BamHI fragment starts at position 1880 and stops at position 1901 of FIG. 4

Spe1=5'-GCA GCA ACT AGT TAC TTG GTG TTG CCG TCG-3' Its homology with the pDWFT4 BamHI fragment starts at position 1889 and stops at position 1918 of FIG. 4

Stu=5'-CCA CGG AGG CCT TCG CCT GCC GCC AGA GCT GC-3' Its homology with the pDWFT4 BamHI fragment starts at position 1831 and stops at position 1862 of FIG. 4

Stu1=5'-GGC GAA GGC CTC CGT GGC GGC GAT GTC CTT GG-3' Its homology with the pDWFT4 BamHI fragment starts at position 1847 and stops at position 1806 of FIG. 4

Xho=5'-TTC AGC AGT CCG TCG TGG ACG-3' Its homology with the pDWFT4 BamHI fragment starts at position 1687 and stops at position 1707 of FIG. 4

Nde=5'-GCG GAT ACG CGT TAC CCA TAC C-3' Its homology with the pDWFT4 BamHI fragment starts at position 2062 and stops at position 2083 of FIG. 4

The StuI site was introduced first by producing PCR fragments using pDWFT4 as a template. The primer pairs Stu and Nde were used with Pfu-polymerase to produce the fragment StuPCR1 using the following reaction conditions: a 50 μl reaction using 1× Pfu-polymerase buffer (Promega) 100 pg template DNA, 200 μM dNTPs, 20 pmol each primer, 5% DMSO and the following thermal cycle: a denaturation step at 94° C. for 3 min followed by 25 cycles with denaturation at 94° C. for 35 s, annealing at 55° C. for 1 min and elongation at 68° C. for 1 min 30 s. A last elongation step was done at 68° C. for 5 min. Subsequently the primer pairs Stu1 and Xho were used with Taq-polymerase to produce the fragment StuPCR2 using similar conditions to those for StuPCR1 but with 1× Taq-buffer and elongation steps carried out at 72° C. These fragments were then purified by agarose gel electrophoresis into 50 μl water. Then 0.5 μl of each PCR fragment were mixed and used as template for a PCR with Pfu polymerase and primer pairs Xho and Nde to produce fragment StuPCR3 using conditions similar to those for StuPCR1 but with only 10 cycles of the thermal cycle. The plasmid pDWFT17 was cut with XhoI and NdeI and purified away from the small fragment that has been released using agarose gel electrophoresis. The PCR product StuPCR3 was then be cut with XhoI and NdeI and ligated into the XhoI/NdeI cut pDWFT17 to generate a new plasmid, pDWFT19, which possesses an StuI site in the position described above as demonstrated by restriction digests with StuI.

The SpeI site was then introduced by producing PCR fragments using pDWFT19 as template. The primer pairs FTP25 and Nde were used with Pfu-polymerase to produce the PCR fragment SpePCR1 (conditions as for StuPCR1) and then primer pairs Spe1 and Xho were used with Pfu-polymerase to produce the PCR fragment SpePCR2 (conditions as for StuPCR1). These fragments were purified by agarose gel electrophoresis and mixed in approximately equimolar amounts then subject to PCR with Pfu-polymerase and primer pairs Xho and Nde to produce the PCR fragment SpePCR3 (conditions as for StuPCR3). This PCR product was then used to replace the region between the XhoI and NdeI restriction sites of pDWFT17. The plasmid pDWFT17 was cut with XhoI and NdeI and purified away from the small fragment that was released -using agarose gel electrophoresis. The PCR product SpePCR3 was cut with XhoI and NdeI and ligated into the XhoI/NdeI cut pDWFT17 to generate a new plasmid, pDWFT21. This plasmid has been shown to possess both the SpeI and StuI restriction sites described above by sequencing, however, the sequence also shows that a 3 bp insert downstream of the SpeI site has been introduced (see FIG. 29).

It was decided to replace the cinA pro-peptide encoding region of pDWFT21 encompassed by the StuI/SpeI sites with a tetracycline resistance cassette. This cassette was over 1 Kb in size and it would, therefore, be easy to identify the fragment of pDWFT21 left by excision of this cassette using StuI/SpeI restriction endonucleases.

The above was achieved by using PCR, with Taq-polymerase, to produce a copy of the tetracycline resistance gene, Tc, from pBR322 with a StuI site immediately downstream of the stop codon and a SpeI 121 bp upstream of the start codon using the following primers:

tet3=5'-GCG GCG AGG CCT CGC CGG CTT CCA TTC AGG tet4=5'-GCG GCG ACT AGT AAT AGG CGT ATC ACG AGG The reaction conditions used to make this PCR fragment were the same as those for StuPCR2. This was then used to replace the StuI/SpeI fragment, encoding the propeptide region of cinA, of pDWFT21 thus generating pDWFT33. This last construct was used to make cinnamycin-derivative constructs.

Large double stranded oligos were made which were variations on the pDWFT21 StuI/SpeI fragment cinA-propeptide encoding region which incorporated changes that resulted in the cinnamycin cluster producing duramycin or duramycinB instead of cinnamycin. These were constructed from 88mer single stranded oligonucleotides (duranA and duranB which encode the propeptide regions for duramycin and duramycinB respectively) that were annealed to a complimentary 20 mer single stranded oligonucleotide (endfill) which was then elongated with pfu-polymerase to produce 88mer double stranded oligonucleotides using conditions similar to those for StuPCR1 but with only one cycle of melting, annealing and elongation. The oligonucleotide sequences were:

```
duranA = 5'-GCG GCG AGG CCT TCG CCT GCA AGC
AGA GCT GCA GCT TCG GCC CGT TCA CCT TCG TGT GCG
ACG GCA ACA CCA AGT AAC TAG TCC GGC C-3' duranB = 5'-GCG GCG AGG CCT TCG CCT GCC GCC AGA
GCT GCA GCT TCG GCC CGC TCA CCT TCG TGT GCG ACG
GCA ACA CCA AGT AAC TAG TCC GGC C-3' endfill = 5'-GGC CGG ACT AGT TAC TTG GT-3'
```

These double stranded oligonucleotides were cleaned by using a Qiagen gel extraction kit by adding 50 μl of sterile distilled water to the 50 μl of reaction mixture then proceeding as though this were a 100 mg gel slice. The double stranded oligonucleotides were eluted from the qiagen column in 40 μl water. They were subsequently digested with StuI and SpeI and used to replace the StuI/SpeI Tc gene fragment of pDWFT33 resulting in two plasmids; pDWFT40 (duranB) and pDWFT42 (duranA). The cinnamycin structural gene cinA was therefore replaced with a duramycin structural gene or a duramycinB structural gene as appropriate and as described above. These plasmids were then used to reconstitute the duramycin equivalents of pDWFT9 in the same manner as pDWFT4. This process resulted in pDWFT52 which carries a duramycinB structural gene and pDWFT54 which carries a duramycin structural gene. These plasmids were then transformed into *S. lividans* 1326. Transformants were selected and the resulting strains, DW52 and DW54 were bioassayed for cinnamycin and cultures grown for MALDI-TOF analysis as described above.

Results

The strains DW52 and DW54, which are predicted to make duramycinB and duramycin respectively, were tested to determine if they could inhibit the growth of *B. subtillis* in bioassays.

The strains DW52 and DWS4 inhibit the growth of *B. subtillis* in bio-assays indicating that they each produce an antibiotic compound. This indicates that the changes to the propeptide encoding region of cinA still allow production of an antibiotic compound by the cinnamycin cluster. See Table 3.

To check that these compounds are duramycinB and duramycin supernatants from liquid cultures were examined using MALDI-TOF mass-spectrometry.

Neither DW52 or DW54 produced a compound with the molecular weight of cinnamycin indicating that the changes in the pro-peptide regions of their respective cinA genes abolished their cinnamycin clusters abilities to produce cinnamycin. However, as predicted from the changes made to their cinA pro-peptide regions, DW52 was able to produce a compound with the expected MW of duramycinB and DW54 was able to produce a compound with the expected MW of duramycin. This indicates that we have successfully engineered the cinnamycin cluster to produce variants of cinnamycin. See Table 4.

EXAMPLE 3

Defining the Roles of Some of the Genes Carried on pDWFT9 in the Cinnamycin Production Cluster The Creation of a Plasmid that Lacks the Genes Upstream of cinorf7 and cinR1

In order to determine if cinorf3, cinorf4, cinorf12, cinorf13 and cinorf14 are involved in the production of cinnamycin a strain was created that lacks all or parts of these genes. In order to facilitate this it was decided to create a version of pDWFT4 wherein the BamHI end upstream of cinorf7 was moved so that cinorf3 and most of cinorf4 was deleted and a version of pDWFT5 was created so the Asp718 end upstream of cinR1 was moved so that cinorf13, cinorf14 and most of cinorf12 were deleted. These two modified plasmids could then be reassembled in a similar manner to that which gave rise to pDWFT9 (described above).

The first step in this process was to generate the variant of pDWFT4. A PCR product was generated using the following two primers:

BAM=5'-GGC GCC GGA TCC TAC CGC AAC GAC GGC ACC GAG C; and NDE (described above)

The first six nucleotides of primer BAM are random G+C which are there only to make digestion of the subsequent PCR fragment with BamHI easier. The next six nucleotides constitute the new BamHI site which is to be introduced and the remaining nucleotides are homologous to the cinnamycin cluster from position 961 to 982. The PCR product produced using BAM and NDE was 1123 bp long and was produced using pDWFT4 as a template and Taq-polymerase other reaction conditions were the same as those for StuPCR2. It was then digested with BamHI and XhoI to generate an approximately 770 bp fragment with a BamHI compatible end and a XhoI compatible end. This fragment was then purified by agarose gel electrophoresis and cloned into pBluescriptIIKS that had been cut with BamBI and XhoI to give pDWFT11. The BamHI fragment from pDWFT4 was sub-cloned into BamHI cut pUC18 so that the XhoI site within the BamHI fragment was closest to the XbaI site of pUC18 to give pDWFT14f. The plasmid pDWFT11 was then digested with XbaI and XhoI which releases the cloned PCR fragment plus a small piece of the pUC18 polylinker region. This fragment was then purified by agarose gel electrophoresis and cloned into pDWFT14f that had been cut with XbaI and XhoI to give pDWFT15. This restores the native conformation of the cinA gene and creates a new BamHI fragment that corresponds to the region of pDWFT4 that lies between position 961 and 4872 of FIG. 4. This BamHI fragment was subsequently cloned into pDWFT6 and thence into pOJ436 in a similar manner to that in which pDWFT4 gave rise to pDWFT8, to yielding pDWFT25.

The second step in this process was to generate the variant of pDWFT5. A PCR product was generated using the following two primers:

KPN=5'-GGC GCC GGT ACC GAG GAC GTC GAG CTG TTC GAG C (The first six nucleotides of primer KPN are random G+C which are there only to make digestion of the subsequent PCR fragment with Asp718 easier. The following six nucleotides constitute the new Asp718 site which is introduced and the remaining nucleotides are homologous to the cinnamycin cluster from position 15621 to 15599)

FTP1=5' CAG GTC GCC GAC GAT CTC GTC G

These primers were used to generate a PCR fragment using Pfu-polymerase and pDWFT5 as a template otherwise the reaction conditions were the same as those for StuPCR1. The PCR fragment was approximately 1025 bp long and was digested with BamHI and Asp718 to give a fragment that was approximately 956 bp long which was then purified by agarose gel electrophoresis and cloned into pUC18 cut with BamHI and Asp718 to give pDWFT16. An approximately 6.5 kb BamHI fragment was cloned from *S. cinnamoneus cinnamoneus* 40005 chromosomal DNA in a manner similar to that used to clone the Asp718 fragment in pDWFT5 with the modification that the chromosomal DNA was cut with BamHI and cloned into BamHI cut pBluescriptII to give pDWFT3. The 6.5 kb BamHI from pDWFT3 corresponding to positions 8016 to 14660 of FIG. 4, was cloned into BamHI cut pDWFT16 such that the portions of cinR1 on the fragment and pDWFT16 are contiguous, yielding pDWFT24. This plasmid was then cut with BglII and EcoRI which releases a approximately 6.9 kb fragment (which corresponds to positions 8730 to 15621 of FIG. 4) that was purified by agarose gel electrophoresis and cloned into pDWFT5 that had been cut with BglII and EcoRI and the approximately 6.3 kb fragment purified by agarose gel electrophoresis to give pDWFT27. This plasmid contains an Asp718 fragment that corresponds to positions 5423 to 15621 of FIG. 4. The final step was to digest pDWFT27 with Asp718 and purify the approximately 10 kb fragment by agarose gel electrophoresis and clone it into Asp718 cut pDWFT25 so that the portion of the cinX gene carried on the Asp718 fragment corresponds to the portion of the cinM gene carried on pDWFT25, yielding pDWFT28. This plasmid was then transformed into S. lividans 1326. The DNA carried on pDWFT28 corresponds to the region between positions 961 to 15621 of FIG. 4). A transformant was selected and the resulting strain, DW28, was bioassayed for cinnamycin and cultures grown for MALDI-TOF analysis as described above.

Construction of Single Gene Deletions from the Cinnamycin Cluster Carried on pDWFT9

A series of constructs was created in which the single genes were removed so that the open-reading frame was completely missing from the start codon to the stop codon and either deleted completely, replaced with a StuI restriction site or replaced with a tetracycline resistance gene, Tc, derived from pDWFT33. This was to formally test the hypothesis that these genes were essential for cinnamycin production.

Construction of a cinorf7 Deletion

This was achieved by replacement of the desired gene with a PCR generated replacement cassette, which carries a selectable marker, using homologous recombination. In this case the replacement cassette used was the Tc gene, which confers tetracycline resistance, from pDWFT33. A plasmid carrying the gene to be replaced is transformed into E.coli BW25113 pIJ790 (available from the JIC) which possesses the plasmid pIJ790 (pIJ790 is based on the plasmid pKD20 (Datsenko and Wanner, 2000) but carries a chloramphenicol resistance gene (cat) instead of an ampicillin resistance gene (bla)) which carries an arabinose inducible recombination system based on that of the λ phage. PCR primers are designed which are homologous to the desired replacement cassette at their 3'-ends and have 5'-extensions which are homologous to the DNA flanking the region to be replaced. A PCR product is prepared using these primers which is then transformed into E.coli BW25113 pIJ790 plus target plasmid. The induced recombinase within the cell then uses the regions of homology, incorporated into the 5'-extensions of the PCR primers, to the sequences flanking the target DNA to replace the target DNA with the replacement cassette. Transformants can then be selected for using the selectable marker carried on the replacement cassette.

The oligonucleotide primers incorporated StuI restriction sites between the regions homologous to the flanking regions of the gene to be replaced and the regions homologous to the Tc replacement cassette. It was subsequently possible to remove the Tc replacement cassette by StuI restriction digestion to leave a StuI site in place of cinorf7.

The following oligonucleotide primers were synthesised:
7A=5'-TCG TTC TCA CCG GGA ACC GAC TGG ATG GGG AAA CGG GCC AGG CCT CGC CGG CTT CCA TTC AGG. This primer has homology to the cinnamycin cluster from position 1228 to 1266; and
7B 5'-ACC TCC GAT GTT GAG GTG AAT CCC GGC ACC CGG CGG GTG AGG CCT AAT AGG CGT ATC ACG AGG. This primer has homology to the cinnamycin cluster from position 1665 to 1627

A PCR was prepared that was labelled PCR7 using 7A and 7B as primers with Taq-polymerase and pDWFT33 as a template using a reaction mixture similar to that for StuPCR2 and the following thermal cycle 3 min at 94° C. followed by 5 cycles of melting at 94° C. for 35 sec, annealing at 55° C. for 1 min and elongation at 52° C. for 2 min then 20 cycles of melting at 94° C. for 35 sec, annealing at 60° C. for 1 min and elongation at 72° for 2 min. The PCR product was then purified by agarose gel electrophoresis. The plasmid pDWFT7 was transformed into E. coli BW25113 pIJ790 (available from the JIC). E. coli BW25113 pIJ790 pDWFT7 was grown in 10 ml SOB (Hanahan, 1983) with chloramphenicol(25 µg/ml) apramycin and L-arabinose (final concentration of 10 mM) at 30° C. to an $OD_{600}$ of ~0.6 and then made electro-competent by washing twice with 10 ml ice-cold 10% glycerol and resuspended in 100 µl 10% glycerol. Cells were electroporated with ~100 ng of purified PCR7. Electroporation was carried out in 0.2 cm ice-cold electroporation chambers using a BioRad GenePulser II set to the following parameters: 200 Ω, 25 µF and 2,5 kV. Shocked cells were added to 1 ml LB (Luria-Bertani medium; Sambrook et al., 1998), incubated 1 h at 30° C. and then spread onto LB agar+tetracycline (10 µg/ml) and incubated o/n at 37° C. to select for the successful replacement of the target gene by the PCR product containing the Tc gene. In this way a variant of pDWFT7 was selected in which cinorf7 was replaced with a StuI flanked Tc gene which was labelled pDWFT73. This plasmid was then used to create a variant of pDWFT9 in which cinorf7 was replaced with the StuI flanked Tc gene, in a similar manner to which pDWFT7 was used to create pDWFT9, to give pDWFT77. This plasmid was then digested with StuI and the large fragment produced was purified by agarose gel electrophoresis and religated to create pDWFT78, a version of pDWFT9 in which cinorf7 was replaced with a StuI site. This plasmid was then introduced into S. lividans 1326 by conjugation. This was carried out as follows. The plasmid pDWFT78 was transformed into E. coli ET12567/pUZ8002. A single colony of the resulting strain (ET12567/pUZ8002/pDWFT78 was inoculated into 10 ml LB containing kanamycin (25 µg/ml), chloramphenicol (25 µg/ml) and apramycin (50 µg/ml) and grown overnight at 37° C. The overnight culture was diluted 1:100 in fresh LB with antibiotic selection (see above) and grown at 37° C. to an $OD_{600}$ of approximately 0.4–0.6. The cells were washed twice with an equal volume of LB to remove antibiotics and resuspended in 1 ml of LB.

For each conjugation, approximately $10^8$ Streptomyces spores were added to 500 µl 2×YT broth, heat shocked at 50° C. for 10 min, allowed to cool and then mixed with 500 µl ET12567/pUZ8002/pDWFT78 cells, spun briefly and most of the supernatant was poured off. The pellet was resuspended in the residual liquid and plated out on SFM agar+10 mM $MgCl_2$ (Kieser et al., 2000) and incubated at 30° C. for 16–20 h.

Plates were overlaid with 1 ml water containing 0.5 mg nalidixic acid (which kills E. coli, thereby selecting for the Streptomyces cells) and 1 mg apramycin and incubated at 30° C. for 3–6 days. Exconjugants were streaked onto SFM+nalidixic acid (50 μg/ml) and apramycin (50 μg/ml) The strain thus created, C78, was bioassayed for cinnamycin production, as previously described, and grown as lawns on SFM+ and apramycin (50 μg/ml) for spore preps to prepare liquid cultures for use in MALDI-TOF assays. These liquid cultures were prepared as described before but instead of subjecting the spent media to organic solvent extractions it was diluted 1/10 in 10% formic acid and used directly in the MALDI-TOF mass-spectrophotometer.

Construction of a cinA Deletion

This was achieved by producing overlapping PCR products where, in each PCR product, one of the primer sequences had homolgy to regions of the DNA that immediately flank the cinA gene. These primers also have a certain amount of overlap between each other so that the subsequent PCR primers can be annealed to each other and extended so that the resulting product can be amplified with the flanking PCR primers.

The following oligonucleotide primers were synthesised:

FTP35=5'-GGC GAC AGC AGC GTC TCG GAC C. This primer has homology to the cinnamycin cluster from position 811 to 832;

LA=5'-GGC AGC AGC CAC GGC TTA CCT CCG ATG TTG AGG. This primer has homology to the cinnamycin cluster from position 1670 to 1650 and from 1919 to 1908;

RA=5'-CGG AGG TAA GCC GTG GCT GCT GCC TCT AGG This primer has homology to the cinnamycin cluster from position 1659 to 1650 and from 1908 to 1925; and FTP28=5'-TTC AGG TAG AAG CGG TGG TAG G This primer has homology to the cinnamycin cluster from position 2795 to 2774

Using Pfu polymerase and pDWFT4 as a template, PCRs were prepared using the primer pair FTP35 and LA, using similar reaction conditions to StuPCR1, to give a PCR product that was labelled CINAPCR1 whilst, using similar reaction conditions, RA and FTP28 were used to produce a PCR product labelled CINAPCR2. These PCR products were purified by agarose gel electrophoresis then PCR using primer pairs FTP35 and FTP28 to give PCR product CINAPCR3 in a similar manner to that used for the creation of StuPCR3. This product was then purified by agarose gel electrbphoresis and digested with SalI and PstI and cloned into pUC18 that had been cut with SalI and PstI, and purified by agarose gel electrophoresis, to give pDWFT35. The plasmid pDWFT14r (made similarly as pDWFT14f but with the approximately 5 Kb BamHI fragment oriented in the opposite direction) was digested with Asp718 and SalI and the approximately 900 bp fragment purified by agarose gel electrophoresis and cloned into pDWFT35 that had been cut with Asp718 and SalI, and purified by agarose gel electrophoresis, to give pDWFT55. The plasmid pDWFT4 was then cut with PstI and XbaI and the approximately 2.5 kb fragment was purified by agarose gel electrophoresis and cloned into pDWFT55 that had been cut with PstI and XbaI, purified by agarose gel electrophoresis, to give pDWFT56.

The resulting plasmid pDWFT56, is similar to pDWFT4 except that it lacks the cinA gene. This plasmid was then used to reconstruct a cinnamycin cluster similar to pDWFT9, but lacking cinA, via a similar pathway to that used to make pDWFT9 to give pDWFT69. This plasmid was then introduced into S. lividans 1326 by conjugation as described for the construction of a cinorf7 deletion. The resulting strain, C69, was bioassayed for cinnamycin and cultures grown for MALDI-TOF analysis as described for construction of a cinorf7 deletion.

Construction of a cinM Deletion

This was achieved by producing overlapping PCR products where, in each PCR product, one of the primer sequences had homolgy to regions of the DNA that immediately flank the cinM gene. These primers also have a certain amount of overlap between each other so that the subsequent PCR primers can be annealed to each other and extended so that the resulting product can be amplified with the flanking PCR primers.

The following oligonucleotide primers were synthesised:

XHO (see above);

LM=5'-TGG AGC CAC TCC ATG-CGA ATT TCT CCT GCG GTC G. This primer has homology to the cinnamycin cluster from position 5337 to 5326 and from 2058 to 2037;

RM=5'-AGA AAT TCG CAT GGA GTG GCT CCA CCA TGG. This primer has homology to the cinnamycin cluster from position 2047 to 2058 and from 5326 to 5343; and FTPMR=5'-CGG CCG AGC TCG ACG ATC TCC. This primer has homology to the cinnamycin cluster from position 5449 to 5429.

Using Pfu polymerase and pDWFT9 as a template PCRs were prepared using the primer pair XHO and LM, using similar reaction conditions to StuPCR1, to give a PCR product that was labelled CINMPCR1. Using similar reaction conditions, RM and FTPMR were used to produce a PCR product labelled CINAPCR2. These PCR products were purified by agarose gel electrophoresis then subject to PCR using primer pairs XHO and FTPMR to give PCR product CINAPCR3 in a similar manner to that used for the creation of StuPCR3. This product was then purified by agarose gel electrophoresis and digested with XhoI and Asp718 and cloned into the approximately 4.7 kb fragment from pDWFT7 that had been cut with XhoI and Asp718 and purified by agarose gel electrophoresis, to give pDWFT43. The plasmid pDWFT43 is similar to pDWFT7 except that it lacks the cinM gene. This plasmid was then used to reconstruct a cinnamycin cluster similar to pDWFT9, but lacking cinM, via a similar pathway to that used to make pDWFT9 to give pDWFT68. This plasmid was then introduced into S. lividans 1326 by conjugation as described for construction of a cinorf7 deletion. The resulting strain, C68, was bioassayed for cinnamycin and cultures-grown for MALDI-TOF analysis as described for construction of a cinorf7 deletion.

Construction of a cinX Deletion

The construction of a cinX deletion was achieved in a similar manner to that used for cinorf7 to leave a StuI site in place of cinX.

The following primers were used:

XA=5'-CCC GCC GTC GCA CCA CGA ACA GTA AGG AGT GGC TCC ACC AGG CCT CGC CGG CTT CCA TTC AGG. This primer has homology to the cinnamycin cluster from position 5301 to 5339; and XB=5'-TCC TTG GTG CCG CGC GGT GCG CGG ACG ACG GGT GCC GGG AGG CCT AAT AGG CGT ATC ACG AGG. This primer has homology to the cinnamycin cluster from position 6356 to 6318.

Using XA and XB as primers a PCR was prepared in a similar manner to that for cinorf7 that was labelled PCRX. The plasmid pDWFT5 was digested with Asp718 and the approximately 11.5 kb fragment was purified by agarose gel electrophoresis and cloned into pDWFT7 that had been cut with Asp718, and purified by agarose gel electrophoresis, such that the native orientation of the cinnamycin cluster was restored to give pDWFT74. The plasmid pDWFT74 was transformed into E. coli BW25113 pIJ790. The BW25113 pIJ790 pDWFT74 strain was then used to produce electro-competent cells which were transformed by electroporation with PCRX in the same manner as described for cinorf7. In this way a variant of pDWFT74 was selected in which cinX was replaced with a StuI flanked Tc gene which was labelled pDWFT79. This plasmid was then used to create a variant of pDWFT9 in which cinX was replaced with the StuI flanked Tc gene by digesting it with XbaI and Asp718 and cloning it into XbaI and Asp718 cut pOJ436 to give pDWFT82. This plasmid was then digested with StuI and the large fragment produced was purified by agarose gel electrophoresis and religated to create pDWFT90, a version of pDWFT9 in which cinX was replaced with a StuI site. This plasmid was then introduced into S. lividans 1326 by conjugation as described for construction of a cinorf7 deletion. The resulting strain, C90, was bioassayed for cinnamycin and cultures grown for MALDI-TOF analysis as described for construction of a cinorf7 deletion.

Construction of a cinR Deletion

This was achieved in a similar manner to that used for cinorf7 to leave a StuI site in place of cinR.

The following primers were used:

RA=5'-TCA GCA CTG TCG AAG AAC ACC TCG CGC CGG GAG CGG CAT AGG CCT CGC CGG CTT CCA TTC AGG. This primer has homology to the cinnamycin cluster from position 11798 to 11760; and RB=5'-CTG CTG ACA CCC GGC CCG TAG CGG TCA CGG CTC ACA CCG AGG CCT AAT AGG CGT ATC ACG AGG. This primer has homology to the cinnamycin cluster from position 11072 to 11110.

Using RA and RB as primers a PCR was prepared in a similar manner to that prepared for cinorf7 that was labelled PCRR. The plasmid pDWFT5 was transformed into E. coli BW25113 pIJ790. The strain BW25113 pIJ790 pDWFT5 was then used to produce electro-competent cells which were transformed by electroporation with PCRR in the manner described for cinorf7. In this way a variant of pDWFT5 was selected in which cinR was replaced with a StuI flanked Tc gene which was labelled pDWFT80. This plasmid was then used to create a variant of pDWFT9 in which cinR was replaced with the StuI flanked Tc gene, in a similar manner to which pDWFT5 was used to create pDWFT9, to give pDWFT85. This plasmid was then digested with StuI and the large fragment produced was purified by agarose gel electrophoresis and re-ligated to create pDWFT88, a version of pDWFT9 in which cinR was replaced with a StuI site. This plasmid was then introduced into S. lividans 1326 by conjugation as described for construction of a cinorf7 deletion. The resulting strain, C88, was bioassayed for cinnamycin and cultures grown for MALDI-TOF analysis as described for construction of a cinorf7 deletion.

Construction of a cinR1 Deletion

This was achieved in a similar manner to that used to replace cinorf7 to replace cinR1 with the Tc replacement cassette.

The following primers were used:

SARPA=5'-GTC TTC AGG GTG CGG CTC GAT GAG CGA AGG GGA GAG TTC AGG CCT CGC CGG CTT CCA TTC AGG. This primer has homology to the cinnamycin cluster from position 15199 to 15161; and SARPB=5'-CTC GTG CAC CGC CGG CGC GCG CGC CGG GCG GTG GGC GGC AGG CCT AAT AGG CGT ATC ACG AGG. This primer has homology to the cinnamycin cluster from position 14336 to 14374.

Using SARPA and SARPB as primers a PCR was prepared in a similar manner to that prepared for cinorf7 that was labelled PCRSARP. The plasmid pDWFT5 was transformed into E. coli BW25113 pIJ790. The strain BW25113 pIJ790 pDWFTS was then used to produce electro-competent cells which were transformed by electroporation with PCRSARP in the manner described for cinorf7. In this way a variant of pDWFT5 was selected in which cinR1 was replaced with a StuI flanked Tc gene which was labelled pDWFT81. This plasmid was then used to create a variant of pDWFT9 in which cinR1 was replaced with the StuI flanked Tc gene, in a similar manner to which pDWFT5 was used to create pDWFT9, to give pDWFT89. This plasmid was then introduced into S. lividans 1326 by conjugation as described for construction of a cinorf7 deletion. The resulting strain, C89, was bioassayed for cinnamycin and cultures grown for MALDI-TOF analysis as described for construction of a cinorf7 deletion.

Results

All of the deletion constructs of the cinnamycin cluster described above were examined by bio-assay to determine whether they could still produce an antibiotic compound. See Table 5.

Strains DW28 (deletions of the regions upstream of cinA and cinR1) and C90 (cinX deletion) still produce an antibiotic compound whilst strains C78 (cinorf7 deletion), C69 (cinA deletion), C68 (cinM deletion), C88 (cinR deletion) and C89 (cinR1 deletion) do not. These results indicate that the regions deleted from the cinnamycin clusters in C78, C69, C68, C88 and C89 (which correspond to the genes cinorf7, cinA, cinM cinR and cinR1 respectively) are essential for the inhibition of growth of B. subtillis in a bio-assay. However, the regions deleted from the cinnamycin cluster in DW28 (which include all of cinorf3, cinorf13 and cinorf14 and most of cinorf4 and cinorf12) and C90 (cinX deletion) are not essential for the inhibition of growth of B. subtillis in a bio-assay. Supernatants from these strains were examined by MALDI-TOF mass spectrometry to determine if a compound with the MW of cinnaycin was still made by these strains. See Table 6.

The MALDI-TOF mass spectrometry data shown in Table 6 indicate that DW28 and C78 still produce cinnamycin (MW=2039) whilst C69, C68 and C90 do not. This indicates that cinA, cinM and cinX are essential for cinnamycin production. However, in the three strains shown in Table 6 that do produce cinnamycin there is also a peak with a MW of 2023 daltons (16 daltons lighter than cinnamycin). This peak is absent from two of the three strains unable to make cinnamycin, C69 (cinA deletion) and C68 (cinM deletion), but is present in C90 (cinX deletion).

Discussion

All of the results discussed below pertain to the functions of the genes of the cinnamycin cluster in S. lividans 1326.

We have demonstrated that by the introduction of unique restriction sites either side of the cinA pro-peptide encoding region we can replace the region of cinA that encodes the structural gene for cinnamycin with one that encodes a variation on cinnamycin. In this case we have evidence that shows that the cinnamycin cluster can be manipulated to produce duramycin and duramycinB instead of cinnamycin. The approach exemplified herein can be used for the production of many different and novel variations of cinnamycin.

With the strain DW28 we have also shown that positions 1 to 961 and 15621 to 17083 of the cinnamycin cluster as represented in FIG. 4 are not essential for the production of cinnamycin in S. lividans 1326. This means that cinorf3, cinorf13 and cinorf14 are not essential to the production of cinnamycin. It also suggests that cinorf4 is not essential as it is only present in a truncated form that also lacks its promoter region. It also suggests that the product of cinorf12 may not be essential for cinnamycin production.

The strains C69 and C68 show that the genes cinA and cinM are both essential for cinnamycin production by both bio-assay and mass spectrometry analysis. The gene cinA is the structural gene for cinnamycin which we have already demonstrated can be manipulated to make the cinnamycin cluster produce natural variants of cinnamycin. The gene cinM is thought to encode a LanM type protein that would be responsible for the production of the lanthionine residues of cinnamycin.

The strain C78 does not produce a zone of inhibition in a bio-assay but according to mass spectometry analysis does produce cinnamycin. This suggests that although it produces enough cinnamycin to be detected in a MALDI-TOF mass spectrometer it does not produce enough to inhibit the growth of B. subtilis. This indicates that although cinorf7 is not essential for cinnamycin production it does greatly enhance its production.

The strain C90 produces a zone of inhibition in a bio-assay but does not produce a compound with the molecular weight of cinnamycin. However it, along with the other cinnamycin producing strains in Table 6, does produce a compound 16 daltons lighter than cinnamycin. Amongst the post-translational modifications of the cinnamycin propeptide is the addition of an oxygen atom to the aspatate residue to form beta-hydroxy aspartate. The results shown here suggest that the process that adds this oxygen atom is not efficient and some of the cinnamycin pre-cursor, which we shall term deoxycinnamycin, is secreted before it is modified and this is represented by the peak with a MW of 2023 as detected by MALDI-TOF mass spectrometry. That C90 only produces a peak with a MW that corresponds to deoxycinnamycin suggests the product of cinX is an enzyme responsible for the addition of the oxygen atom to the aspartate residue of the propeptide to form cinnamycin. This would mean that by removing cinX from the cinnamycin cluster and combining this with the methods described above for the production of variants of cinnamycin one could produce both variants and deoxy-variants. Also by increasing the copy number of cinX in a strain one may be able to increase the amount of cinX product within a cell and thus reduce the amount of deoxycinnamycin (or deoxy-variant) produced by a S. lividans strain hosting the cinnamycin cluster.

The bio-assay results for strains C88 and C89 suggests that the genes cinR and cinR1 are at least necessary for the production of enough cinnamycin to be detected by bio-assay in a S. lividans strain.

TABLE 1

The effect on the growth of B. subtilis by strains of S. lividans possessing either the plasmid pDWFT9 or the vector pOJ436.

| Strain | Inhibition of the Growth of B. subtilis |
|---|---|
| S. cinnamoneus cinnamoneus DSM 40005 | + |
| DW9a-1 | + |
| DW9a-2 | + |
| DW9a-3 | + |
| DW9a-4 | + |

TABLE 1-continued

The effect on the growth of B. subtilis by strains of S. lividans possessing either the plasmid pDWFT9 or the vector pOJ436.

| Strain | Inhibition of the Growth of B. subtilis |
|---|---|
| DW9a-5 | + |
| Dw9a-6 | + |
| DW9a-7 | + |
| DW9a-8 | + |
| DW9a-9 | + |
| DW436-1 | − |
| DW436-2 | − |
| DW436-3 | − |
| DW436-4 | − |

TABLE 2

The detection of compounds with similar molecular weights to cinnamycin by MALDI-TOF mass spectrometry

| | Strain | | | | | |
|---|---|---|---|---|---|---|
| | Streptomyces cinnamoneus cinnamoneus DSM 4000 | | 5DW9a-1 | | DW436-4 | |
| | | | Growth media | | | |
| | TSB | YEME | TSB | YEME | TSB | YEME |
| Presence of molecule of MW 2039.9 ± 0.1 | + | + | + | + | − | − |

TABLE 3

The effect on the growth of B. subtilis by strains of S. lividans possessing plasmids that carry a cluster encoding variants of cinnamycin

| | Strain | | | |
|---|---|---|---|---|
| | DW436-4 | DW9a-1 | DW52 | DW54 |
| Inhibition of the Growth of B. subtilis | − | + | + | + |

TABLE 4

The detection of cinnamycin and its derivatives by MALDI-TOF mass spectrometry

| Presence of molecule with MW of | Strain | | | |
|---|---|---|---|---|
| | DW436-4 | DW9a-1 | DW52 | DW54 |
| cinnamycin MW = 2039.9 ± 0.1 | − | + | − | − |
| durainycinB MW = 2005 | − | − | + | − |
| duramycin MW = 2011 | − | − | − | + |

TABLE 5

The effect on the growth of *B. subtilis* by strains of *S. lividans* possessing variants of pDWFT9 in which different sections of DNA been deleted.

| | Strain | | | | | | | | |
|---|---|---|---|---|---|---|---|---|---|
| | DW436-4 | DW9a-1 | DW28 | C78 | C69 | C68 | C90 | C88 | C89 |
| Inhibition of the growth of *B. subtilis* | − | + | + | − | − | − | + | − | − |

TABLE 6

The detection of cinnamycin by MALDI-TOF mass spectrometry by strains of *S. lividans* possessing variants of pDWFT9 in which different sections of DNA have been deleted.

| | Strain | | | | | |
|---|---|---|---|---|---|---|
| | C9 | DW28 | C78 | C69 | C68 | C90 |
| MW = 2039 | + | + | + | − | − | − |
| MW = 2023 | + | + | + | − | − | + |

Note:
Strain C9 possesses pDWFT9 and so is similar to strain DW9a-1 but was created using conjugation instead of transformation.

The invention claimed is:

1. A recombinant expression cassette comprising a cinA (SEQ ID NO: 10) orf, a cinM (SEQ ID NO: 11) orf and optionally a cinX (SEQ ID NO: 12) orf.

2. A set of recombinant expression cassettes comprising a cinA (SEQ ID NO: 10) orf, a cinM (SEQ ID NO: 11) orf and optionally a cinX (SEQ ID NO: 12) orf.

3. A recombinant expression cassette comprising a cinA (SEQ ID NO: 10) open reading frame (orf), a cinM orf (SEQ ID NO: 11), a cinT (SEQ ID NO: 13) orf, a cinH (SEQ ID NO: 14) orf, a cinY (SEQ ID NO: 15) orf and optionally a cinX (SEQ ID NO: 12) orf.

4. A set of recombinant expression cassettes together comprising a cinA (SEQ ID NO: 10) orf, a cinM (SEQ ID NO: 11) orf, a cinT (SEQ ID NO: 13) orf, a cinH (SEQ ID NO: 14) orf, a cinY(SEQ ID NO: 15) orf and optionally a cinX (SEQ ID NO: 12) orf.

5. The expression cassette of claim 3 or the set of expression cassettes of claim 4, further comprising a *streptomyces* antibiotic regulatory proteins (SARP) binding site, a cinorf7 (SEQ ID NO: 9) orf, a cinR (SEQ ID NO: 19) orf, a cinK (SEQ ID NO: 20) orf and a cinR (SEQ ID NO: 23) orf.

6. The cassette or set according to claim 5, wherein the SARP binding site is upstream of the cinorf7 (SEQ ID NO: 9) orf.

7. The cassette or set according to claim 6, wherein the cinorf7 (SEQ ID NO: 9) orf forms an operon with the cinA (SEQ ID NO: 10), cinM (SEQ ID NO: 11), cinX (SEQ ID NO: 12), cinT (SEQ ID NO: 13), cinH (SEQ ID NO: 14) and cinY(SEQ ID NO: 15) orfs.

8. The cassette or set according to any one of claims 3 or 4, further comprising one or more orfs selected from the group consisting of cinorf3 (SEQ ID NO: 6), cinorf4 (SEQ ID NO: 7), smallorf (SEQ ID NO: 8), cinZ (SEQ ID NO: 16), cinorf8 (SEQ ID NO: 17), cinorf9 (SEQ ID NO: 18), cinorf10 (SEQ ID NO: 21), cinorf11 (SEQ ID NO: 22), cinorf12 (SEQ ID NO: 24), cinorf13 (SEQ ID NO: 25) and cinorf14 (SEQ ID NO: 26).

9. The cassette or set according to claim 8, wherein said one or more orfs include one of more orfs selected from the group consisting of cinorf4 (SEQ ID NO: 7), smallorf (SEQ ID NO: 8), cinZ (SEQ ID NO: 16), cinorf8 (SEQ ID NO: 17), cinorf9 (SEQ ID NO: 18), cinorf10 (SEQ ID NO: 21), cinorf11 (SEQ ID NO: 22) and cinorf12 (SEQ ID NO: 24).

10. The cassette or set according to claim 9, wherein said one or more orfs include one or more orfs selected from the group consisting of smallorf (SEQ ID NO: 8), cinZ (SEQ ID NO: 16), cinorf8 (SEQ ID NO: 17), cinorf9 (SEQ ID NO: 18), cinorf10 (SEQ ID NO: 21) and cinorf 11 (SEQ ID NO: 22).

11. The cassette or set according to claim 10, wherein said one or more orfs include cinZ (SEQ ID NO: 16) and/or cinorf8 (SEQ ID NO: 17).

12. The expression cassette of claim 3 further comprising regulatory sequences suitable for directing transcription and translation of the orfs in a host cell.

13. A vector, or set of vectors, comprising, or together comprising, a cassette or set of cassettes according to claim 1 or 2.

14. An isolated expression system comprising a vector or set of vectors according to claim 13.

15. The isolated expression system according to claim 14, wherein the expression system is a cell.

16. The isolated expression system according to claim 15, wherein the cell is a bacterium.

17. The isolated expression system according to claim 16, wherein the bacterium is an actinomycete.

18. The isolated expression system according to claim 17, wherein the actinomycete bacterium is a streptomycete.

19. The isolated expression system according to claim 18, wherein the streptomycete bacterium is *S. lividans*.

20. An isolated set of recombinant expression cassettes together comprising a cinA orf, a cinM (SEQ ID NO: 11) orf, a cinT (SEQ ID NO: 13) orf, a cinH (SEQ ID NO: 14) orf and a cinY (SEQ ID NO: 15) orf and optionally a cinX (SEQ ID NO: 12) orf wherein the cinA orf encodes the polypeptide sequence of FIG. 11, optionally with one or more amino acids of the propeptide sequence of cinA (amino acids 60 to 78 of SEQ ID NO: 10) replaced with the amino acid found in the corresponding position in the propeptide sequence of duramycin A, B or C or ancovenin.

21. The set according to claim 4, further comprising regulatory sequences suitable for directing transcription and translation of the orfs in a host cell.

22. A recombinant expression cassette comprising a cinA orf, a cinM (SEQ ID NO: 11) orf and optionally a cinX (SEQ ID NO: 12) orf, wherein the cinA orf encodes the polypeptide sequence of SEQ ID NO: 10, optionally with up to six amino acids of the propeptide sequence of cinA (amino acids 60 to 78 of SEQ ID NO: 10) replaced with an amino acid found in the corresponding position in the propeptide sequence of a B-type lantibiotic other than cinnamycin.

23. A recombinant expression cassette comprising a cinA orf, a cinM (SEQ ID NO: 11) orf and optionally a cinX (SEQ ID NO: 12) orf, wherein the cinA orf encodes the polypeptide sequence of SEQ ID NO: 10, optionally with one or more of the amino acids in positions 2, 3, 7, 10, 12 and 13 of the propeptide sequence of cinA (amino acids 60 to 78 of SEQ ID NO: 10) replaced with an amino acid found in the corresponding position in the propeptide sequence of a B-type lantibiotic other than cinnamycin.

24. The cassette of claim 22 or claim 23 further comprising a cinT (SEQ ID NO: 13) orf, a cinH (SEQ ID NO: 14) orf, and a cinY (SEQ ID NO: 15) orf.

25. The cassette of claim 22 or claim 23 wherein the B-type lantibiotic other than cinnamycin is selected from the group consisting of duramycin A, B and C and ancovenin.

26. An isolated set of recombinant expression cassettes together comprising a cinA orf, a cinM (SEQ ID NO: 11) orf and optionally a cinX (SEQ ID NO: 12) orf, wherein the cinA orf encodes the polypeptide sequence of SEQ ID NO: 10, optionally with up to six amino acids of the propeptide sequence of cinA (amino acids 60 to 78 of SEQ ID NO: 10) replaced with an amino acid found in the corresponding position in the propeptide sequence of a B-type lantibiotic other than cinnamycin.

27. An isolated set of recombinant expression cassettes together comprising a cinA orf, a cinM (SEQ ID NO: 11) orf and optionally a cinX (SEQ ID NO: 12) orf, wherein the cinA orf encodes the polypeptide sequence of SEQ ID NO: 10, optionally with one or more of the amino acids in positions 2, 3, 7, 10, 12 and 13 of the propeptide sequence of cinA (amino acids 60 to 78 of SEQ ID NO: 10) replaced with an amino acid found in the corresponding position in the propeptide sequence of a B-type lantibiotic other than cinnamycin.

28. The set of claim 26 or claim 27 further comprising a cinT (SEQ ID NO: 13) orf, a cinH (SEQ ID NO: 14) orf and a cinY (SEQ ID NO: 15) orf.

29. The set of claim 26 or claim 27 wherein the B-type lantibiotic other than cinnamycin is selected from the group consisting of duramycin A, B and C and ancovenin.

30. A vector, or set of vectors, comprising, or together comprising, a cassette or set of cassettes according to claim 26 or 27.

31. An isolated expression system comprising a vector or set of vectors according to claim 30.

32. The isolated expression system according to claim 31, which is a cell.

33. The isolated expression system according to claim 32, wherein the cell is a bacterium.

34. The isolated expression system according to claim 33, wherein the bacterium is an actinomycete.

35. The isolated expression system according to claim 34, wherein the actinomycete bacterium is a streptomycete.

36. The isolated expression system according to claim 35, wherein the streptomycete bacterium is *S. lividans*.

37. A recombinant expression cassette comprising a cinA open reading frame (orf), wherein said orf encodes the polypeptide sequence of SEQ ID NO: 10, optionally with up to six amino acids of the propeptide sequence of cinA (amino acids 60 to 78 of SEQ ID NO: 10) replaced with an amino acid found in the corresponding position in the propeptide sequence of a B-type lantibiotic other than cinnamycin,
   said cassette further encoding a cinM orf, a cinT orf, a cinH orf and a cinY orf and optionally a cinX orf, wherein said orfs each have a nucleic acid sequence which encodes a polypeptide that is identical to the sequences as set out in SEQ ID NO's: 11–15 respectively, and wherein said orfs, when introduced into SEQ ID NO: 4 in place of nucleic acid encoding SEQ ID NO's: 11–15 respectively are capable of providing for production of a molecule having a lantibiotic activity in a host cell.

38. A set of recombinant expression cassettes together comprising:
   a cinA open reading frame (orf), wherein said orf encodes the polypeptide sequence of SEQ ID NO: 10, optionally with up to six amino acids of the propeptide sequence of cinA (amino acids 60 to 78 of SEQ ID NO: 10) replaced with an amino acid found in the corresponding position in the propeptide sequence of a B-type lantibiotic other than cinnamycin,
   a cinM orf, a cinT orf, a cinH orf and a cinY orf and optionally a cinX orf, wherein said orfs each have a nucleic acid sequence which encodes a polypeptide that is identical to the sequences as set out in SEQ ID NO's: 11–15 respectively, and wherein said orfs, when introduced into SEQ ID NO: 4 in place of nucleic acid encoding SEQ ID NO's: 11–15 respectively are capable of providing for production of a molecule having a lantibiotic activity in a host cell.

39. A recombinant expression cassette comprising a cinA open reading frame (orf), wherein said orf encodes the polypeptide sequence of SEQ ID NO: 10, optionally with up to six amino acids of the propeptide sequence of cinA (amino acids 60 to 78 of SEQ ID NO: 10) replaced with an amino acid found in the corresponding position in the propeptide sequence of a B-type lantibiotic other than cinnamycin,
   said cassette further encoding cinorf7, wherein said cinorf7 has a nucleic acid sequence which encodes a polypeptide that is identical to the sequence as set out in SEQ ID NO: 9, and wherein said orfs, when introduced into SEQ ID NO: 4 in place of nucleic acid encoding SEQ ID NO: 9 is capable of providing for production of a molecule having a lantibiotic activity in a host cell.

40. The recombinant expression cassette of claim 39 wherein said cinA open reading frame encodes the polypeptide sequence of SEQ ID NO: 10, optionally with one or more of the amino acids in positions 2, 3, 7, 10, 12 and 13 of the propeptide sequence of cinA (amino acids 60 to 78 of SEQ ID NO: 10) replaced with an amino acid found in the corresponding position in the propeptide sequence of a B-type lantibiotic other than cinnamycin.

41. The recombinant expression cassette of claim 39 wherein said cinorf7 has a nucleic acid sequence which encodes the polypeptide of SEQ ID NO: 9.

42. A vector, or set of vectors, comprising, or together comprising, a cassette or set of cassettes according to claim 39, 40 or 31.

43. An isolated expression system comprising a vector or set of vectors according to claim 42.

44. The isolated expression system according to claim 43, which is a cell.

45. The isolated expression system according to claim 44, wherein the cell is a bacterium.

46. The isolated expression system according to claim 45, wherein the bacterium is an actinomycete.

47. The isolated expression system according to claim 46, wherein the actinomycete bacterium is a streptomycete.

48. The isolated expression system according to claim 47, wherein the streptomycete bacterium is *S. lividans*.

* * * * *

SEQUENCE LISTING

<160> NUMBER OF SEQ ID NOS: 65

<210> SEQ ID NO 1
<211> LENGTH: 2943
<212> TYPE: DNA
<213> ORGANISM: Artificial Sequence
<220> FEATURE:
<221> NAME/KEY: misc_feature
<222> LOCATION: (1) .. (2943)
<223> OTHER INFORMATION: n may represent a, c, g or t
<220> FEATURE:
<223> OTHER INFORMATION: Description of Artificial Sequence: Probe CK

<400> SEQUENCE: 1

```
catatgggta tgggtaatgc gtatccnctg gacatcgcag cacgggcggc caatctgacc      60
gaacggttac gggtcgtggc cgccgcgggc ggcgaggngg ccgtgcggga caccacggtc     120
gaactcgacg ccttcgaccg ctggaagacc gacacgctgg ccggaaaaant ggccgacaaa     180 ttccaccagg aatcgctgca ccgcggccgg ccgccccagc acaccaagga cgaactcgcn     240
ggcgtgctct ccgcctaccg ccgtctggaa ctcgccctgg acaccgcgga cgacgacgtc     300
cgggcacttc ncggcgagct gcagagcgcc tggctgccca cctaccgcgc ggccctcgac     360
gcccacgacg ccgcccgcga cngcgaacgc accgacgcgc aggcgggcga ggagcccggc     420
tggcgcgcgt tcgacgtgta ctacggccgg ctngccaagg cgtgcgagcc gttcctgcgc     480
gaactgggcc gcggcctgga ggccgcacgc ggcgccgcac aggncgagaa caccgcgctc     540
```

-continued

```
tccccgcaac tggccgagga catccagcgc cacctgctcg accgcttcga gctgngcgtg      600
gcctgggccg tggaggccga cgccaacgtg cactgcaccc aggccgggat cgacaaggcc      660
gaggcnacgc gcgaggacta cctcgcctac ctcgacacca cgttctccga cagcgccgcc      720
taccaccgct tctaccngaa gttcccggtg ctcggccgct ggctcgccca caccaccgcc      780
ctgctcaccg cgttcggccg cgacctcntc gacagcctgg ccgccgacgc gcaggccatc      840
ggcaccgagt tcttcgggca gccgatcacc gcgttcacnt ccctgcggct gggcgactcc      900 gaccccacg cgggcgcgcg caccgtcgcc cgcgtctccg tcgtgctcgn cgacgggcgc       960
accggcgagt tcttctacaa gccgcgcagc gtccggtccg aggcggcgct ccaggacgtc     1020
ntcgccaggc tggcggacga cggggtcgtc gacttcgcga cccggcccgt cctgccccgg     1080
gacggctacg gntacgaggc gctgatcccc gccggacgca accgcgtcga daccccggag    1140
gaggtcaccc ggatctaccg cgnactgggc ggctacctgg cgctgttcta cgtcctgggc     1200
ggcagcgacc tccacttcga gaacgtcatc gtcnccgacg dacacgcctt cgtctgcgac     1260
gccgagaccg tcctcggcgt ccacccccag ggacgggcac agtcngaggg caccctcctc     1320
gactccgtct tcaagaccgg actcctcgaa tggccgcgcg ccgcgagccc gggcgnggag    1380
gccgccgccg agatgcgcat cagcggctac gcgggcggcg agggatacga cgtccccgtc    1440
ccggagnccc gccgcacngg cgaggggntc agcttcgcgg cctccgtcgt gcacaagacc    1500
ggcgtccacg tcgagacnag cgcctccaac cgcgtctacc tcggcgagga gctcgtgcgt     1560
cccgaggacc acgtcgagtc gatcatgggg ggcttcaacc gcgtctacga ctggttcgcc     1620
gaggaccccg acgcgtccgt cgactacctg atggagacgn tcagctgggt caccgcccgc    1680
ttcatcaact ggggcaccca gatctacgcc cagctgctga gcgccgcccg ncacccgcgc    1740
tgcctcaccg aaccctcga agtggacctg ctcgccaaca ccgtccgcac cttcccccgc     1800
anctgggacg ccgaaggcgt cctggccgga cgggaagtgg ccgccatgtg gcagatggac    1860
gtgccgctgt tcnccgcggc cgcccacgcc cggcagctcg tccacgggca cagcgacccg    1920
ctgcccgccc ggctggacag ctcncccgatc gaccacgcgg ccgcacgcat ccggcggctg   1980
tcggagcgca accgcgaaca gcagagccag tacancgccg ccagcctctc gaccggcgag    2040
atcagcagcc ccgccttcgt cgccacctcc ctggactacg cggccnggat cggcaaccgt    2100
ctgtgcgacg agctgcgggc cccgccgcc tccgcccct ggacctccta ccagctntcc      2160
ggcgaatccc tcgccgaggt ggacatcgag gccgacctct accagggctc cgccggcgtc    2220
gtcctctncc tcgcctacct cgaccagctc gtgccccgcc ccgagtaccg caagaccgcc    2280
cggcaggccc tcgaccatnt cctcgtgcac tgggaccgcg accggctcgg cgccttcgcc    2340
ggactcggcg gcgtcgtcta cctcctcacn cacctgcacc gcctctgggg cgacgaggag    2400
ctcctcgacc tggcggtgcg gctcagcgac gagctgcccg nacgcatcga cgaggaccgg   2460
cacttcgaca tcctgcacgg cgcggccggc ctcatcccg tcctcctcgg cntcgcccgg     2520
gagaccggcg gccacggcat cgagcacgcc caccgctgcg ccgaacacct gctgcgccac    2580
gcngaggacg acggcaccac cctcagctgg ccccctccg cggccgacga dacgtacggc    2640
aacctcaccg gctnctcgca cggctccggc ggcatcggct gggcgctcat ccagctcggc    2700
cggcacaccg gcaggacgga ctacntcgag gccgggcgca aggcgttcgc ctacgaggac    2760
cggcacgtcg acgagcagga gaaggactgg tacganctgc ggatcaacaa cggatcctct    2820
agagtcgacc tgcaggcatg caagcttggc gtaatcatgg tcatagntgt ttcctgtgtg    2880
aaattgttat ccgctcacaa ttccacacaa catacgagcc ggaagcataa agtgtnangc    2940
```

```
ctg                                                             2943

<210> SEQ ID NO 2
<211> LENGTH: 4934
<212> TYPE: DNA
<213> ORGANISM: Artificial Sequence
<220> FEATURE:
<223> OTHER INFORMATION: Description of Artificial Sequence: pDWCC1

<400> SEQUENCE: 2
agatctacgc ccagctgctg agcgccgccc gccacccgag gtgcctgacc gagcccctcg      60
aggtggacct gctcgccaac accgtgcgca ccttcccccg cacctgggac gccgagggca     120
tcctcgccgc acgcgaagtg aacgccatgt ggcagctgga cgtgccgctg ttcaccgcgg     180
gcgcccatgc caggcagctg gtgcacgcgc acggcgagcc gctgtcctcg cgcctggacc     240
tctcgcccat cgaccacgcc gccgcccgca tcaggcggct gtcggaggag aaccgcgagc     300
agcagagcca gtacatcgcc gccagtctct ccacggacga gatcagcagc ccctccttcg     360
tcgccacttc cctggactat gcggtcaaga tcggcaaccg gctgtgcggc gagctcaggg     420
tgcccgagga ccccgcaccc tggacctcgt accagctggc gggcggccgg ctcgagcagg     480
tggacatcga ggccgacctc taccagggct ccgcgggcgt cgtgctcttc ctcgcctacc     540
tcgatcagct cgtgccccgg ccggagtacc ggcaggccgc ccggcagggc ctcgaccacg     600
tcctcgccca atgggaccgc gaccggctgg gcgcgttcgc ggggctcggc ggcgtcatct     660
acctcctcac ccacctgcac cggctgtggg gcgacaagga gctgctcgag aaggccgtcc     720
ggctgagcga cgagatcccc ggacgcatcg aggaggaccg gcacttcgac atcctgcacg     780
gagcggcggg cctcatcccc gtcctgatcg gcctcgccga ggagagcggc gggcacggcc     840
tcgaccacgc ccaccggtgc gccggccacc tgctgcggca cgccgaggac gacggcgaga     900
ccctcagctg gccgccgtcc gcgcccgacg agacctacgg caacctcacc ggcttctccc     960
acggctccgg cggcatcggc tgggccctga tccagctcgg ccaccacacc ggccggagcg    1020
actacatcga ggccgggcgc aaggccttcg cctacgagga ccgtacgtc gacgaggcgg    1080
agaaggactg gtacgacctg cggatcaaca acggctccgc ggtcaagggc gcccggcact    1140
tctccaacgc ctggtgcaac ggggcggccg gcatcgggct cgcccggatc accagctggg    1200
acgcgctcgg ccgcaccgac gaacaactgc tgcgcgaggc ccagcaggcg ctgtcggcga    1260
ccatgcgcaa cttccccccg gctgaagaacc acaccctgtg ccacggcacg tccggcaacg    1320
ccgagctctt cctgcgcttc gcccggctca cgacgaacc ggccttccag ctggaggcca    1380
acgtccaggt ccaggcgctg tggcggagct cgacgagc gggcgacagc acggcggaca    1440
acagtgccga cttcttcccg ggactgatga tcggcatctc cggattcggc atgcacttcc    1500
tgcggctggc ggccccggac cgcgtcccgt ccgtgctgct cctcgacccg ccgtcgcacc    1560
acgaacagta aggagtcgct ccaccatggc cctgaagacc tgcgaggaat tcctgcgcga    1620
cgccctcgac cccgaccgct tcggccggga gatgaaggcg gtcacggaga taccggagat    1680
cgtcaagctc ggccaccgcc acggatacgg cttcaccgcc gaggagttcc tgacgaaggc    1740
catgtccttc ggcgccccgc cggcggtgc cgcggcgcca ggggagagcg cgagcgtgcc    1800
ggggcagaac ggctcctcgc ccggccacgc cgcccgggcc gccatggccg cccggaggc    1860
cggcgccacc agcttcgccc actacgagta ccgcctggac gagctccccg agttcgcacc    1920
cgtcgtcgcg gagctcccca gctgaaggt catgccgccc tccgtcggac cggaccgctt    1980
```

-continued

```
cgccgcccgc taccgcgacg aggacatgcg gacgatctcg atgtccccg ccgaccccgc    2040
ctaccaggcc tggcaccagg agctcgccgg gcggggctgg cgggacgccg aggacacagc    2100
tgccgcaccg gacgcacccc ggcgggactt ccacctcctc aacctcgacg aacacgtcga    2160
ctaccccggc tacgaggagt acttcgcggc gaagaccagg gtcgtggcgg ccctggaaaa    2220
cctcttcggc ggcgacgtgc gctgctcggg ctccatgtgg tacccgccgt ccagctaccg    2280
gctgtggcac accaacgccg accagccggg atggcgcatg tacctcgtgg acgtcgaccg    2340
gcccttcgcc gaccccgacc ggacctcgtt cttccgctac ctccaccccg gcacccggga    2400
gatcgtcacg ctgcgcgaga gcccgcgcat cgtgcggttc ttcaaggtcg agcaggaccc    2460
ggagaagctg ttctggcact gcatcgccaa ccccacggac cggcaccgct ggagcttcgg    2520
ctatgtcgtg ccggagaact ggatggacgc cctccgccac cacggctgac cccgcacccg    2580
tcgccgcgcg caccgcgggg caccaaggag gagcgatgtt cggagcagga ccgcggaccg    2640
cgcgcaagcc ggcggcggac gacgggcccg cgcgcgagcc cgacgggccg gcgccggccg    2700
acgggaccgc ggccgggccc cggtccgcgc ggcccggccc gccggccatc ctggccagag    2760
ggctgggcaa gacgtacgcg ggcgtggaag cggtgcgcgg catcgacctg accgtcgccc    2820
agggtgagac cttcggcttc ctcggcccca cggggcggg caagaccacg acgatctcca    2880
tgctgaccac cctggccacg cccacctcgg gccggatcga gatcgccggc cacgacaccc    2940
gcaccgcccc ccagcaggtg cgccgcaacc tcgggctggt cttccaggag accacgttcg    3000
acccggagct gacggccgtg gagaacctgc gcttccacgc cgacctctac gccctgccgc    3060
gcgccgggct gagcgagcgc atcaccgcca tgctcgaact cgtcgggctc gcggcccgcg    3120
gcggcagcct cgtgcgcacc ttctccggcg gcatgcagcg ccggctggag atcgcacgcg    3180
ggctgctgca ccggccgcgg ctgctcttcc tcgacgagcc gaccatcggc ctcgacccgc    3240
agacccgggc ccaggtgtgg acgcacctgg ccgagatccg cgaacgcgag gccacgacca    3300
tcttcctgac cacgcactac ctcgacgagg ccgagcagtg cgaccgcatc gccatcatcg    3360
acgacggccg gatcgtcgcc cagggcagcc cggccgagct gaagtcggtc atcggggccg    3420
accgcgtgga cctgcgcacg ggtgacgacg tcgcggcggc cgcgctgctg cggacacgct    3480
tcggcctcga cccggtccag ggcccggccg gcctcagcgt caaggtcgcg gagggcgcca    3540
ggctcgtccc ggcgctgtgc gccgccctcg acgtggccgt ctacgaggtg accgtcaccc    3600
gccccagcct cgacgacgtc ttcctccacc acacggggcg cggaatccgc gacgactcag    3660
gagccggcgc atgacgcacg ccacggccgc actgccggcc gccgcccccc gcgaaaccgg    3720
ccgcatcgcc gccgaatggc gcgccggcac catggtgtgg cgacgcgaaa tgatccactt    3780
cctgcgctcg cgcgccggga tcgccgtgtc cctgctgcag ccgctgctgt tcctgtacgt    3840
gttgggcatc ggcctgtccc ggatgttcag cggcgccggc tcctccgacg actacatggt    3900
gttccttttc ccaggcgtgc tggtgatggc ggctcaggcc ccggccatct cggtgggcgc    3960
gtccatcgtc tgggaccggc agagcgggtt cctgcgcgag atgctggtgg cgcccgtcca    4020
ccgcagcacc ctgctgatcg gcaagtgcct cggcggcgcc accgtcgcgg cgtgccaggg    4080
cgcggtcgtc ctggccagcg ccgggctcgt gggtgtgccg taccggatcg acctcttcgc    4140
cgccctgctg gccgaactgc tcctcgcctc cctcgcgatg acggtcatgg gcgcggtgat    4200
cgcggtcagg atccagcgga tccagacgtt ccataccgcg ctgacggtcc tgacggcccc    4260
catggtcttc ctgtcggggc tgatgttccc cgtcagcgcc atgccggcct ggatggcctc    4320
gctcacccct gtcaaccccc tgacgtacgc ggtcgatgcc atgcggcaga cgatcaccgc    4380
```

-continued

| | |
|---|---|
| gttccacccc gccccggcgg ccgggcgtc gggggcaccg ttcttcgacc cggtctcctg | 4440 |
| gggaggctgg gacgtcccgc cggggctgtc ggtggccctg gtggccgcgt tctccgcggt | 4500 |
| ggctctggcg gtggccgcc gccgcttcgc acggaccgac tgaagtccca cgaagcgact | 4560 |
| gaaaacgccg tcgtcccggg cgacccaacc gtggatcatc gctcacgacc gtagcgccga | 4620 |
| accgatcaga ggagaccgca ccatgcgcac caccagacgc ctttcgctgc gccgccgtac | 4680 |
| cgctctgctc atgggcaccg cttcgctcgc ggccccgatg ctgctcacgg tccaggccgg | 4740 |
| cgaggcgcag gcgttcggca cgatcaactc gctcgggcag cgtgccgagc acgagcgcat | 4800 |
| caccgggcg gcgctcgcct gcgagcctgg ccaggcatcc gacgggacgt gtttcgagcc | 4860 |
| gcgctcgatc gaccaagtgg cgggccacac cggcacgttc ggggccgtgg gctcgcccga | 4920 |
| ctcggacgag atct | 4934 |

<210> SEQ ID NO 3
<211> LENGTH: 294
<212> TYPE: DNA
<213> ORGANISM: Artificial Sequence
<220> FEATURE:
<223> OTHER INFORMATION: Description of Artificial Sequence: Probe BB

<400> SEQUENCE: 3

| | |
|---|---|
| gcctacgagg accggtacgt cgacgaggcg gagaaggact ggtacgacct gcggatcaac | 60 |
| aacggctccg cggtcaaggg cgcccggcac ttctccaacg cctggtgcaa cggggcggcc | 120 |
| ggcatcgggc tcgcccggat caccagctgg gacgcgctcg gccgcaccga cgaacaactg | 180 |
| ctgcgcgagg cccagcaggc gctgtcggcg accatgcgca acttcccccg gctgaagaac | 240 |
| cacaccctgt gccacggcac gtccggcaac gccgagctct cctgcgcttc cgcc | 294 |

<210> SEQ ID NO 4
<211> LENGTH: 17083
<212> TYPE: DNA
<213> ORGANISM: Streptomyces cinnamoneus

<400> SEQUENCE: 4

| | |
|---|---|
| ggatcccggg ccgttcgccc agcacgagcc ccacacccag cgggaccgcg acgccgccga | 60 |
| gcgcgccgag gggggaaacc acgcccatga ggcccaggc cagggccttg tagaaggcga | 120 |
| gcatcgccgc cgggccgacg acgccggccg ccaccgcgta ccagagctgg ggcccggcct | 180 |
| cggaccagcc gccggtgccg atcacgatcg cgcccagggc gaggacggcc agcagctggg | 240 |
| agaccaggac cacggtcagg gcgggcatgc gccgggtgag cagcccgccg ccgaagtcgg | 300 |
| ccagcccca catgaggctg gtggccaggg cgaagaccgg tgtcatgggg gagacctcgc | 360 |
| agtacagtgt gatgaacggt ggcgtccacg acaccgtagt acacgatact cgacttacga | 420 |
| gaataatatt ttggacggga tggatcgacc gacgtgacgg acctcgacca gctcacgcaa | 480 |
| tcgctcgccc gcaacctcaa gcgctggcgc ggtgagcgcc acttcaccct cgacgccctg | 540 |
| gcggcccgct ccgcgtcag ccgcggcatg atcatccaga tcgagcaggc ccggacgaac | 600 |
| cccagcgtcg gcaccacggt gaagctcgcc gacgccctgg gcgtcagcat caccacgctg | 660 |
| ctcgactacg agcagggcgc ccgcgtgcgc ctcgtgcccg aggagcaggt ggtgcgcatg | 720 |
| tggtccaccg aggcgggcag ccacacctca ctgctcgtcg gcgccgatgt gcgcggccca | 780 |
| ctggagctgt gggactggcg cctcgtgtcc ggcgacagca gcgtctcgga cccccacccg | 840 |
| cccggcacgg tcgagatgct gaccgtacgg tcgggccgcc tcacgctcgt cgtcgacggc | 900 |

```
gaggagcacg aggtcgccgc cggcacctcg gccaccttcg aggccgacgc cccgcacacc      960
taccgcaacg acggcaccga gcccgtcgag atgacgatgg tggtggccgt cccgcccgcg     1020
ggctgacccc cgagcgcacg gggcccgccg ggagacgtcg agcgacgctc tcccggcggg     1080
cccctgtgcg tggtggctcc gtgcgccggt gaagacggtg ctcccgaagg cggtgctccc     1140
gaaggcggtg ttccgaaggc cggtgctccc gaagacggtg ctcctgaaag cggagtgaaa     1200
ccgtagtgaa agcggacgct cctagtgtcg ttctcaccgg gaaccgactg gatggggaaa     1260
cgggccatga aaagtgccaa ggaaccgacg atctaccagg acgtggatat catccgccgc     1320
atccaggagc tcatggttct gtgctccttg ctgccgcccg acggcaagct gcgtgaagcg     1380
ctggagttcg ctctctcgct ccacgaggag ccggtactgg cccggatcac tcccctcacc     1440
aatctccatc ccttcgcgac gaaagcctgg ctggagtccc tgtggctcgg cgacggcgtt     1500
tccagcgagg agaaggagct ggtcgcctgg cagaacaaca gcgacaacat gggaccggcc     1560
attcgtgaac tcaagaatgc cgaacagcaa tccggcatca ggctggtcgc acagctgacg     1620
tcctgacacc cgccgggtgc cgggattcac ctcaacatcg aggtaagcc atgaccgctt      1680
cgattcttca gcagtccgtc gtggacgccg acttccgcgc ggcgctgctc gagaaccccg     1740
ccgccttcgg cgcttccgcc gcggccctgc ccacgcccgt cgaggcccag gaccaggcgt     1800
cccttgactt ctggaccaag gacatcgccg ccacggaagc cttcgcctgc cgccagagct     1860
gcagcttcgg cccgttcacc ttcgtgtgcg acggcaacac caagtaagtg gctgctgcct     1920
ctaggcggta atgctcgccc ggtgcgatga cgcggtgggc cggtgacctg ccggcccacc     1980
gcgttgcgcc gcgcggcggc gcccctgcca cgagggtcac gaggctcctt cgacttcgac     2040
cgcaggagaa attcgcatat gggtatgggt aacgcgtatc cgctggacat cgcagcacgg     2100
gcggccaatc tgaccgaacg gttacgggtc gtggccgcgg cgggcggcga ggcggccgtg     2160
cgggacaaca cggtcgagct cgacgccttc gaccgctgga aggccgacac gctggccgga     2220
aaactggccg acaagttcca ccaggaatcg ctccaccgcg gccggccgcc ccagcacacc     2280
aaggacgaac tcgccggcgt gctgtccgcc taccgtcgtc tggaactcgg cctggacacc     2340
gcggacgacg acgtccggac gcttctcggc gagctgcaga gcgcctggct gcccgcctac     2400
cgtgcggccc tcgacgccca cgacgccgcc cgcgacgacg aacgggccga cgcacagccg     2460
ggcgaggagc ccggctggcg cgggttcgac gtgtactacg gccggctggc gaaggcgtgc     2520
gagccgttcc tgcgcgaact gggtcgcggc ctgggcgccg cgcgcgacgc cgcacagggc     2580
gaaggcgccg cgctctcccc gcagttggcc gaggacatcc agcgccacct gctcgaccgc     2640
ttcgagctga gcctggcctg ggccgtggag gccgacgcca acgtgcactg cacgcaggcc     2700
gggatcgaca aggccgaggc cacccgcgag gactacctcg cctacctcga caccacgttc     2760
tccgacagcg ccgcctacca ccgcttctac ctgaagttcc ccgtgctcgg ccgctggctc     2820
gcccacacca ccgccctgct caccgcgttc ggccgcgacc tcttcgacag cctggccgcc     2880
gacgcggagg ccatcggcac cgaattcttc gggcagcccg tcaccgcgtt cacctcgctg     2940
cgcctcggc actccgaccc ccacgcgggc gcgcgcaccg tcgcccgcgt cgccgtcgtg      3000
ctcgccgacg gacgcaccgg cgaattcttc tacaagccgc gcagcgtccg gtccgaggcg     3060
gcgctccagg acgtcctcgc caggctggcg gacgacgggg tcgtcgactt cgcgacccgg     3120
cccgtcctgc cccggacgg ctacggctac gaggcgctga tccccgccgg ccgcaaccgc      3180
gtcgagaccc ccgaagaagt cacccggatc taccgggaac tgggcggcta cctggcgctg     3240
ttctacgtcc tgggcggcag cgacctccac ttcgagaacg tcatcgtcgc cgacggacac     3300
```

-continued

```
gccttcgtct cgacgccga gaccgtcctc ggcgtccacc cccaggggcg ggcacagtcg    3360
gagggcaccc tcctcgactc cgtcttcaag accggactcc tcgaatggcc gcgcgccgcg    3420
agcccgggcg aggaggccgc cgccgagatg cgcatcagcg gctacgcggg cggcgagggc    3480
tacgacgtcc ccgtcccggt ggcccgccgc accggcgagg ggctcacctt cgcggcctcc    3540
gtcgtgcaca agaccggcgt ccacgtcgag accagcgcct ccaaccgcgt ctacctcggc    3600
gaggagctcg tgcgtcccga ggaccacgtc gagtcgatca tggagggctt caaccgcgtc    3660
tacgactggt tcgccgagga ccccgacgcg tccgtcgact acctgatgga gacgttcagc    3720
tgggtcaccg cccgcttcat caactggggc acccagatct acgcccagct gctgagcgcc    3780
gcccgccacc cgcgctgcct caccgaaccc ctcgaagtgg acctgctcgc caacaccgtc    3840
cgcaccttcc cccgcacctg ggacgccgag ggcgtcctgg ccggacggga agtggccgcc    3900
atgtggcaga tggacgtgcc gctgttcacc gcggccgccc acgccaggca actcgtccac    3960
gggcacggcg accgctgtc cgcgcgcctg gacagctccc cgatcgacca cgcggccgcc    4020
cgcatccggc ggctgtcgca gcggaaccgt gaacagcaga gccagtacat cgccgccagc    4080
ctctcgaccg gcgagatcag cagccccgcc ttcgtcgcca cctccctgga ctacgcggcc    4140
aggatcggcg accgcctgtg cgacgagctg cgggcccccg cggccccgc ccctggacc    4200 tcctaccagc tgtccggcga gtccctcgcc gaagtggaca tcgaggccga cctctaccag    4260
ggctccgccg gcgtcgtcct cttcctcgcc tacctcgacc agctcgtgcc ccgccccgcg    4320
taccgcaagg ccgcccggca ggccctcgac cacgtcctcg tccactggga ccgcgaccgg    4380
ctcggcgcct tcgccggact cggcggcgtc gtctacctcc tcacccacct gcaccgcctg    4440
tggggcgacg aggagctcct cgacctggcc gtgcggctca gcgacgagct gcccgcgcgc    4500
atcgacgagg accggcactt cgacatcctg cacggcgcgg ccggcctcat ccccgtcctg    4560
ctcggcctgg cccaggagac cggcggccac ggcatcgagc acgcccaccg ctgcgccgaa    4620
cacctgctgc gccacgccga ggacgacggc accaccctca gctggccccc ctccgcggcc    4680
gacgagacgt acgcaacct caccggcttc tcgcacggct ccggcggcat cggctgggcg    4740
ctcatccagc tcggccggca caccggccgg tccgactaca tcgaggccgg gcgcaaggcg    4800
ttcgcctacg aggaccggca cgtcgacgag caggagaagg actggtacga cctgcggatc    4860
aacaacggat ccgcggtcaa gggcgcccgt cacttctcca acgcctggtg caacggcgcg    4920
gcgggcatcg gcctcgcccg catcagcagc tgggccgcgc tcgaccgcag cgacgaacaa    4980
ctgctgcgcg acgcacagca ggccctgtcg gcgaccctcc ggaacttccc ccgcctgaag    5040
aaccacaccc tgtgccacgg cacctccggc aacgccgaac tcctcctgcg cttcgcccgg    5100
ctgagcgacg aacccgcctt ccagctggag gccaacgtcc aggtccaggc gctgtggcgg    5160
agcctcgacg aggccggcgg cggcgccggc ggggcagcg ccgacttctt cccgggactg    5220
atgatcggca tctccgggtt cggcatgcac ttcctgcgac tggcggcccc ggaccgcgtc    5280
ccgtccgtgc tgctcctcga cccgccgtcg caccacgaac agtaaggagt ggctccacca    5340
tggccctgaa gacctgcgag gaattcctgc gcgacgccct cgacccggcc cggttcgggc    5400
gcgagatgaa ggcggtcacg gaggtaccgg agatcgtcga gctcggccgc cgccacggct    5460
acggcttcac cgcggaggag ttcctgacga aggccatgac cttcgacggc acggcggcgg    5520
gcggcacggc cgcgggcggc ccggaggcgg cgggcaacaa ggccccccgg cagacccgc    5580 cccccgggac ccctgcgaac ggcgcgccgg caccggccac cgccaccagc ttcgcccact    5640
```

-continued

```
acgagtaccg tctggacgac ctcccggagt tcgcgcccgt cgtggccgag ctgccccggc    5700
tcaaggtcat gccaccctcc gcccgcctgg accggttcgc cgggcacttc cgcgaggagg    5760
acgcccggac cgtctccacc tcgcccgccg accccgccta ccaggcatgg caccgcgacc    5820
tcgccgcgcg gggctggcag gacgagggcg ccgcgcccgg cgccccgcgc cgcgacttcc    5880
acctcgtcaa cctggacgaa cacgtcgact acccgggcta cgaggactac ttcgccgcga    5940
agacgcgggt cgtggccgcc ctggagaacc tcttcggcgg cgaggtgcgg gcctcgggct    6000
ccatgtggta tccgccgtcg agctaccggc tctggcacac caacgcggac cagccgggat    6060
ggcgcatgta cctggtggac gtggaccggc ccttcgccga ccccgccag acctccttct    6120
tccgctacct ccacccgcgc acccgcgaga tcgtcaccct caccgagagc ccgcgcatcg    6180
tgcgcttctt caaggtggag caggacccgg agaagctctt ctggcactgc atcgccaacc    6240
ccacggaccg gcaccgctgg agcttcggct acgtcgtgcc ggagacctgg atggacgccc    6300
tccgccacca cggctgaccc ggcacccgtc gtccgcgcac cgcgcggcac caaggaggag    6360
cgatgttcgg agcaggaccg cggacggcgc gggggcccgc ggcggggacg gacggcgacg    6420
ccgcccaccg aagcggccgg ccggcaccgg ccgccggggc cgctggcggc ccgacggccg    6480
ggtccggtcc gccggccgtc ctggcgcggg ggctgggcaa gtcgtacgcg ggagtggaag    6540
ccgtgcgcgg catcgacctg accgtcgccc agggcgagac cttcggcttc ctcggcccca    6600
acggggcggg caagaccacg acgatctcga tgctgaccac cctgccacg cccaccacgg    6660
gccggatcga gatcgcgggc cacgacaccc gcaccgcacc ccagcaggtg cgccgcaacc    6720
tcgggctggt cttccaggag accacgctcg acccggagct gacggccgtg gagaacctgc    6780
gcttccacgc cgacctctac gcactgccgc gggccggcct ggccgggcgc atcgccgaga    6840
tgctggagct cgtcgggctc tccgcccgcg gcgacagcct cgggcgcacc ttctccggcg    6900
gcatgcagcg ccgcctggag atcgcccgcg gcctgctgca ccggccgcgc ctgctcttcc    6960
tcgacgagcc gaccatcggg ctcgacccgc agacccgcgc ccaggtgtgg gcgcacctgg    7020
ccgaggtccg cgagcgcgag gcgacgacca tcttcctcac cacgcactac ctcgacgagg    7080
ccgagcagtg cgaccgcatc gccatcatcg acgacgccg atcgtcgcc cagggcagcc    7140
cggccgagct gaagtccgtc atcggcgcgcg accgggtgga cctgcgcacc ggtgacgaca    7200
tggccgcggc cgccctgctg cacgagcgct tcggcctggc ggcggtccgg ggcccgaacg    7260
gcctgagcgt caaggtcgcg gaaggcgccc ggctcgtccc ggcgctgtgc gccgccctcg    7320
acgtggccgt ctacgaggtg acggtcaccc gccccagcct cgacgacgtc ttcctccacc    7380
acacggggcg cggcatccgt gacgacgccc tgcccggcgc ggcgggcacg gcaggcacag    7440
ccgaaccgtc ggactcagga gacagcacat gacgcacgcc acgtcgccc tgcccgcggc    7500
cgaccgccac gccccggcc ggctcgccgc cgaatggcgc cgggcagca tggtgtggcg    7560
gcgcgaaatg atccacttcc tgcgctcgcg cgccgggatc gccgtctccc tgctgcagcc    7620
gctgctgttc ctctacgtgc tgggcatcgg cctgtcccgg atgttcagcg cgccggctc    7680
gtcggacgac tacatgatct tcctcttccc cggtgtgctg gtgatggcgg cacaggcccc    7740
ggcgatctcg gtgggagcct cgatcgtctg ggaccggcag agcggcttcc tgcgcgagat    7800
gctggtggcc ccgtccgcc gcagcaccct gctgatcggc aagtgcctgg gcggcgccac    7860
cgtcgccgcc tgccagggcg cggtcgtcct ggccagcgcg ggcctggtgg gcgtgcccta    7920
ccgcgtcgac ctcttcgccg ccctgctggc cgaactcctg ctcgcctccc tggcgatgac    7980
ggtcctcggc gcggtgatcg ccgtgcggat ccagcggatc cagacgttcc acacagcgct    8040
```

```
gaccgtcctg acggcaccga tggtcttcct gtcggggctg atgttcccg tcagcgccat    8100
gccggcctgg atggcggcgc tcaccctggt caaccccctg acctacgccg tggacgccat    8160
gcgtcagacg atcacggcct ccacccccgc gcccgcggcc ggggcatcgg gtgcgcccat    8220
cttcgacccc gtctcctggg gcggctggga cgtaccgccg ggcctgtcgg tggtgctggt    8280
ggccgtgttc tcggccctgg ccctggcggc ggcctcccgg cgcttctccc gcaccgactg    8340
acggcgttcg cggaccgact gaaaacaccg tcgttcccac gcgtccaacc gtggatcatc    8400
actcacgtcc agcgcccgga ttcacatctg aggagacatc accatgcgta gcaccagacg    8460
cctttcgtta cgtcgccgtt ccgccctgct gatgggcgcc gcctccctcg cggcgccggc    8520
gctgctgacg gtccaggccg cgcaggcgca ggcgttcggc acgatcaact cgctgggcca    8580
gcgcgccgag cacgagcgca tcacccgggc ggcgctggcc tgcgccgccg gcacgtcgtc    8640
cgacggatcg tgcttcgagg cccggtcgat cgatcaagtg gccggtcaca cggggacgtt    8700
cggggccgtc gggtcgccgg actcggacga gatcttcacc cccgaggcgc actgcgacga    8760
cgccgactac ctcacggcct ccggctaccg gcgcacccgt cagcaggcca gcgaccagct    8820
cgtcgcctgc atatccaagc tgcagggacg tttcagccag ggcgtcgccg ccggctcggg    8880
cacccctgaac ggggacggca cggtctcccc gggcaacagc gacctgtccc aggactgcac    8940
cttcaccggc ggcgtccccg ggcgcggcaa gtgcaacgcc atcgagggct cggccgggc    9000
cctgcacggt gtgcaggact tctactcgca cagcaactgg gcggacaagg cggaccccaa    9060
ccaggccgtg ggcgtcaaca cccgcccggg cctcaacatg tcgggcccg ccccactgct    9120
ctcgctcaag agcggccgcc ctccggcggc ctcctcggtg ccggcgcagc tgtccacggg    9180
ctgtttctcg ctcaacccct ggggctgctc gggccgggtg acccacagca ccctcaacaa    9240
ggacaccggc ctgatcgacc cggccagcgg cgccaccagt gacccgacga cgaaccgcgg    9300
caggatcacc ggcaacttcg accgcgccgt caagggtgcc attgccgaca cccgccgtca    9360
gtgggccgac ttccggaccg cgctgaccga gcgctacggc caggagcgcg ccagcgcat    9420
cgcctgcgtc ctgacgcacg acaacccgt gcgcgactgc cgctgatccc tcgcggcccc    9480
gcgtcccgcc ggcccggtgc tccgcgccgg gccggccggc acgcaccgga ccggtcctcg    9540
cgggtcaggc gtcgccgtac gcctcgccgc cgagctccag cacggccgtc ccggcggtgg    9600
tgtccgccag ccaggcccgg aacccctcga cgtcggcctc gggcagcccg atcccgatgc    9660
gcacgccctc gccgtaggcc acctcgcgca cctcgcgccc ggtggcccgc aggtcgttct    9720
gcagcttccc ggcccgctgg tggtcgaccg tgaccgtggc cagccggaag cgcttgtggg    9780
tcaccgtgcc gagctcgtcg agggcctcgc cgaccactcc gccgtacgcc cggatcagac    9840
cgcccgcgcc gagcttgacg ccgccgaagt agcgggtgac gaccgccacg acgtagcgca    9900
tgtcgcgccg gaggagcatc tgcagcatgg gcacgcccgc ggtgccccg ggctcgccgt    9960
cgtcgctggc cttctggacc gagccgtcgg cgccgaggac gtacgcccag cagtggtgcc    10020
gcgcggtcgg gtgctccttg cggatgcgcg cgaggaacgc ctgcgcctcc tcctcggtgg    10080
cggcgggcgc gagcgcgcag atgaagcgcg acctgctgat ctcgatctcg tgcacgcctt    10140
cgagcgcgac cgtgcggtac tcgtcctgca ttccgccagc ctagacgtct ccgcggcgcc    10200
gcccggaccc gggaatggtc cggcgaccta gatcgttgag ccggcatgtt cgcagaaccg    10260
gggatcatcc agaagatcat cgaggggacc ggcgacacct gggcgctggt cggcctctcc    10320
gccaacgagc agcgcgccgc gtacggcgtc gccgaggtgc tccagcgcca cggcaagcgc    10380
```

```
atcgttcccg tccaccccaa ggccgagacg gtccacggcg agctgggcta cgcctccctc   10440
gccgacatcc ccttcgacgt cgacgtcgtg gacgtcttcg tccggtccga gctcgcgggt   10500
gccgtcgcgg acgaggcggt agagatcggc gccaaggccg tctggttcca gctcggggtg   10560
atcgacgagg aggcgtacga ccgcacgcgc ggggcgggcc tgctgatggt catggaccgc   10620
tgcccggcga tcgaactcgg ccggccgcgg ggacgggcgg tctgacatct tcctgcgaag   10680
gtctccgcga acggttgtgc gaccatgccg gattcccttg aatgtgctc  ctcagtcctt   10740
ttggtcaagg agtacagatg cgcaagtccc ttgctgttgc ggccgcttcg gcggttgccg   10800
gcctcacgct gatggccggc accccggcga acgcggcgcc ggccgccgcc accaccgtac   10860
cgagctgtgt gacgtctacc ttctcgacgc cgttcttcgc gatggtccgc gtcgacatgg   10920
agaacaagtg caccaccgag cagcgggtga agccgtcgtt caactacgag ctgaaggacg   10980
ttccgtgcta cgccctgcag cccggtcaga aggcggtgtt cagccgggac gtgatcttcg   11040
cctccgggta cacgttcgcc ggcctcgtca gctgctgaca cccggcccgt agcggtcacg   11100
gctcacaccg tcacaccgtc agtcccgcgt cgcgggcgca cagcgccgcc tgcaccctgt   11160
tgccgacctc cagggcggcc aggatgcggc tgacgtgagc cttgaccgtg ctctcccgca   11220
tgcccaggcc gtcggcgatc tccgcattgg aggcgccggc ggccaggagc ccaggacgt   11280
ccgactcgcg gggggtcagc cgcgccaggc gctgctgggc ggcttggaca tcgcgggacg   11340
ccgtgcggtg gtagcggtcg accagacggc gggccgcggc ggggtggagc atggcctggc   11400
ccgccgcgac gacctgtatc gcccggatga tctcggccgg atcggtgtcc ttgaggagga   11460
agcccgaggc gccggccgcc agcgcgtcgt acacgtactg gtcgaggtcg aacgtggtca   11520
gcatgacgac ttccggcggg ctgggcagcg cgcgcagccg ctcggtggcc gctatcccgt   11580
ccatgcgcgg catccggacg tccatcaggg ccacgtccac gcgcagggca ccggcccgct   11640
ggacggcttc gaggccgtcg cccgcctgtg ccacgacctc aatgccgggg acgtcgtcga   11700
ggatgtcggc gagggccagc cggaccaggc tgtcgtcgtc gacgatcaat gtacggatca   11760
tgccgctccc ggcgcgaggt gttcttcgac agtgctgacg gggatgtcgg cggcgatgtt   11820
ccagccaccg ccccccgaag gtccgtagtc cagccggccg cccagcgccg tgacgcgctc   11880
ggccagtccg accagcccgt agccgctgct gaccggcggc tccccggcgg cggacgccgg   11940
gtcgccggcg cggttgtgca cctcgacgct ggaggccggg ggaccgtagc gcacgacgac   12000
ccgcacgggg gccccgggag cgtgcttgcg ggcgttggtc agcgcctcct gcaccagccg   12060
gtggacggcg aggcggtgac tggccgggag cggcccggcc gcgccctcga cgaccgcgtc   12120
gatctcctgg ccggccgcgc gcgcctcgtc gaagagggcg ggcagctcgc gcagccccgg   12180
gacgcgctgc ccctgcagct ccgggtggtc gggatcgcgc aggacgccca ggacgtcccg   12240
caggtcgccc agggcctcgg tggaagtggt gcgcagcagt gcgagccggt ccgccacggg   12300
ctcgggaagg gtggcggccc gccgctgcag ggctccggcg tgcagggcca gcaggctcag   12360
ccggtgggcg agcacgtcgt gcatctcggc ggcgatgcgg gccgttcgc  tcagccgcgc   12420
ctgcttggcg cgcagctcgc gctcgacgcg caggtgctcg acctgcgccg tcaggctcgc   12480
ctccagccgc ctacggctgt ccgcccacag ccccagcacc atgacgaggg cgaacggcag   12540
cacggggccg tacgcacggg tgctccacag caactgctcc ggctgcgcga accagttgcc   12600
ggccagcgcc accgcggcac acgcacagcc cagcgcgcgc cacccgcgcg aggcgaggta   12660
gaagagcatg accagcaggg gcagcagggc gcccaccacg accgcggcgc agacggtcac   12720
caccaccgtg accaacggga cgcggtagcg caccgccaag gagaggctgc cgacggcggc   12780
```

```
gacggccgtg tccgggcccc acagcgtggc gccggccccc acgtaggcgt tctgtacggc   12840
cagcacaccc acggcggcga ccagcagcgc ctccgcccat cccggccacc ttcggtcgtc   12900
cgcactcagc acgggtaaat cgtagtcacc caccgttttt gatccctccg ccagtcggcc   12960
tacgctaccc cctactttcg taccgatcga gcgtcgcaca acggccgatg gtgcgccccg   13020
cggcggcccc tagtttcatg gtcatggatc tgacgcaagc caactccacg cccgtacagc   13080
cgcgttcggc caccgggctg gccttcctcc gcgaggcgac ccgcaccttc cgcaccaccg   13140
gcgcgatcgc gccgagcagc cggcagctcg ccgagcggct ggccgcgccc ctcgcccctg   13200
cgagcagact gcgccggccc accgcggtgc tggaggtcgg cgccggcacg gggccggtga   13260
cccgggttct ggccggtgcc gtgggccccg ccgaccggct cgacgtcgtc gagatcaacc   13320
cccgcttcgt cgagatcctc aacggcgccc tgcgcacgga ccccgccatg tcggcggcct   13380
cggaccgcat ccggatcatc cccgagtcga tcaccgagat gcccatcgac acagctacg   13440 acgtcgtcgt ctcctgcctg ccgttcacca acttcgcgcc ggagacggtc aggtccatcc   13500
tggaccgcta cctgtcggtg ctcgtgccgg gcggacacct gacgttcttc ggctacctcg   13560
gcacccacgc caccgctcg ctgctcagca gccggaagga ggccgcccgc caccgcgaag   13620
tgaccgacct gctgcacgac ttcacccgcc gctacgccag ccggcagagt gtcgtgtggc   13680
gcaacatccc gcccgcccgg gtgtggcacg tgcgcgcccc cgagcacgcc acccgggcgg   13740
cggacgccgc ctgatgccca ccgcggacga gctgttgcac ggagtgccgc ccgcggccgc   13800
gtacggtctc gtgctcggcc tggtgctcct cgaatcggtg ctgctgctcg gttcgttcgt   13860
gcccacgctc agcctgatgc tgtgcgccgg ggtcctggca caggagggaa cgctgcggct   13920 gccctggtg gtgctgtgcg ccacgacggg ggtggtggcc ggtgacctgc tcgcgcagcg   13980
caccgggcgc cgcctcggcc ccggcctgcg gcgctcccgg ctggggaggc ggctgcccga   14040
ggcggcctgg gagcgcgcct ggtcggtgct ccagcgccgc ggcggccccg cgctgctggt   14100
ctgccgcttc gtgccggtcg tgcggacctt cgcgccgcac ctggcgggcg ccgccggcat   14160
gccgtaccgg cggctggccc cgtacagcct ggtggcgggc ctggtctggg cgggcgggga   14220
agccggtgcg ggatacgtgc tgggcgcctc ctacgaccgg ctgaccgcgc cgggcggcgg   14280
gctgcccacg gtctgcgccg ccgccggcgt cctgctggcg cagcggcgg ggctgctcgt   14340 gcaccgccgg cgcgcgcgcc gggcggtggg cggctcaggc cgagcgggcc agcgacaggc   14400
tgacgtcggt gcgcaggatc gcgacgtgca gatgacgcag ctcgcgcccg gggtccaccc   14460
cgagctcgtc gcggaagacg ccgctgacct ccgcgtacgc ggccagggcc tcgcccctgc   14520
ggccgcagcg gtagagggcg agcatcagcc gctgccacag gctctcgcgc agcgggtact   14580
tcgcggtcag cgtccgcagg tcgccgacga tctcgtcgtg gcggccgagg gcgaggcagg   14640
cgtcgtggta gcgctcgatg gcccggatcc actcctccat cagccccggc accacgtccc   14700
ggtggagcgc gtccgagcgc acgccgccga gcggctggcc gtgccagagg gccagtgcct   14760
cggtgagggc ggagtgctcc agtgcgcggt cgccgagctc ggcggcgagc cgggcgcggg   14820
cggcggattc acggaaaaga gtgagatcca gacagccggt ggggacctcg atcaggtaac   14880
cgctgggcga ggtgtgcagc agtccggaga gccccgcgcc ggctgcgtcc aggtctgtc   14940 gtaagcgggt gaggagggtg tgcagggcgg ggcgcgggct gtgcggcagc tcgtcgcccc   15000
acaccaggtc cacagagttc tcgacccgga cgatctcgcc cgggtgcacg agcagggccg   15060
ccaggaggga ccgttgccgg ccgctgggta gcgaaacgtt tttcctgccc accgtgacgc   15120
```

```
tcagtggtcc gagaactcgg aaggatattg cccggttcat gaactctccc cttcgctcat    15180
cgagccgcac cctgaagacg gctggggact gccgtgtccg ctgtccactc aagcggacgt    15240
cgcggtcagc aagcgtacgg tgcgtacaga gttggttgtc aactatggcg tatgaatgtc    15300
agggttgtct ggcgttatcc atacgctcaa gcggacagaa acagtcgacc gggcaacaac    15360
tcccggggga gggacggggc atgagcgaca gtcgaccggc accggaccgc aacgaccggc    15420
cacttctgcg ccagttcgac cagcggctca gtgaactgat cgccaccacc gccggggccg    15480
aggggaacaa gcgccccgga tacgcgcgcc tggccaagga gatccgcgac accaccggcc    15540
ggaccatctc cggcacctac ctgtgggagc tggccaccgg gaagaagcgc aacgtcacgc    15600
tcgaacagct cgacgtcctc gcggagttct cggtgtgcc cccggagtac ttcctcgacg    15660
acgagaccgg ccgccgcatc gacgaccgcc gaagactggc catcgccctg cgcgacgcca    15720
aggtgcgcaa cctcgccctg cgcgcggacg ggctctcgcc cgactgcctg gacgcgctga    15780
tcgccatggt gaacgaggcg cgcaagacc agaacctgtc gtccatcgac gatgacgacg    15840
acaccgccac caccct tact tcttcagggt agtcaacgac ccgacgccgg tcccgtgggc    15900
ctggaggacc gatgccacgc cgtacgtacg tcgcctaccg ccgctgcctg agaaagggtc    15960
aacgggaacc cgagatgccg tacacgagcg acgccgccct ccgtcgacgc tgccgggccc    16020
tgctggcccg cgtcagcctg cccgagccgt tctccgtcga gtcctgtgc cggcacctcg    16080 gcgaacagcg cggccggccc atccacctgc acccgctgcc ggaacaggcc gccctggccg    16140
gggcctgcgg cctgtggctc gccaccgcca ccgacgacca catcttccac gagcgccaca    16200
ccgtccgccc gcaccaggag cacatcgtcc tccacgagat cggccacatg ctcttcgacc    16260
accactcgct ggccccggcc ggcggccggg cgggcgccct cctggccgac ctcgaccccc    16320
ggctcatccg ccgtctcctc gcgcgcacca actactccac gcgccaggaa cgcgaggcgg    16380
agatgctcgc cagcctgatc cgcaccagcg tccgcgccgg caccggggaa cggccgccgg    16440
gcgcgctggg ccggctgcag gcggcgctgg gcgtggtcgg gtcccatggc cgctgacgtc    16500
ctcgattccg tcctggggac caccgggctg gtgtgcctgt ggaccgcggt ggtcctgcga    16560
tgtccctacg ccgtgcgcca ccccgcacag cgcggactgt ggctggcggt ggccacggcg    16620
gccctggcga tgaccctcac cacctccatc ggctccgtcg tccccgaagc ggcgctcggg    16680
ctcgccggca acctcaccgg catggtctcc gcgggcgccc tcctcggctt cgtcatcacg    16740
atcatgggcg ggcggcgcct gcacacctgg gcctgcggca cggtcgccgc cacgccctc    16800 gccctgaccg tcctcggcgt cacctcccgg gcccacctct cctacggcac catcgccgag    16860
atcccgccca ccgccaccgc ctaccggctg ctgctgatcg gcacccacct ggccgtgaac    16920
gcggcctgca tcgcggtgtg ctggcggtac gggagggggc ccagccgctc cccgctcgcc    16980
ctcggcctgc ggctcttcgg catcggcacc gtcctggcgg agctgtactg gctgcgcctg    17040
ttcgccggcc tcttcaccac ctccgacgcc ctcctgcggt acc                     17083
```

<210> SEQ ID NO 5
<211> LENGTH: 1135
<212> TYPE: DNA
<213> ORGANISM: Artificial Sequence
<220> FEATURE:
<223> OTHER INFORMATION: Description of Artificial Sequence: Probe 1.1

<400> SEQUENCE: 5

```
ctgcagccgc tgctgttcct ctacgtgctg ggcatcggcc tgtcccggat gttcagcggc    60
gccggctcgt cggacgacta catgatcttc ctcttccccg gtgtgctggt gatggcggca   120
```

-continued

```
caggccccgg cgatctcggt gggagcctcg atcgtctggg accggcagag cggcttcctg      180
cgcgagatgc tggtggcccc cgtccgccgc agcaccctgc tgatcggcaa gtgcctgggc      240
ggcgccaccg tcgccgcctg ccagggcgcg tcgtcctgg ccagcgcggg cctggtgggc       300
gtgccctacc gcgtcgacct cttcgccgcc ctgctggccg aactcctgct cgcctccctg      360
gcgatgacgg tcctcggcgc ggtgatcgcc gtgcggatcc agcggatcca gacgttccac      420
acagcgctga ccgtcctgac ggcaccgatg gtcttcctgt cggggctgat gttccccgtc      480
agcgccatgc cggcctggat ggcggcgctc accctggtca ccccctgac ctacgccgtg       540 gacgccatgc gtcagacgat cacggccttc accccgcgc ccgcggccgg ggcatcgggt       600
gcgcccatct cgaccccgt ctcctggggc ggctgggacg taccgccggg cctgtcggtg       660
gtgctggtgg ccgtgttctc ggccctggcc ctggcggcgg cctcccggcg cttctcccgc      720
accgactgac ggcgttcgcg gaccgactga aaacaccgtc gttcccacgc gtccaaccgt      780
ggatcatcac tcacgtccag cgcccggatt cacatctgag gagacatcac catgcgtagc      840
accagacgcc tttcgttacg tcgccgttcc gccctgctga tgggcgccgc ctccctcgcg      900
gcgccggcgc tgctgacggt ccaggccggc gaggcgcagg cgttcggcac gatcaactcg      960
ctgggccagc gcgccgagca cgagcgcatc cccggcgg cgctggcctg cgccgccggc       1020
acgtcgtccg acggatcgtg cttcgaggcc cggtcgatcg atcaagtggc cggtcacacg      1080
gggacgttcg ggccgtcgg gtcgccggac tcggacgaga tcccccgggc tgcag           1135
```

<210> SEQ ID NO 6
<211> LENGTH: 114
<212> TYPE: PRT
<213> ORGANISM: Streptomyces cinnamoneus

<400> SEQUENCE: 6

```
Met Thr Pro Val Phe Ala Leu Ala Thr Ser Leu Met Trp Gly Leu Ala
 1               5                  10                  15

Asp Phe Gly Gly Gly Leu Leu Thr Arg Arg Met Pro Ala Leu Thr Val
            20                  25                  30

Val Leu Val Ser Gln Leu Leu Ala Val Leu Ala Leu Gly Ala Ile Val
        35                  40                  45

Ile Gly Thr Gly Gly Trp Ser Glu Ala Gly Pro Gln Leu Trp Tyr Ala
    50                  55                  60

Val Ala Ala Gly Val Val Gly Pro Ala Ala Met Leu Ala Phe Tyr Lys
65                  70                  75                  80

Ala Leu Ala Leu Gly Pro Met Gly Val Val Ser Pro Leu Gly Ala Leu
                85                  90                  95

Gly Gly Val Ala Val Pro Leu Gly Val Gly Leu Val Leu Gly Glu Arg
            100                 105                 110

Pro Gly
```

<210> SEQ ID NO 7
<211> LENGTH: 190
<212> TYPE: PRT
<213> ORGANISM: Streptomyces cinnamoneus

<400> SEQUENCE: 7

```
Met Thr Asp Leu Asp Gln Leu Thr Gln Ser Leu Ala Arg Asn Leu Lys
 1               5                  10                  15

Arg Trp Arg Gly Glu Arg His Phe Thr Leu Asp Ala Leu Ala Ala Arg
            20                  25                  30
```

```
Ser Gly Val Ser Arg Gly Met Ile Ile Gln Ile Glu Gln Ala Arg Thr
            35                  40                  45

Asn Pro Ser Val Gly Thr Thr Val Lys Leu Ala Asp Ala Leu Gly Val
        50                  55                  60

Ser Ile Thr Thr Leu Leu Asp Tyr Glu Gln Gly Ala Arg Val Arg Leu
65                  70                  75                  80

Val Pro Glu Glu Gln Val Val Arg Met Trp Ser Thr Glu Ala Gly Ser
                85                  90                  95

His Thr Ser Leu Leu Val Gly Ala Asp Val Arg Gly Pro Leu Glu Leu
            100                 105                 110

Trp Asp Trp Arg Leu Val Ser Gly Asp Ser Ser Val Ser Asp Pro His
        115                 120                 125

Pro Pro Gly Thr Val Glu Met Leu Thr Val Arg Ser Gly Arg Leu Thr
    130                 135                 140

Leu Val Val Asp Gly Glu Glu His Glu Val Ala Ala Gly Thr Ser Ala
145                 150                 155                 160

Thr Phe Glu Ala Asp Ala Pro His Thr Tyr Arg Asn Asp Gly Thr Glu
                165                 170                 175

Pro Val Glu Met Thr Met Val Val Ala Val Pro Pro Ala Gly
            180                 185                 190

<210> SEQ ID NO 8
<211> LENGTH: 29
<212> TYPE: PRT
<213> ORGANISM: Streptomyces cinnamoneus

<400> SEQUENCE: 8

Met Lys Thr Val Leu Pro Lys Ala Val Leu Pro Lys Ala Val Phe Arg
1               5                   10                  15

Lys Ala Val Leu Pro Lys Thr Val Leu Leu Lys Ala Glu
            20                  25

<210> SEQ ID NO 9
<211> LENGTH: 119
<212> TYPE: PRT
<213> ORGANISM: Streptomyces cinnamoneus

<400> SEQUENCE: 9

Met Lys Ser Ala Lys Glu Pro Thr Ile Tyr Gln Asp Val Asp Ile Ile
1               5                   10                  15

Arg Arg Ile Gln Glu Leu Met Val Leu Cys Ser Leu Leu Pro Pro Asp
            20                  25                  30

Gly Lys Leu Arg Glu Ala Leu Glu Phe Ala Leu Ser Leu His Glu Glu
        35                  40                  45

Pro Val Leu Ala Arg Ile Thr Pro Leu Thr Asn Leu His Pro Phe Ala
    50                  55                  60

Thr Lys Ala Trp Leu Glu Ser Leu Trp Leu Gly Asp Gly Val Ser Ser
65                  70                  75                  80

Glu Glu Lys Glu Leu Val Ala Trp Gln Asn Asn Ser Asp Asn Met Gly
                85                  90                  95

Pro Ala Ile Arg Glu Leu Lys Asn Ala Glu Gln Gln Ser Gly Ile Arg
            100                 105                 110

Leu Val Ala Gln Leu Thr Ser
        115

<210> SEQ ID NO 10
```

-continued

```
<211> LENGTH: 78
<212> TYPE: PRT
<213> ORGANISM: Streptomyces cinnamoneus

<400> SEQUENCE: 10

Met Thr Ala Ser Ile Leu Gln Gln Ser Val Val Asp Ala Asp Phe Arg
 1               5                  10                  15

Ala Ala Leu Leu Glu Asn Pro Ala Ala Phe Gly Ala Ser Ala Ala Ala
                20                  25                  30

Leu Pro Thr Pro Val Glu Ala Gln Asp Gln Ala Ser Leu Asp Phe Trp
            35                  40                  45

Thr Lys Asp Ile Ala Ala Thr Glu Ala Phe Ala Cys Arg Gln Ser Cys
 50                  55                  60

Ser Phe Gly Pro Phe Thr Phe Val Cys Asp Gly Asn Thr Lys
 65                  70                  75

<210> SEQ ID NO 11
<211> LENGTH: 1088
<212> TYPE: PRT
<213> ORGANISM: Streptomyces cinnamoneus

<400> SEQUENCE: 11

Met Gly Met Gly Asn Ala Tyr Pro Leu Asp Ile Ala Ala Arg Ala Ala
 1               5                  10                  15

Asn Leu Thr Glu Arg Leu Arg Val Val Ala Ala Ala Gly Gly Glu Ala
                20                  25                  30

Ala Val Arg Asp Asn Thr Val Glu Leu Asp Ala Phe Asp Arg Trp Lys
            35                  40                  45

Ala Asp Thr Leu Ala Gly Lys Leu Ala Asp Lys Phe His Gln Glu Ser
 50                  55                  60

Leu His Arg Gly Arg Pro Pro Gln His Thr Lys Asp Glu Leu Ala Gly
 65                  70                  75                  80

Val Leu Ser Ala Tyr Arg Arg Leu Glu Leu Gly Leu Asp Thr Ala Asp
                85                  90                  95

Asp Asp Val Arg Thr Leu Leu Gly Glu Leu Gln Ser Ala Trp Leu Pro
            100                 105                 110

Ala Tyr Arg Ala Ala Leu Asp Ala His Asp Ala Ala Arg Asp Asp Glu
        115                 120                 125

Arg Ala Asp Ala Gln Pro Gly Glu Glu Pro Gly Trp Arg Gly Phe Asp
    130                 135                 140

Val Tyr Tyr Gly Arg Leu Ala Lys Ala Cys Glu Pro Phe Leu Arg Glu
145                 150                 155                 160

Leu Gly Arg Gly Leu Gly Ala Ala Arg Asp Ala Ala Gln Gly Glu Gly
                165                 170                 175

Ala Ala Leu Ser Pro Gln Leu Ala Glu Asp Ile Gln Arg His Leu Leu
            180                 185                 190

Asp Arg Phe Glu Leu Ser Leu Ala Trp Ala Val Glu Ala Asp Ala Asn
        195                 200                 205

Val His Cys Thr Gln Ala Gly Ile Asp Lys Ala Glu Ala Thr Arg Glu
    210                 215                 220

Asp Tyr Leu Ala Tyr Leu Asp Thr Thr Phe Ser Asp Ser Ala Ala Tyr
225                 230                 235                 240

His Arg Phe Tyr Leu Lys Phe Pro Val Leu Gly Arg Trp Leu Ala His
                245                 250                 255

Thr Thr Ala Leu Leu Thr Ala Phe Gly Arg Asp Leu Phe Asp Ser Leu
            260                 265                 270
```

```
Ala Ala Asp Ala Glu Ala Ile Gly Thr Glu Phe Phe Gly Gln Pro Val
        275                 280                 285

Thr Ala Phe Thr Ser Leu Arg Leu Gly Asp Ser Asp Pro His Ala Gly
290                 295                 300

Ala Arg Thr Val Ala Arg Val Ala Val Val Leu Ala Asp Gly Arg Thr
305                 310                 315                 320

Gly Glu Phe Phe Tyr Lys Pro Arg Ser Val Arg Ser Glu Ala Ala Leu
                325                 330                 335

Gln Asp Val Leu Ala Arg Leu Ala Asp Asp Gly Val Val Asp Phe Ala
        340                 345                 350

Thr Arg Pro Val Leu Pro Arg Asp Gly Tyr Gly Tyr Glu Ala Leu Ile
    355                 360                 365

Pro Ala Gly Arg Asn Arg Val Glu Thr Pro Glu Glu Val Thr Arg Ile
370                 375                 380

Tyr Arg Glu Leu Gly Gly Tyr Leu Ala Leu Phe Tyr Val Leu Gly Gly
385                 390                 395                 400

Ser Asp Leu His Phe Glu Asn Val Ile Val Ala Asp Gly His Ala Phe
                405                 410                 415

Val Cys Asp Ala Glu Thr Val Leu Gly Val His Pro Gln Gly Arg Ala
                420                 425                 430

Gln Ser Glu Gly Thr Leu Leu Asp Ser Val Phe Lys Thr Gly Leu Leu
        435                 440                 445

Glu Trp Pro Arg Ala Ala Ser Pro Gly Glu Glu Ala Ala Ala Glu Met
450                 455                 460

Arg Ile Ser Gly Tyr Ala Gly Gly Glu Gly Tyr Asp Val Pro Val Pro
465                 470                 475                 480

Val Ala Arg Arg Thr Gly Glu Gly Leu Thr Phe Ala Ala Ser Val Val
                485                 490                 495

His Lys Thr Gly Val His Val Glu Thr Ser Ala Ser Asn Arg Val Tyr
            500                 505                 510

Leu Gly Glu Glu Leu Val Arg Pro Glu Asp His Val Glu Ser Ile Met
515                 520                 525

Glu Gly Phe Asn Arg Val Tyr Asp Trp Phe Ala Glu Asp Pro Asp Ala
530                 535                 540

Ser Val Asp Tyr Leu Met Glu Thr Phe Ser Trp Val Thr Ala Arg Phe
545                 550                 555                 560

Ile Asn Trp Gly Thr Gln Ile Tyr Ala Gln Leu Leu Ser Ala Ala Arg
                565                 570                 575

His Pro Arg Cys Leu Thr Glu Pro Leu Glu Val Asp Leu Leu Ala Asn
            580                 585                 590

Thr Val Arg Thr Phe Pro Arg Thr Trp Asp Ala Glu Gly Val Leu Ala
        595                 600                 605

Gly Arg Glu Val Ala Ala Met Trp Gln Met Asp Val Pro Leu Phe Thr
610                 615                 620

Ala Ala Ala His Ala Arg Gln Leu Val His Gly His Gly Asp Pro Leu
625                 630                 635                 640

Ser Ala Arg Leu Asp Ser Ser Pro Ile Asp His Ala Ala Ala Arg Ile
                645                 650                 655

Arg Arg Leu Ser Gln Arg Asn Arg Glu Gln Gln Ser Gln Tyr Ile Ala
            660                 665                 670

Ala Ser Leu Ser Thr Gly Glu Ile Ser Ser Pro Ala Phe Val Ala Thr
        675                 680                 685
```

Ser Leu Asp Tyr Ala Ala Arg Ile Gly Asp Arg Leu Cys Asp Glu Leu
690                 695                 700

Arg Ala Pro Ala Ala Pro Ala Pro Trp Thr Ser Tyr Gln Leu Ser Gly
705                 710                 715                 720

Glu Ser Leu Ala Glu Val Asp Ile Glu Ala Asp Leu Tyr Gln Gly Ser
                725                 730                 735

Ala Gly Val Val Leu Phe Leu Ala Tyr Leu Asp Gln Leu Val Pro Arg
            740                 745                 750

Pro Ala Tyr Arg Lys Ala Ala Arg Gln Ala Leu Asp His Val Leu Val
            755                 760                 765

His Trp Asp Arg Asp Arg Leu Gly Ala Phe Ala Gly Leu Gly Gly Val
770                 775                 780

Val Tyr Leu Leu Thr His Leu His Arg Leu Trp Gly Asp Glu Glu Leu
785                 790                 795                 800

Leu Asp Leu Ala Val Arg Leu Ser Asp Glu Leu Pro Ala Arg Ile Asp
                805                 810                 815

Glu Asp Arg His Phe Asp Ile Leu His Gly Ala Ala Gly Leu Ile Pro
            820                 825                 830

Val Leu Leu Gly Leu Ala Gln Glu Thr Gly Gly His Gly Ile Glu His
            835                 840                 845

Ala His Arg Cys Ala Glu His Leu Leu Arg His Ala Glu Asp Asp Gly
850                 855                 860

Thr Thr Leu Ser Trp Pro Pro Ser Ala Ala Asp Glu Thr Tyr Gly Asn
865                 870                 875                 880

Leu Thr Gly Phe Ser His Gly Ser Gly Gly Ile Gly Trp Ala Leu Ile
                885                 890                 895

Gln Leu Gly Arg His Thr Gly Arg Ser Asp Tyr Ile Glu Ala Gly Arg
            900                 905                 910

Lys Ala Phe Ala Tyr Glu Asp Arg His Val Asp Glu Gln Lys Asp
            915                 920                 925

Trp Tyr Asp Leu Arg Ile Asn Asn Gly Ser Ala Val Lys Gly Ala Arg
930                 935                 940

His Phe Ser Asn Ala Trp Cys Asn Gly Ala Ala Gly Ile Gly Leu Ala
945                 950                 955                 960

Arg Ile Ser Ser Trp Ala Ala Leu Asp Arg Ser Asp Glu Gln Leu Leu
                965                 970                 975

Arg Asp Ala Gln Gln Ala Leu Ser Ala Thr Leu Arg Asn Phe Pro Arg
            980                 985                 990

Leu Lys Asn His Thr Leu Cys His Gly Thr Ser Gly Asn Ala Glu Leu
            995                 1000                1005

Leu Leu Arg Phe Ala Arg Leu Ser Asp Glu Pro Ala Phe Gln Leu Glu
    1010                1015                1020

Ala Asn Val Gln Val Gln Ala Leu Trp Arg Ser Leu Asp Glu Ala Gly
1025                1030                1035                1040

Gly Gly Ala Gly Gly Gly Ser Ala Asp Phe Phe Pro Gly Leu Met Ile
            1045                1050                1055

Gly Ile Ser Gly Phe Gly Met His Phe Leu Arg Leu Ala Ala Pro Asp
            1060                1065                1070

Arg Val Pro Ser Val Leu Leu Leu Asp Pro Pro Ser His His Glu Gln
    1075                1080                1085

<210> SEQ ID NO 12
<211> LENGTH: 325
<212> TYPE: PRT

<213> ORGANISM: Streptomyces cinnamoneus

<400> SEQUENCE: 12

```
Met Ala Leu Lys Thr Cys Glu Glu Phe Leu Arg Asp Ala Leu Asp Pro
  1               5                  10                  15

Ala Arg Phe Gly Arg Glu Met Lys Ala Val Thr Glu Val Pro Glu Ile
             20                  25                  30

Val Glu Leu Gly Arg Arg His Gly Tyr Gly Phe Thr Ala Glu Glu Phe
         35                  40                  45

Leu Thr Lys Ala Met Thr Phe Asp Gly Thr Ala Ala Gly Gly Thr Ala
     50                  55                  60

Ala Gly Gly Pro Glu Ala Gly Gly Gln Gln Ala Pro Arg Gln Thr Pro
 65                  70                  75                  80

Pro Pro Gly Thr Pro Ala Asn Gly Ala Pro Ala Pro Ala Thr Ala Thr
                 85                  90                  95

Ser Phe Ala His Tyr Glu Tyr Arg Leu Asp Asp Leu Pro Glu Phe Ala
            100                 105                 110

Pro Val Val Ala Glu Leu Pro Arg Leu Lys Val Met Pro Pro Ser Ala
        115                 120                 125

Arg Leu Asp Arg Phe Ala Gly His Phe Arg Glu Glu Asp Ala Arg Thr
130                 135                 140

Val Ser Thr Ser Pro Ala Asp Pro Ala Tyr Gln Ala Trp His Arg Asp
145                 150                 155                 160

Leu Ala Ala Arg Gly Trp Gln Asp Glu Gly Ala Ala Pro Gly Ala Pro
                165                 170                 175

Arg Arg Asp Phe His Leu Val Asn Leu Asp Glu His Val Asp Tyr Pro
            180                 185                 190

Gly Tyr Glu Asp Tyr Phe Ala Ala Lys Thr Arg Val Val Ala Ala Leu
        195                 200                 205

Glu Asn Leu Phe Gly Gly Glu Val Arg Ala Ser Gly Ser Met Trp Tyr
    210                 215                 220

Pro Pro Ser Ser Tyr Arg Leu Trp His Thr Asn Ala Asp Gln Pro Gly
225                 230                 235                 240

Trp Arg Met Tyr Leu Val Asp Val Asp Arg Pro Phe Ala Asp Pro Gly
                245                 250                 255

Gln Thr Ser Phe Phe Arg Tyr Leu His Pro Arg Thr Arg Glu Ile Val
            260                 265                 270

Thr Leu Thr Glu Ser Pro Arg Ile Val Arg Phe Phe Lys Val Glu Gln
        275                 280                 285

Asp Pro Glu Lys Leu Phe Trp His Cys Ile Ala Asn Pro Thr Asp Arg
    290                 295                 300

His Arg Trp Ser Phe Gly Tyr Val Val Pro Glu Thr Trp Met Asp Ala
305                 310                 315                 320

Leu Arg His His Gly
                325
```

<210> SEQ ID NO 13
<211> LENGTH: 309
<212> TYPE: PRT
<213> ORGANISM: Streptomyces cinnamoneus

<400> SEQUENCE: 13

```
Met Arg Gly Ile Asp Leu Thr Val Ala Gln Gly Glu Thr Phe Gly Phe
  1               5                  10                  15

Leu Gly Pro Asn Gly Ala Gly Lys Thr Thr Thr Ile Ser Met Leu Thr
```

```
                    20                  25                  30
Thr Leu Ala Thr Pro Thr Thr Gly Arg Ile Glu Ile Ala Gly His Asp
            35                  40                  45
Thr Arg Thr Ala Pro Gln Gln Val Arg Arg Asn Leu Gly Leu Val Phe
        50                  55                  60
Gln Glu Thr Thr Leu Asp Pro Glu Leu Thr Ala Val Glu Asn Leu Arg
65                  70                  75                  80
Phe His Ala Asp Leu Tyr Ala Leu Pro Arg Ala Gly Leu Ala Gly Arg
                85                  90                  95
Ile Ala Glu Met Leu Glu Leu Val Gly Leu Ser Ala Arg Gly Asp Ser
            100                 105                 110
Leu Gly Arg Thr Phe Ser Gly Gly Met Gln Arg Arg Leu Glu Ile Ala
        115                 120                 125
Arg Gly Leu Leu His Arg Pro Arg Leu Leu Phe Leu Asp Glu Pro Thr
130                 135                 140
Ile Gly Leu Asp Pro Gln Thr Arg Ala Gln Val Trp Ala His Leu Ala
145                 150                 155                 160
Glu Val Arg Glu Arg Glu Ala Thr Thr Ile Phe Leu Thr Thr His Tyr
                165                 170                 175
Leu Asp Glu Ala Glu Gln Cys Asp Arg Ile Ala Ile Asp Asp Gly
            180                 185                 190
Arg Ile Val Ala Gln Gly Ser Pro Ala Glu Leu Lys Ser Val Ile Gly
        195                 200                 205
Ala Asp Arg Val Asp Leu Arg Thr Gly Asp Asp Met Ala Ala Ala Ala
210                 215                 220
Leu Leu His Glu Arg Phe Gly Leu Ala Ala Val Arg Gly Pro Asn Gly
225                 230                 235                 240
Leu Ser Val Lys Val Ala Glu Gly Ala Arg Leu Val Pro Ala Leu Cys
                245                 250                 255
Ala Ala Leu Asp Val Ala Val Tyr Glu Val Thr Val Thr Arg Pro Ser
            260                 265                 270
Leu Asp Asp Val Phe Leu His His Thr Gly Arg Gly Ile Arg Asp Asp
        275                 280                 285
Ala Leu Pro Gly Ala Gly Thr Ala Gly Thr Ala Glu Pro Ser Asp
290                 295                 300
Ser Gly Asp Ser Thr
305

<210> SEQ ID NO 14
<211> LENGTH: 290
<212> TYPE: PRT
<213> ORGANISM: Streptomyces cinnamoneus

<400> SEQUENCE: 14

Met Thr His Ala Thr Val Ala Leu Pro Ala Ala Asp Arg His Ala Pro
1               5                   10                  15
Gly Arg Leu Ala Ala Glu Trp Arg Ala Gly Ser Met Val Trp Arg Arg
            20                  25                  30
Glu Met Ile His Phe Leu Arg Ser Arg Ala Gly Ile Ala Val Ser Leu
        35                  40                  45
Leu Gln Pro Leu Leu Phe Leu Tyr Val Leu Gly Ile Gly Leu Ser Arg
    50                  55                  60
Met Phe Ser Gly Ala Gly Ser Ser Asp Asp Tyr Met Ile Phe Leu Phe
65                  70                  75                  80
```

```
Pro Gly Val Leu Val Met Ala Ala Gln Ala Pro Ala Ile Ser Val Gly
                85                  90                  95

Ala Ser Ile Val Trp Asp Arg Gln Ser Gly Phe Leu Arg Glu Met Leu
            100                 105                 110

Val Ala Pro Val Arg Arg Ser Thr Leu Leu Ile Gly Lys Cys Leu Gly
        115                 120                 125

Gly Ala Thr Val Ala Ala Cys Gln Gly Ala Val Val Leu Ala Ser Ala
130                 135                 140

Gly Leu Val Gly Val Pro Tyr Arg Val Asp Leu Phe Ala Ala Leu Leu
145                 150                 155                 160

Ala Glu Leu Leu Leu Ala Ser Leu Ala Met Thr Val Leu Gly Ala Val
                165                 170                 175

Ile Ala Val Arg Ile Gln Arg Ile Gln Thr Phe His Thr Ala Leu Thr
            180                 185                 190

Val Leu Thr Ala Pro Met Val Phe Leu Ser Gly Leu Met Phe Pro Val
        195                 200                 205

Ser Ala Met Pro Ala Trp Met Ala Ala Leu Thr Leu Val Asn Pro Leu
210                 215                 220

Thr Tyr Ala Val Asp Ala Met Arg Gln Thr Ile Thr Ala Phe His Pro
225                 230                 235                 240

Ala Pro Ala Ala Gly Ala Ser Gly Ala Pro Ile Phe Asp Pro Val Ser
                245                 250                 255

Trp Gly Gly Trp Asp Val Pro Pro Gly Leu Ser Val Val Leu Val Ala
            260                 265                 270

Val Phe Ser Ala Leu Ala Leu Ala Ala Ser Arg Arg Phe Ser Arg
        275                 280                 285

Thr Asp
    290

<210> SEQ ID NO 15
<211> LENGTH: 340
<212> TYPE: PRT
<213> ORGANISM: Streptomyces cinnamoneus

<400> SEQUENCE: 15

Met Arg Ser Thr Arg Arg Leu Ser Leu Arg Arg Ser Ala Leu Leu
1               5                   10                  15

Met Gly Ala Ala Ser Leu Ala Ala Pro Ala Leu Leu Thr Val Gln Ala
            20                  25                  30

Gly Glu Ala Gln Ala Phe Gly Thr Ile Asn Ser Leu Gly Gln Arg Ala
        35                  40                  45

Glu His Glu Arg Ile Thr Arg Ala Ala Leu Ala Cys Ala Ala Gly Thr
    50                  55                  60

Ser Ser Asp Gly Ser Cys Phe Glu Ala Arg Ser Ile Asp Gln Val Ala
65                  70                  75                  80

Gly His Thr Gly Thr Phe Gly Ala Val Gly Ser Pro Asp Ser Asp Glu
                85                  90                  95

Ile Phe Thr Pro Glu Ala His Cys Asp Asp Ala Asp Tyr Leu Thr Ala
            100                 105                 110

Ser Gly Tyr Pro Arg Thr Arg Gln Gln Ala Ser Asp Gln Leu Val Ala
        115                 120                 125

Cys Ile Ser Lys Leu Gln Gly Arg Phe Ser Gln Gly Val Ala Ala Gly
130                 135                 140

Ser Gly Thr Leu Asn Gly Asp Gly Thr Val Ser Pro Gly Asn Ser Asp
145                 150                 155                 160
```

-continued

```
Leu Ser Gln Asp Cys Thr Phe Thr Gly Gly Val Pro Gly Arg Gly Lys
                165                 170                 175

Cys Asn Ala Ile Glu Gly Phe Gly Arg Ala Leu His Gly Val Gln Asp
            180                 185                 190

Phe Tyr Ser His Ser Asn Trp Ala Asp Lys Ala Asp Pro Asn Gln Ala
        195                 200                 205

Val Gly Val Asn Asn Pro Pro Gly Leu Asn Met Ser Gly Pro Ala Pro
    210                 215                 220

Leu Leu Ser Leu Lys Ser Gly Arg Pro Pro Ala Ala Ser Ser Val Pro
225                 230                 235                 240

Ala Gln Leu Ser Thr Gly Cys Phe Ser Leu Asn Pro Trp Gly Cys Ser
                245                 250                 255

Gly Arg Val Thr His Ser Thr Leu Asn Lys Asp Thr Gly Leu Ile Asp
            260                 265                 270

Pro Ala Ser Gly Ala Thr Ser Asp Pro Thr Thr Asn Arg Gly Arg Ile
        275                 280                 285

Thr Gly Asn Phe Asp Arg Ala Val Lys Gly Ala Ile Ala Asp Thr Arg
    290                 295                 300

Arg Gln Trp Ala Asp Phe Arg Thr Ala Leu Thr Glu Arg Tyr Gly Gln
305                 310                 315                 320

Glu Arg Gly Gln Arg Ile Ala Cys Val Leu Thr His Asp Asn Pro Val
                325                 330                 335

Arg Asp Cys Arg
            340

<210> SEQ ID NO 16
<211> LENGTH: 208
<212> TYPE: PRT
<213> ORGANISM: Streptomyces cinnamoneus

<400> SEQUENCE: 16

Met Gln Asp Glu Tyr Arg Thr Val Ala Leu Glu Gly Val His Glu Ile
1               5                   10                  15

Glu Ile Ser Arg Ser Arg Phe Ile Cys Ala Leu Ala Pro Ala Ala Thr
            20                  25                  30

Glu Glu Glu Ala Gln Ala Phe Leu Ala Arg Ile Arg Lys Glu His Pro
        35                  40                  45

Thr Ala Arg His His Cys Trp Ala Tyr Val Leu Gly Ala Asp Gly Ser
    50                  55                  60

Val Gln Lys Ala Ser Asp Asp Gly Glu Pro Gly Gly Thr Ala Gly Val
65                  70                  75                  80

Pro Met Leu Gln Met Leu Leu Arg Arg Asp Met Arg Tyr Val Val Ala
                85                  90                  95

Val Val Thr Arg Tyr Phe Gly Gly Val Lys Leu Gly Ala Gly Gly Leu
            100                 105                 110

Ile Arg Ala Tyr Gly Gly Val Val Gly Glu Ala Leu Asp Glu Leu Gly
        115                 120                 125

Thr Val Thr His Lys Arg Phe Arg Leu Ala Thr Val Thr Val Asp His
    130                 135                 140

Gln Arg Ala Gly Lys Leu Gln Asn Asp Leu Arg Ala Thr Gly Arg Glu
145                 150                 155                 160

Val Arg Glu Val Ala Tyr Gly Glu Gly Val Arg Ile Gly Ile Gly Leu
                165                 170                 175

Pro Glu Ala Asp Val Glu Gly Phe Arg Ala Trp Leu Ala Asp Thr Thr
```

```
                    180                 185                 190
Ala Gly Thr Ala Val Leu Glu Leu Gly Gly Glu Ala Tyr Gly Asp Ala
        195                 200                 205
```

<210> SEQ ID NO 17
<211> LENGTH: 139
<212> TYPE: PRT
<213> ORGANISM: Streptomyces cinnamoneus

<400> SEQUENCE: 17

```
Met Phe Ala Glu Pro Gly Ile Ile Gln Lys Ile Ile Glu Gly Thr Gly
  1               5                  10                  15

Asp Thr Trp Ala Leu Val Gly Leu Ser Ala Asn Glu Gln Arg Ala Ala
             20                  25                  30

Tyr Gly Val Ala Glu Val Leu Gln Arg His Gly Lys Arg Ile Val Pro
         35                  40                  45

Val His Pro Lys Ala Glu Thr Val His Gly Glu Leu Gly Tyr Ala Ser
     50                  55                  60

Leu Ala Asp Ile Pro Phe Asp Val Asp Val Val Asp Val Phe Val Arg
 65                  70                  75                  80

Ser Glu Leu Ala Gly Ala Val Ala Asp Glu Ala Val Glu Ile Gly Ala
                 85                  90                  95

Lys Ala Val Trp Phe Gln Leu Gly Val Ile Asp Glu Glu Ala Tyr Asp
            100                 105                 110

Arg Thr Arg Gly Ala Gly Leu Leu Met Val Met Asp Arg Cys Pro Ala
        115                 120                 125

Ile Glu Leu Gly Arg Pro Arg Gly Arg Ala Val
    130                 135
```

<210> SEQ ID NO 18
<211> LENGTH: 106
<212> TYPE: PRT
<213> ORGANISM: Streptomyces cinnamoneus

<400> SEQUENCE: 18

```
Met Arg Lys Ser Leu Ala Val Ala Ala Ala Ser Ala Val Ala Gly Leu
  1               5                  10                  15

Thr Leu Met Ala Gly Thr Pro Ala Asn Ala Ala Pro Ala Ala Ala Thr
             20                  25                  30

Thr Val Pro Ser Cys Val Thr Ser Thr Phe Ser Thr Pro Phe Phe Ala
         35                  40                  45

Met Val Arg Val Asp Met Glu Asn Lys Cys Thr Thr Glu Gln Arg Val
     50                  55                  60

Lys Pro Ser Phe Asn Tyr Glu Leu Lys Asp Val Pro Cys Tyr Ala Leu
 65                  70                  75                  80

Gln Pro Gly Gln Lys Ala Val Phe Ser Arg Asp Val Ile Phe Ala Ser
                 85                  90                  95

Gly Tyr Thr Phe Ala Gly Leu Val Ser Cys
            100                 105
```

<210> SEQ ID NO 19
<211> LENGTH: 216
<212> TYPE: PRT
<213> ORGANISM: Streptomyces cinnamoneus

<400> SEQUENCE: 19

```
Met Ile Arg Thr Leu Ile Val Asp Asp Ser Leu Val Arg Leu Ala
  1               5                  10                  15
```

-continued

Leu Ala Asp Ile Leu Asp Asp Val Pro Gly Ile Glu Val Ala Gln
             20                  25                  30

Ala Gly Asp Gly Leu Glu Ala Val Gln Arg Ala Gly Ala Leu Arg Val
     35                  40                  45

Asp Val Ala Leu Met Asp Val Arg Met Pro Arg Met Asp Gly Ile Ala
 50                  55                  60

Ala Thr Glu Arg Leu Arg Ala Leu Pro Ser Pro Glu Val Val Met
 65                  70                  75                  80

Leu Thr Thr Phe Asp Leu Asp Gln Tyr Val Tyr Asp Ala Leu Ala Ala
                 85                  90                  95

Gly Ala Ser Gly Phe Leu Leu Lys Asp Thr Asp Pro Ala Glu Ile Ile
             100                 105                 110

Arg Ala Ile Gln Val Val Ala Gly Gln Ala Met Leu His Pro Ala
         115                 120                 125

Ala Ala Arg Arg Leu Val Asp Arg Tyr His Arg Thr Ala Ser Arg Asp
 130                 135                 140

Val Gln Ala Ala Gln Gln Arg Leu Ala Arg Leu Thr Pro Arg Glu Ser
145                 150                 155                 160

Asp Val Leu Gly Leu Leu Ala Ala Gly Ala Ser Asn Ala Glu Ile Ala
                 165                 170                 175

Asp Gly Leu Gly Met Arg Glu Ser Thr Val Lys Ala His Val Ser Arg
             180                 185                 190

Ile Leu Ala Ala Leu Glu Val Gly Asn Arg Val Gln Ala Ala Leu Cys
         195                 200                 205

Ala Arg Asp Ala Gly Leu Thr Val
 210                 215

<210> SEQ ID NO 20
<211> LENGTH: 354
<212> TYPE: PRT
<213> ORGANISM: Streptomyces cinnamoneus

<400> SEQUENCE: 20

Met Gly Ala Gly Ala Thr Leu Trp Gly Pro Asp Thr Ala Val Ala Ala
 1               5                  10                  15

Val Gly Ser Leu Ser Leu Ala Val Arg Tyr Arg Val Pro Leu Val Thr
             20                  25                  30

Val Val Thr Val Cys Ala Ala Val Val Gly Ala Leu Leu Pro
         35                  40                  45

Leu Leu Val Met Leu Phe Tyr Leu Ala Ser Arg Gly Trp Arg Ala Leu
 50                  55                  60

Gly Cys Ala Cys Ala Ala Val Ala Leu Ala Gly Asn Trp Phe Ala Gln
 65                  70                  75                  80

Pro Glu Gln Leu Leu Trp Ser Thr Arg Ala Tyr Gly Pro Val Leu Pro
                 85                  90                  95

Phe Ala Leu Val Met Val Leu Gly Leu Trp Ala Asp Ser Arg Arg Arg
             100                 105                 110

Leu Glu Ala Ser Leu Thr Ala Gln Val Glu His Leu Arg Val Glu Arg
         115                 120                 125

Glu Leu Arg Ala Lys Gln Ala Arg Leu Ser Glu Arg Ala Arg Ile Ala
 130                 135                 140

Ala Glu Met His Asp Val Leu Ala His Arg Leu Ser Leu Leu Ala Leu
145                 150                 155                 160

His Ala Gly Ala Leu Gln Arg Arg Ala Ala Thr Leu Pro Glu Pro Val

-continued

```
                165                 170                 175
Ala Asp Arg Leu Ala Leu Leu Arg Thr Thr Ser Thr Glu Ala Leu Gly
            180                 185                 190

Asp Leu Arg Asp Val Leu Gly Val Leu Arg Asp Pro Asp His Pro Glu
        195                 200                 205

Leu Gln Gly Gln Arg Val Pro Gly Leu Arg Glu Leu Pro Ala Leu Phe
    210                 215                 220

Asp Glu Ala Arg Ala Ala Gly Gln Glu Ile Asp Ala Val Val Glu Gly
225                 230                 235                 240

Ala Ala Gly Pro Leu Pro Ala Ser His Arg Leu Ala Val His Arg Leu
                245                 250                 255

Val Gln Glu Ala Leu Thr Asn Ala Arg Lys His Ala Pro Gly Ala Pro
            260                 265                 270

Val Arg Val Val Arg Tyr Gly Pro Pro Ala Ser Ser Val Glu Val
        275                 280                 285

His Asn Arg Ala Gly Asp Pro Ala Ser Ala Ala Gly Glu Pro Pro Val
    290                 295                 300

Ser Ser Gly Tyr Gly Leu Val Gly Leu Ala Glu Arg Val Thr Ala Leu
305                 310                 315                 320

Gly Gly Arg Leu Asp Tyr Gly Pro Ser Gly Gly Gly Trp Asn Ile
                325                 330                 335

Ala Ala Asp Ile Pro Val Ser Thr Val Glu Glu His Leu Ala Pro Gly
            340                 345                 350

Ala Ala
```

<210> SEQ ID NO 21
<211> LENGTH: 165
<212> TYPE: PRT
<213> ORGANISM: Streptomyces cinnamoneus

<400> SEQUENCE: 21

```
Met Thr Arg Val Leu Ala Gly Ala Val Gly Pro Ala Asp Arg Leu Asp
  1               5                  10                  15

Val Val Glu Ile Asn Pro Arg Phe Val Glu Ile Leu Asn Gly Ala Leu
            20                  25                  30

Arg Thr Asp Pro Ala Met Ser Ala Ser Asp Arg Ile Arg Ile Ile
        35                  40                  45

Pro Glu Ser Ile Thr Glu Met Pro Ile Asp His Ser Tyr Asp Val Val
    50                  55                  60

Val Ser Cys Leu Pro Phe Thr Asn Phe Ala Pro Glu Thr Val Arg Ser
 65                  70                  75                  80

Ile Leu Asp Arg Tyr Leu Ser Val Leu Pro Gly Gly His Leu Thr
                85                  90                  95

Phe Phe Gly Tyr Leu Gly Thr His Ala Thr Arg Ser Leu Leu Ser Ser
                100                 105                 110

Arg Lys Glu Ala Ala Arg His Arg Glu Val Thr Asp Leu Leu His Asp
            115                 120                 125

Phe Thr Arg Arg Tyr Ala Ser Arg Gln Ser Val Val Trp Arg Asn Ile
        130                 135                 140

Pro Pro Ala Arg Val Trp His Val Arg Ala Pro Glu His Ala Thr Arg
145                 150                 155                 160

Ala Ala Asp Ala Ala
                165
```

<210> SEQ ID NO 22
<211> LENGTH: 396
<212> TYPE: PRT
<213> ORGANISM: Streptomyces cinnamoneus

<400> SEQUENCE: 22

```
Met Pro Thr Ala Asp Glu Leu Leu His Gly Val Pro Ala Ala Ala
 1               5                  10                  15

Tyr Gly Leu Val Leu Gly Leu Val Leu Glu Ser Val Leu Leu Leu
                20                  25                  30

Gly Ser Phe Val Pro Thr Leu Ser Leu Met Leu Cys Ala Gly Val Leu
            35                  40                  45

Ala Gln Glu Gly Thr Leu Arg Leu Pro Leu Val Val Leu Cys Ala Thr
        50                  55                  60

Thr Gly Val Val Ala Gly Asp Leu Leu Ala Gln Arg Thr Gly Arg Arg
 65                  70                  75                  80

Leu Gly Pro Gly Leu Arg Arg Ser Arg Leu Gly Arg Arg Leu Pro Glu
                85                  90                  95

Ala Ala Trp Glu Arg Ala Trp Ser Val Leu Gln Arg Arg Gly Gly Pro
            100                 105                 110

Ala Leu Leu Val Cys Arg Phe Val Pro Val Val Arg Thr Phe Ala Pro
        115                 120                 125

His Leu Ala Gly Ala Ala Gly Met Pro Tyr Arg Arg Leu Ala Pro Tyr
    130                 135                 140

Ser Leu Val Ala Gly Leu Val Trp Ala Gly Gly Glu Ala Gly Ala Gly
145                 150                 155                 160

Tyr Val Leu Gly Ala Ser Tyr Asp Arg Leu Thr Ala Pro Gly Gly Gly
                165                 170                 175

Leu Pro Thr Val Cys Ala Ala Ala Gly Val Leu Leu Ala Ala Ala Ala
            180                 185                 190

Gly Leu Leu Val His Arg Arg Ala Arg Arg Ala Val Gly Gly Ser
        195                 200                 205

Gly Arg Ala Gly Gln Arg Gln Ala Asp Val Gly Ala Gln Asp Arg Asp
    210                 215                 220

Val Gln Met Thr Gln Leu Ala Pro Gly Val His Pro Glu Leu Val Ala
225                 230                 235                 240

Glu Asp Ala Ala Asp Leu Arg Val Arg Gly Gln Gly Leu Ala Pro Ala
                245                 250                 255

Ala Ala Ala Val Glu Gly Glu His Gln Pro Leu Pro Gln Ala Leu Ala
            260                 265                 270

Gln Arg Val Leu Arg Gly Gln Arg Pro Gln Val Ala Asp Asp Leu Val
        275                 280                 285

Val Ala Ala Glu Gly Glu Ala Gly Val Val Ala Leu Asp Gly Pro
    290                 295                 300

Asp Pro Leu Leu His Gln Pro Arg His Val Pro Val Glu Arg Val
305                 310                 315                 320

Arg Ala His Ala Ala Glu Arg Leu Ala Val Pro Glu Gly Gln Cys Leu
                325                 330                 335

Gly Glu Gly Gly Val Leu Gln Cys Ala Val Ala Glu Leu Gly Gly Glu
            340                 345                 350

Pro Gly Ala Gly Gly Phe Thr Glu Lys Ser Glu Ile Gln Thr Ala
        355                 360                 365

Gly Gly Asp Leu Asp Gln Val Thr Ala Gly Arg Gly Val Gln Gln Ser
    370                 375                 380
```

```
Gly Glu Pro Arg Ala Gly Cys Val Gln Ala Leu Ser
385                 390                 395

<210> SEQ ID NO 23
<211> LENGTH: 261
<212> TYPE: PRT
<213> ORGANISM: Streptomyces cinnamoneus

<400> SEQUENCE: 23

Met Asn Arg Ala Ile Ser Phe Arg Val Leu Gly Pro Leu Ser Val Thr
  1               5                  10                  15

Val Gly Arg Lys Asn Val Ser Leu Pro Ser Gly Arg Gln Arg Ser Leu
             20                  25                  30

Leu Ala Ala Leu Leu Val His Pro Gly Glu Ile Val Pro Val Glu Lys
         35                  40                  45

Leu Val Asp Leu Val Trp Gly Asp Glu Leu Pro His Ser Pro Arg Pro
     50                  55                  60

Ala Leu His Thr Leu Leu Thr Arg Leu Arg Gln Ser Leu Asp Ala Ala
 65                  70                  75                  80

Gly Ala Gly Leu Ser Gly Leu Leu His Thr Ser Pro Ser Gly Tyr Leu
                 85                  90                  95

Ile Glu Val Pro Thr Gly Cys Leu Asp Leu Thr Leu Phe Arg Glu Ser
            100                 105                 110

Ala Ala Arg Ala Arg Leu Ala Ala Glu Leu Gly Asp Arg Ala Leu Glu
        115                 120                 125

His Ser Ala Leu Thr Glu Ala Leu Ala Leu Trp His Gly Gln Pro Leu
    130                 135                 140

Gly Gly Val Arg Ser Asp Ala Leu His Arg Asp Val Val Pro Gly Leu
145                 150                 155                 160

Met Glu Glu Trp Ile Arg Ala Ile Glu Arg Tyr His Asp Ala Cys Leu
                165                 170                 175

Ala Leu Gly Arg His Asp Glu Ile Val Gly Asp Leu Arg Thr Leu Thr
            180                 185                 190

Ala Lys Tyr Pro Leu Arg Glu Ser Leu Trp Gln Arg Leu Met Leu Ala
        195                 200                 205

Leu Tyr Arg Cys Gly Arg Arg Gly Glu Ala Leu Ala Ala Tyr Ala Glu
    210                 215                 220

Val Ser Gly Val Phe Arg Asp Glu Leu Gly Val Asp Pro Gly Arg Glu
225                 230                 235                 240

Leu Arg His Leu His Val Ala Ile Leu Arg Thr Asp Val Ser Leu Ser
                245                 250                 255

Leu Ala Arg Ser Ala
            260

<210> SEQ ID NO 24
<211> LENGTH: 163
<212> TYPE: PRT
<213> ORGANISM: Streptomyces cinnamoneus

<400> SEQUENCE: 24

Met Ser Asp Ser Arg Pro Ala Pro Asp Arg Asn Asp Arg Pro Leu Leu
  1               5                  10                  15

Arg Gln Phe Asp Gln Arg Leu Ser Glu Leu Ile Ala Thr Thr Ala Gly
             20                  25                  30

Ala Glu Gly Asn Lys Arg Pro Gly Tyr Ala Arg Leu Ala Lys Glu Ile
         35                  40                  45
```

-continued

```
Arg Asp Thr Thr Gly Arg Thr Ile Ser Gly Thr Tyr Leu Trp Glu Leu
 50                  55                  60

Ala Thr Gly Lys Lys Arg Asn Val Thr Leu Glu Gln Leu Asp Val Leu
 65                  70                  75                  80

Ala Glu Phe Phe Gly Val Pro Pro Glu Tyr Phe Leu Asp Asp Glu Thr
                 85                  90                  95

Gly Arg Arg Ile Asp Asp Arg Arg Leu Ala Ile Ala Leu Arg Asp
                100                 105                 110

Ala Lys Val Arg Asn Leu Ala Leu Arg Ala Asp Gly Leu Ser Pro Asp
                115                 120                 125

Cys Leu Asp Ala Leu Ile Ala Met Val Asn Glu Ala Arg Lys Thr Gln
    130                 135                 140

Asn Leu Ser Ser Ile Asp Asp Asp Asp Thr Ala Thr Thr Leu Thr
145                 150                 155                 160

Ser Ser Gly
```

<210> SEQ ID NO 25
<211> LENGTH: 194
<212> TYPE: PRT
<213> ORGANISM: Streptomyces cinnamoneus

<400> SEQUENCE: 25

```
Met Pro Arg Arg Thr Tyr Val Ala Tyr Arg Arg Cys Leu Arg Lys Gly
  1               5                  10                  15

Gln Arg Glu Pro Glu Met Pro Tyr Thr Ser Asp Ala Ala Leu Arg Arg
                 20                  25                  30

Arg Cys Arg Ala Leu Leu Ala Arg Val Ser Leu Pro Glu Pro Phe Ser
             35                  40                  45

Val Glu Val Leu Cys Arg His Leu Gly Glu Gln Arg Gly Arg Pro Ile
 50                  55                  60

His Leu His Pro Leu Pro Glu Gln Ala Ala Leu Ala Gly Ala Cys Gly
 65                  70                  75                  80

Leu Trp Leu Ala Thr Ala Thr Asp Asp His Ile Phe His Glu Arg His
                 85                  90                  95

Thr Val Arg Pro His Gln Glu His Ile Val Leu His Glu Ile Gly His
                100                 105                 110

Met Leu Phe Asp His His Ser Leu Ala Pro Ala Gly Gly Pro Ala Gly
            115                 120                 125

Ala Leu Leu Ala Asp Leu Asp Pro Arg Leu Ile Arg Arg Leu Leu Ala
    130                 135                 140

Arg Thr Asn Tyr Ser Thr Arg Gln Glu Arg Glu Ala Glu Met Leu Ala
145                 150                 155                 160

Ser Leu Ile Arg Thr Ser Val Arg Ala Gly Thr Gly Glu Arg Pro Pro
                165                 170                 175

Gly Ala Leu Gly Arg Leu Gln Ala Ala Leu Gly Val Val Gly Ser His
                180                 185                 190

Gly Arg
```

<210> SEQ ID NO 26
<211> LENGTH: 177
<212> TYPE: PRT
<213> ORGANISM: Streptomyces cinnamoneus

<400> SEQUENCE: 26

```
Met Val Leu Arg Cys Pro Tyr Ala Val Arg His Pro Ala Gln Arg Gly
  1               5                  10                  15
```

-continued

```
Leu Trp Leu Ala Val Ala Thr Ala Ala Leu Ala Met Thr Leu Thr Thr
         20                  25                  30

Ser Ile Gly Ser Val Val Pro Glu Ala Ala Leu Gly Leu Ala Gly Asn
         35                  40                  45

Leu Thr Gly Met Val Ser Ala Gly Ala Val Leu Gly Phe Val Ile Thr
     50                  55                  60

Ile Met Gly Gly Arg Arg Leu His Thr Trp Ala Cys Gly Thr Val Ala
 65                  70                  75                  80

Ala Thr Ala Leu Ala Leu Thr Val Leu Gly Val Thr Ser Arg Ala His
                 85                  90                  95

Leu Ser Tyr Gly Thr Ile Ala Glu Ile Pro Pro Thr Ala Thr Ala Tyr
             100                 105                 110

Arg Leu Leu Leu Ile Gly Thr His Leu Ala Val Asn Ala Ala Cys Ile
         115                 120                 125

Ala Val Cys Trp Arg Tyr Gly Arg Gly Pro Ser Arg Ser Pro Leu Ala
     130                 135                 140

Leu Gly Leu Arg Leu Phe Gly Ile Gly Thr Val Leu Ala Glu Leu Tyr
145                 150                 155                 160

Trp Leu Arg Leu Phe Ala Gly Leu Phe Thr Thr Ser Asp Ala Leu Leu
                165                 170                 175

Arg
```

<210> SEQ ID NO 27
<211> LENGTH: 4975
<212> TYPE: DNA
<213> ORGANISM: Artificial Sequence
<220> FEATURE:
<223> OTHER INFORMATION: Description of Artificial Sequence: pCK51
<220> FEATURE:
<221> NAME/KEY: misc_feature
<222> LOCATION: (1) .. (4975)
<223> OTHER INFORMATION: n may represent a, c, g or t

<400> SEQUENCE: 27

```
cccgggccgt tcgcccacca cgagcccac gcccagcggc accgccacgc ccccgagggc    60
acccagcggc nagacgacgc ccatggggcc cagggccagg gccttgtaga aggcgagcat   120
cgccgcgggg cccacgacgc cngcggccac cgcgtaccag agcccgggc cggcctcgga    180
ccagccgccg gtgccgatca cgatcgtgcc canggcgagg acggccagca gctgggacac   240
caggaccacg gtcagggcgg gcatgcgccg ggtgagcagc ccgncgccga agtcggccag   300
ccccccacatg aggctggtgg ccagggcgaa gaccggtgtc atggggagga cctcncagta   360
cagtgtgatg aacggtggcg tccacgacac cgtagtacat gatgctcgac ttgcaagaat   420
aatatnttgg acgggacgga tcggaccgac gtgacggacc tcgaccagct cacgcaatcg   480
ctcgcccgca acctcangcg ctggcgcggt gagcgccact tcaccctcga cgccctcgcg   540
gcccgctccg gcgtcagccg cggcatgntc atccagatcg agcaggcccg gacgaacccc   600
agcgtcggca ccacggtgaa gctcgccgac gccctcggng tcagcatcac caccctgctc   660
gactacgagc agggcgcccg cgtgcggctc gtacccgagg agcaggtggn ccgcatgtgg   720
tccaccgagg cgggcagcca cacctcgctg ctcgtcggcg ccgatgtccg cggcccgctg   780
naactgtggg actggcgcct cgtgcccggc gacagcagcg tctcggaccc ccacccgccc   840
ggcaccgtcg anatgctgac cgtacggtcg ggccgcctca cgctcgtcgt cgacggcgag   900
gagtacgagg tcgccgccgg canctcggcc accttcgagg ccgacgccgc acacacctac   960
```

-continued

```
cgcaacgacg gcaccgagcc cgtcgagatg acgntggtgg tggccgtccc gcccgcgggc     1020
tgacagccgc cggcccctga acgcaccggg cccgccggga cacgncgagc gacgctctcc     1080
cggcgggcct ccgtgcgtgg ttgccccgtg cgccggtgaa gacggtgctt ccgaanccgg     1140
gcttcccaag tcggtgctcc tgaaagcgga gtgaaaccgt agtgaaagcg gacgctccta     1200
atgtctntct caccgggaac cgactggatg gggaaacggg ccatgaaaag tgccaaggaa     1260
ccgacgatct accaggangt ggagatcatc cgccgcatcc aggagctcat ggttctctgc     1320
tccttgctgc cgcccgacgg caagctgcnt gaagcgctgg agttcgctct ctcgctccac     1380
gaggagccgg tactggcccg gatcactccc ctcaccaatn tccatccctt cgcgacgaaa     1440
gcctggctgg agtccctgtg gctcggcgaa ggcgtttcca gcgaggagaa ngagctggtc     1500
gcctggcaga caacagcga caacatggga ccggccattc gtgaactcaa gaatgccgaa     1560
cngcagtccg gcatcaggct ggtcgctcag ctgacgtcct gacaccgcc tgggtgccgg      1620
gattcacctc aanatcggag gtaagccatg accgcttcca ttcttcagca gtccgtcgtg     1680
gacgccgact tccgcgcggc gctncttgag aaccccgccg ccttcggcgc ttccgccgcg     1740
gccctgccca cgcccgtcga ggcccaggac caggngtccc ttgacttctg gaccaaggac     1800
atcgccgcca cggaagcctt cgcctgccgc cagagctgca gcttcngccc gttcaccttc     1860
gtgtgcgacg caacaccaa gtaagtggct gctgcctcta ggcggtaatg ctcgccnggt      1920
gcgatgacgc ggtgggccgg tgacctgccg gcccaccgcg ttgcgccgcg cggcggcgcc     1980
cctgccanga gggtcacgag gctccttcga cttcgaccgc aggagaaatt cgcatatggg     2040
tatgggtaat gcgtatccnc tggacatcgc agcacgggcg gccaatctga ccgaacggtt     2100
acgggtcgtg gccgccgcgg gcggcgaggn ggccgtgcgg gacaccacgg tcgaactcga     2160
cgccttcgac cgctggaaga ccgacacgct ggccggaaaa ntggccgaca aattccacca     2220
ggaatcgctg caccgcggcc ggccgcccca gcacaccaag gacgaactcg cnggcgtgct     2280
ctccgcctac cgccgtctgg aactcgccct ggacaccgcg gacgacgacg tccgggcact     2340
tcncggcgag ctgcagagcg cctggctgcc cacctaccgc gcggccctcg acgcccacga     2400
cgccgcccgc gacngcgaac gcaccgacgc gcaggcgggc gaggagcccg gctggcgcgc     2460
gttcgacgtg tactacggcc ggctngccaa ggcgtgcgag ccgttcctgc gcgaactggg     2520
ccgcggcctg gaggccgcac gcggcgccgc acaggncgag aacaccgcgc tctccccgca     2580
actggccgag gacatccagc gccacctgct cgaccgcttc gagctgngcg tggcctgggc     2640
cgtggaggcc gacgccaacg tgcactgcac ccaggccggg atcgacaagg ccgaggcnac     2700
gcgcgaggac tacctcgcct acctcgacac cacgttctcc gacagcgccg cctaccaccg     2760
cttctaccng aagttcccgg tgctcggccg ctggctcgcc cacaccaccg ccctgctcac     2820
cgcgttcggc cgcgacctcn tcgacagcct ggccgccgac gcgcaggcca tcggcaccga     2880
gttcttcggg cagccgatca ccgcgttcac ntccctgcgg ctgggcgact ccgacccccca    2940
cgcgggcgcg cgcaccgtcg cccgcgtctc cgtcgtgctc gncgacgggc gcaccggcga     3000
gttcttctac aagccgcgca gcgtccggtc cgaggcggcg ctccaggacg tcntcgccag     3060
gctggcggac gacggggtcg tcgacttcgc gacccggccc gtcctgcccc gggacggcta     3120
cggntacgag gcgctgatcc ccgccggacg caaccgcgtc gagaccccgg aggaggtcac     3180
ccggatctac cgcgnactgg gcggctacct ggcgctgttc tacgtcctgg gcggcagcga     3240
cctccacttc gagaacgtca tcgtcnccga cggacacgcc ttcgtctgcg acgccgagac     3300
cgtcctcggc gtccaccccc agggacgggc acagtcngag ggcaccctcc tcgactccgt     3360
```

-continued

```
cttcaagacc ggactcctcg aatggccgcg cgccgcgagc ccgggcgngg aggccgccgc    3420
cgagatgcgc atcagcggct acgcgggcgg cgagggatac gacgtccccg tcccggagnc    3480
ccgccgcacn ggcgaggggn tcagcttcgc ggcctccgtc gtgcacaaga ccggcgtcca    3540
cgtcgagacn agcgcctcca accgcgtcta cctcggcgag gagctcgtgc gtcccgagga    3600
ccacgtcgag tcgatcatgg ngggcttcaa ccgcgtctac gactggttcg ccgaggaccc    3660
cgacgcgtcc gtcgactacc tgatggagac gntcagctgg gtcaccgccc gcttcatcaa    3720
ctggggcacc cagatctacg cccagctgct gagcgccgcc cgncacccgc gctgcctcac    3780
cgaacccctc gaagtggacc tgctcgccaa caccgtccgc accttccccc gcanctggga    3840
cgccgaaggc gtcctggccg gacgggaagt ggccgccatg tggcagatgg acgtgccgct    3900
gttcnccgcg gccgcccacg cccggcagct cgtccacggg cacagcgacc cgctgcccgc    3960
ccggctggac agctcnccga tcgaccacgc ggccgcacgc atccggcggc tgtcggagcg    4020
caaccgcgaa cagcagagcc agtacancgc cgccagcctc tcgaccggcg agatcagcag    4080
ccccgccttc gtcgccacct ccctggacta cgcggccngg atcggcaacc gtctgtgcga    4140
cgagctgcgg gcccccgccg cctccgcccc ctggacctcc taccagctnt ccggcgaatc    4200
cctcgccgag gtggacatcg aggccgacct ctaccagggc tccgccggcg tcgtcctctn    4260
cctcgcctac ctcgaccagc tcgtgccccg ccccgagtac cgcaagaccg cccggcaggc    4320
cctcgaccat ntcctcgtgc actgggaccg cgaccggctc ggcgccttcg ccggactcgg    4380
cggcgtcgtc tacctcctca cncacctgca ccgcctctgg ggcgacgagg agctcctcga    4440
cctggcggtg cggctcagcg acgagctgcc cgnacgcatc gacgaggacc ggcacttcga    4500
catcctgcac ggcgcggccg gcctcatccc cgtcctcctc ggcntcgccc gggagaccgg    4560
cggccacggc atcgagcacg cccaccgctg cgccgaacac ctgctgcgcc acgcngagga    4620
cgacggcacc accctcagct ggcccccctc cgcggccgac gagacgtacg gcaacctcac    4680
cggctnctcg cacggctccg gcggcatcgg ctgggcgctc atccagctcg gccggcacac    4740
cggcaggacg gactacntcg aggccgggcg caaggcgttc gcctacgagg accggcacgt    4800
cgacgagcag gagaaggact ggtacganct gcggatcaac aacggatcct ctagagtcga    4860
cctgcaggca tgcaagcttg gcgtaatcat ggtcatagnt gtttcctgtg tgaaattgtt    4920
atccgctcac aattccacac aacatacgag ccggaagcat aaagtgtnan gcctg         4975
```

<210> SEQ ID NO 28
<211> LENGTH: 1337
<212> TYPE: DNA
<213> ORGANISM: Artificial Sequence
<220> FEATURE:
<223> OTHER INFORMATION: Description of Artificial Sequence:
      Tetracycline resistance cassette of pDWFT33

<400> SEQUENCE: 28

```
aggcctcgcc ggcttccatt caggtcgagg tggcccggct ccatgcaccg cgacgcaacg      60
cggggaggca gacaaggtat agggcggcgc ctacaatcca tgccaacccg ttccatgtgc     120
tcgccgaggc ggcataaatc gccgtgacga tcagcggtcc agtgatcgaa gttaggctgg     180
taagagccgc gagcgatcct tgaagctgtc cctgatggtc gtcatctacc tgcctggaca     240
gcatggcctg caacgcgggc atcccgatgc cgccggaagc gagaagaatc ataatgggga     300
aggccatcca gcctcgcgtc gcgaacgcca gcaagacgta gcccagcgcg tcggccgcca     360
tgccggcgat aatggcctgc ttctcgccga aacgtttggt ggcgggacca gtgacgaagg     420
```

```
cttgagcgag ggcgtgcaag attccgaata ccgcaagcga caggccgatc atcgtcgcgc    480
tccagcgaaa gcggtcctcg ccgaaaatga cccagagcgc tgccggcacc tgtcctacga    540
gttgcatgat aaagaagaca gtcataagtc ggcgacgat agtcatgccc cgcgcccacc     600
ggaaggagct gactgggttg aaggctctca agggcatcgg tcgacgctct cccttatgcg    660
actcctgcat taggaagcag cccagtagta ggttgaggcc gttgagcacc gccgccgcaa    720
ggaatggtgc atgcaaggag atggcgccca acagtccccc ggccacgggg cctgccacca    780
tacccacgcc gaaacaagcg ctcatgagcc cgaagtggcg agcccgatct tccccatcgg    840
tgatgtcggc gatataggcg ccagcaaccg cacctgtggc gccggtgatg ccggccacga    900
tgcgtccggc gtagaggatc cacaggacgg gtgtggtcgc catgatcgcg tagtcgatag    960
tggctccaag tagcgaagcg agcaggactg ggcggcggcc aaagcggtcg acagtgctc   1020 cgagaacggg tgcgcataga aattgcatca acgcatatag cgctagcagc acgccatagt   1080
gactggcgat gctgtcggaa tggacgatat cccgcaagag gcccggcagt accggcataa   1140
ccaagcctat gcctacagca tccagggtga cggtgccgag gatgacgatg agcgcattgt   1200
tagatttcat acacggtgcc tgactgcgtt agcaatttaa ctgtgataaa ctaccgcatt   1260
aaagcttatc gatgataagc tgtcaaacat gagaattctt gaagacgaaa gggcctcgtg   1320
atacgcctat tactagt                                                 1337
```

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: 11 base
      repeat unit of SARP binding site
<220> FEATURE:
<221> NAME/KEY: misc_feature
<222> LOCATION: (6)..(11)
<223> OTHER INFORMATION: n = a or c or g or t.

<400> SEQUENCE: 29
tgaaannnnn n                                                         11

<210> SEQ ID NO 30
<211> LENGTH: 19
<212> TYPE: PRT
<213> ORGANISM: Streptomyces cinnamoneus

<400> SEQUENCE: 30

Cys Arg Gln Ser Cys Ser Phe Gly Pro Phe Thr Phe Val Cys Asp Gly
 1               5                  10                  15

Asn Thr Lys

<210> SEQ ID NO 31
<211> LENGTH: 19
<212> TYPE: PRT
<213> ORGANISM: Unknown Organism
<220> FEATURE:
<223> OTHER INFORMATION: Description of Unknown Organism: Sequence
      source uncertain, duramycin A peptide

<400> SEQUENCE: 31

Cys Lys Gln Ser Cys Ser Phe Gly Pro Phe Thr Phe Val Cys Asp Gly
 1               5                  10                  15

Asn Thr Lys

```
<210> SEQ ID NO 32
<211> LENGTH: 19
<212> TYPE: PRT
<213> ORGANISM: Unknown Organism
<220> FEATURE:
<223> OTHER INFORMATION: Description of Unknown Organism: Sequence
      source uncertain, duramycin B peptide

<400> SEQUENCE: 32

Cys Arg Gln Ser Cys Ser Phe Gly Pro Leu Thr Phe Val Cys Asp Gly
 1               5                  10                  15

Asn Thr Lys

<210> SEQ ID NO 33
<211> LENGTH: 19
<212> TYPE: PRT
<213> ORGANISM: Unknown Organism
<220> FEATURE:
<223> OTHER INFORMATION: Description of Unknown Organism: Sequence
      source uncertain, duramycin C peptide

<400> SEQUENCE: 33

Cys Ala Asn Ser Cys Ser Tyr Gly Pro Leu Thr Trp Ser Cys Asp Gly
 1               5                  10                  15

Asn Thr Lys

<210> SEQ ID NO 34
<211> LENGTH: 19
<212> TYPE: PRT
<213> ORGANISM: Unknown Organism
<220> FEATURE:
<223> OTHER INFORMATION: Description of Unknown Organism: Sequence
      source uncertain, ancovenin peptide

<400> SEQUENCE: 34

Cys Val Gln Ser Cys Ser Phe Gly Pro Leu Thr Trp Ser Cys Asp Gly
 1               5                  10                  15

Asn Thr Lys

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer B
      B3 for producing probe BB

<400> SEQUENCE: 35
gcctacgagg accggtacgt cg                                          22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Primer BB4
      for producing probe BB

<400> SEQUENCE: 36
ggcgaagcgc aggaagagct cg                                          22

<210> SEQ ID NO 37
<211> LENGTH: 22
<212> TYPE: DNA
<213> ORGANISM: Artificial Sequence
```

```
<220> FEATURE:
<223> OTHER INFORMATION: Description of Artificial Sequence: Primer for
      cloning restriction sites into pDWFT4

<400> SEQUENCE: 37
cttcgtgtgc gacggcaaca cc                                            22

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Primer for
      cloning SpeI site into pDWFT4

<400> SEQUENCE: 38
gcagcaacta gttacttggt gttgccgtcg                                    30

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Primer for
      cloning StuI site into pDWFT4

<400> SEQUENCE: 39
ccacggaggc cttcgcctgc cgccagagct gc                                 32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Primer for
      cloning StuI site inot pDWFT4

<400> SEQUENCE: 40
ggcgaaggcc tccgtggcgg cgatgtcctt gg                                 32

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Primer for
      cloning XhoI site into pDWTF4

<400> SEQUENCE: 41
ttcagcagtc cgtcgtggac g                                             21

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Primer for
      cloning NdeI site into pDWTF4

<400> SEQUENCE: 42
gcggatacgc gttacccata cc                                            22

<210> SEQ ID NO 43
<211> LENGTH: 30
<212> TYPE: DNA
<213> ORGANISM: Artificial Sequence
<220> FEATURE:
```

<223> OTHER INFORMATION: Description of Artificial Sequence: Primer for
      cloning tetracycline resistance gene

<400> SEQUENCE: 43
gcggcgaggc ctcgccggct tccattcagg                                    30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Primer for
      cloning tetracycline resistance gene

<400> SEQUENCE: 44
gcggcgacta gtaataggcg tatcacgagg                                    30

<210> SEQ ID NO 45
<211> LENGTH: 88
<212> TYPE: DNA
<213> ORGANISM: Artificial Sequence
<220> FEATURE:
<223> OTHER INFORMATION: Description of Artificial Sequence:
      Oligonucleotide for cloning duramycin A gene

<400> SEQUENCE: 45
gcggcgaggc cttcgcctgc aagcagagct gcagcttcgg cccgttcacc ttcgtgtgcg    60
acggcaacac caagtaacta gtccggcc                                      88

<210> SEQ ID NO 46
<211> LENGTH: 88
<212> TYPE: DNA
<213> ORGANISM: Artificial Sequence
<220> FEATURE:
<223> OTHER INFORMATION: Description of Artificial Sequence:
      Oligonucleotide for cloning duramycin B gene

<400> SEQUENCE: 46
gcggcgaggc cttcgcctgc cgccagagct gcagcttcgg cccgctcacc ttcgtgtgcg    60
acggcaacac caagtaacta gtccggcc                                      88

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide for cloning duramycin A and B
      genes
<400> SEQUENCE: 47
ggccggacta gttacttggt                                               20

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Primer BAM
      for generating pDWFT4 varian

<400> SEQUENCE: 48
ggcgccggat cctaccgcaa cgacggcacc gagc                               34

<210> SEQ ID NO 49

```
<211> LENGTH: 34
<212> TYPE: DNA
<213> ORGANISM: Artificial Sequence
<220> FEATURE:
<223> OTHER INFORMATION: Description of Artificial Sequence: Primer KPN
      for generating pDWFT5 variant

<400> SEQUENCE: 49
ggcgccggta ccgaggacgt cgagctgttc gagc                              34

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Primer FTP1
      for generating pDWFT5 variant

<400> SEQUENCE: 50
caggtcgccg acgatctcgt cg                                           22

<210> SEQ ID NO 51
<211> LENGTH: 63
<212> TYPE: DNA
<213> ORGANISM: Artificial Sequence
<220> FEATURE:
<223> OTHER INFORMATION: Description of Artificial Sequence: Primer 7A
      for deleting cinorf7

<400> SEQUENCE: 51
tcgttctcac cgggaaccga ctggatgggg aaacgggcca ggcctcgccg gcttccattc   60
agg                                                                63

<210> SEQ ID NO 52
<211> LENGTH: 63
<212> TYPE: DNA
<213> ORGANISM: Artificial Sequence
<220> FEATURE:
<223> OTHER INFORMATION: Description of Artificial Sequence: Primer 7B
      for deleting cinorf7

<400> SEQUENCE: 52
acctccgatg ttgaggtgaa tcccggcacc cggcgggtga ggcctaatag gcgtatcacg   60
agg                                                                63

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Primer
      FTP35 for deleting cinA

<400> SEQUENCE: 53
ggcgacagca gcgtctcgga cc                                           22

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Primer LA
      for deleting cinA

<400> SEQUENCE: 54
ggcagcagcc acggcttacc tccgatgttg agg                               33
```

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Primer RA
      for deleting cinA

<400> SEQUENCE: 55
cggaggtaag ccgtggctgc tgcctctagg                                    30

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Primer
      FTP28 for deleting cinA

<400> SEQUENCE: 56
ttcaggtaga agcggtggta gg                                            22

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Primer LM
      for deleting cinM

<400> SEQUENCE: 57
tggagccact ccatgcgaat ttctcctgcg gtcg                               34

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Primer RM
      for deleting cinM

<400> SEQUENCE: 58
agaaattcgc atggagtggc tccaccatgg                                    30

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Primer
      FTPMR for deleting cinM

<400> SEQUENCE: 59
cggccgagct cgacgatctc c                                             21

<210> SEQ ID NO 60
<211> LENGTH: 63
<212> TYPE: DNA
<213> ORGANISM: Artificial Sequence
<220> FEATURE:
<223> OTHER INFORMATION: Description of Artificial Sequence: Primer XA
      for deleting cinX

<400> SEQUENCE: 60
cccgccgtcg caccacgaac agtaaggagt ggctccacca ggcctcgccg gcttccattc   60

```
agg                                                                       63

<210> SEQ ID NO 61
<211> LENGTH: 63
<212> TYPE: DNA
<213> ORGANISM: Artificial Sequence
<220> FEATURE:
<223> OTHER INFORMATION: Description of Artificial Sequence: Primer XB
      for deleting cinX

<400> SEQUENCE: 61
tccttggtgc cgcgcggtgc gcggacgacg ggtgccggga ggcctaatag gcgtatcacg    60
agg                                                                       63

<210> SEQ ID NO 62
<211> LENGTH: 63
<212> TYPE: DNA
<213> ORGANISM: Artificial Sequence
<220> FEATURE:
<223> OTHER INFORMATION: Description of Artificial Sequence: Primer RA
      for deleting cinR

<400> SEQUENCE: 62
tcagcactgt cgaagaacac ctcgcgccgg gagcggcata ggcctcgccg gcttccattc    60
agg                                                                       63

<210> SEQ ID NO 63
<211> LENGTH: 63
<212> TYPE: DNA
<213> ORGANISM: Artificial Sequence
<220> FEATURE:
<223> OTHER INFORMATION: Description of Artificial Sequence: Primer RB
      for deleting cinR

<400> SEQUENCE: 63
ctgctgacac ccggcccgta gcggtcacgg ctcacaccga ggcctaatag gcgtatcacg    60
agg                                                                       63

<210> SEQ ID NO 64
<211> LENGTH: 63
<212> TYPE: DNA
<213> ORGANISM: Artificial Sequence
<220> FEATURE:
<223> OTHER INFORMATION: Description of Artificial Sequence: Primer
      SARPA for deleting cinR1

<400> SEQUENCE: 64
gtcttcaggg tgcggctcga tgagcgaagg ggagagttca ggcctcgccg gcttccattc    60
agg                                                                       63

<210> SEQ ID NO 65
<211> LENGTH: 63
<212> TYPE: DNA
<213> ORGANISM: Artificial Sequence
<220> FEATURE:
<223> OTHER INFORMATION: Description of Artificial Sequence: Primer
      SARPB for deleting cinR1

<400> SEQUENCE: 65
ctcgtgcacc gccggcgcgc gcgccgggcg gtgggcggca ggcctaatag gcgtatcacg    60
agg                                                                       63
```